US009233100B2

(12) United States Patent
Soll et al.

(10) Patent No.: US 9,233,100 B2
(45) Date of Patent: Jan. 12, 2016

(54) PARASITICIDAL ORAL VETERINARY COMPOSITIONS COMPRISING SYSTEMICALLY-ACTING ACTIVE AGENTS, METHODS AND USES THEREOF

(71) Applicant: MERIAL INC., Duluth, GA (US)

(72) Inventors: Mark David Soll, Alpharetta, GA (US); Diane Larsen, Buford, GA (US); Susan Mancini Cady, Yardley, PA (US); Peter Cheifetz, East Windsor, NJ (US); Izabela Galeska, Newtown, PA (US); Saijun Gong, Bridgewater, NJ (US)

(73) Assignee: MERIAL, INC., Duluth, GA (US)

(*) Notice: Subject to any disclaimer, the term of this patent is extended or adjusted under 35 U.S.C. 154(b) by 0 days.

(21) Appl. No.: 13/754,969

(22) Filed: Jan. 31, 2013

(65) Prior Publication Data
US 2013/0203692 A1    Aug. 8, 2013

Related U.S. Application Data

(60) Provisional application No. 61/595,463, filed on Feb. 6, 2012.

(51) Int. Cl.
| A61K 45/06 | (2006.01) |
| A61K 31/27 | (2006.01) |
| A61K 31/365 | (2006.01) |
| A61K 31/42 | (2006.01) |
| A61K 31/4985 | (2006.01) |
| A61K 31/7048 | (2006.01) |
| C07D 261/04 | (2006.01) |
| A61K 31/437 | (2006.01) |
| A61K 9/00 | (2006.01) |
| A61K 47/10 | (2006.01) |
| A61K 47/12 | (2006.01) |
| A61K 47/14 | (2006.01) |
| A61K 47/32 | (2006.01) |
| A61K 47/36 | (2006.01) |
| A61K 47/44 | (2006.01) |
| A61K 31/194 | (2006.01) |

(52) U.S. Cl.
CPC .............. A61K 31/42 (2013.01); A61K 9/0056 (2013.01); A61K 9/0068 (2013.01); A61K 31/194 (2013.01); A61K 31/27 (2013.01); A61K 31/365 (2013.01); A61K 31/437 (2013.01); A61K 31/4985 (2013.01); A61K 31/7048 (2013.01); A61K 45/06 (2013.01); A61K 47/10 (2013.01); A61K 47/12 (2013.01); A61K 47/14 (2013.01); A61K 47/32 (2013.01); A61K 47/36 (2013.01); A61K 47/44 (2013.01); C07D 261/04 (2013.01)

(58) Field of Classification Search
CPC ... A61K 45/06; A61K 31/42; A61K 31/4985; A61K 31/7048; A61K 31/365; A61K 31/27; A61K 2300/00; C07D 261/04

USPC .......... 514/155, 250, 256, 368, 378; 548/240
See application file for complete search history.

(56) References Cited

U.S. PATENT DOCUMENTS

| 3,887,964 A | 6/1975 | Richards |
| 4,284,652 A | 8/1981 | Christensen |
| 4,327,076 A | 4/1982 | Puglia et al. |
| 4,393,085 A | 7/1983 | Spradlin et al. |
| 4,609,543 A | 9/1986 | Morris et al. |
| 4,935,243 A | 6/1990 | Borkan et al. |
| 4,997,671 A | 3/1991 | Spanier |
| 5,236,730 A | 8/1993 | Yamada et al. |
| 5,262,167 A | 11/1993 | Vegesna et al. |
| 5,380,535 A | 1/1995 | Geyer et al. |
| 5,439,924 A | 8/1995 | Miller |
| 5,578,336 A | 11/1996 | Monte |
| 5,605,889 A | 2/1997 | Curatolo et al. |
| 5,637,313 A | 6/1997 | Chau |
| 5,753,255 A | 5/1998 | Chaukin et al. |
| 5,824,336 A | 10/1998 | Jans et al. |
| 5,827,565 A | 10/1998 | Axelrod |
| 5,958,445 A | 9/1999 | Humber et al. |
| 6,060,078 A | 5/2000 | Lee |
| 6,086,940 A | 7/2000 | Axelrod |
| 6,093,427 A | 7/2000 | Axelrod |
| 6,093,441 A | 7/2000 | Axelrod |
| 6,110,521 A | 8/2000 | Axelrod |

(Continued)

FOREIGN PATENT DOCUMENTS

| AU | 2008320992 A1 | 6/2010 |
| AU | 2010206029 | 8/2010 |

(Continued)

OTHER PUBLICATIONS

Glossary of medical education terms, Institute of International Medical Education. http://www.iime.org/glossary.htm Accessed in Mar. 2013.*
Halos et al. Flea control failure? Myths and realities. Trends Parasitol 30:228-233, May 2014.*
Emea Report. Committee for Veterinary Medicinal Products: Polyethylene Glycol Stearates and Polyethylene Glycol 15 Hydroxystearate, Summary Report. EMEAfMRL/392/98-FINAL_Rev.1, Jun. 2003.*

(Continued)

Primary Examiner — Scarlett Goon
Assistant Examiner — Yih-Horng Shiao
(74) Attorney, Agent, or Firm — Judy Jarecki-Black; John Ezcurra; Merial, Inc.

(57) ABSTRACT

This invention relates to oral veterinary compositions for combating ectoparasites and endoparasites in animals, comprising at least one systemically-acting active agent in combination with a pharmaceutically acceptable carrier. This invention also provides for improved methods for eradicating, controlling, and preventing parasite infections and infestations in an animal comprising administering the compositions of the invention to the animal in need thereof.

39 Claims, 3 Drawing Sheets

(56) References Cited

U.S. PATENT DOCUMENTS

| | | |
|---|---|---|
| 6,159,516 A | 12/2000 | Axelrod et al. |
| 6,270,790 B1 | 8/2001 | Robinson et al. |
| 6,387,381 B2 | 5/2002 | Christensen |
| 6,500,463 B1 | 12/2002 | van Lengerich |
| 7,348,027 B2 | 3/2008 | Rose et al. |
| 7,662,972 B2 | 2/2010 | Mita et al. |
| 7,947,715 B2 | 5/2011 | Mita et al. |
| 7,951,828 B1 | 5/2011 | Mita et al. |
| 7,955,632 B2 | 6/2011 | Paulsen et al. |
| 2001/0036464 A1 | 11/2001 | Christensen |
| 2001/0055598 A1 | 12/2001 | Kolbe et al. |
| 2003/0007958 A1 | 1/2003 | Chen |
| 2004/0037869 A1 | 2/2004 | Cleverly et al. |
| 2004/0043925 A1 | 3/2004 | Kolbe et al. |
| 2004/0234579 A1 | 11/2004 | Finke |
| 2005/0032718 A1 | 2/2005 | Burke et al. |
| 2005/0226908 A1 | 10/2005 | Huron et al. |
| 2006/0141009 A1 | 6/2006 | Cady et al. |
| 2006/0222684 A1 | 10/2006 | Isele |
| 2009/0280159 A1 | 11/2009 | Paulsen et al. |
| 2010/0144797 A1 | 6/2010 | Mita et al. |
| 2010/0144808 A1 | 6/2010 | Mita et al. |
| 2010/0179194 A1 | 7/2010 | Mihara et al. |
| 2010/0179195 A1 | 7/2010 | Lahm et al. |
| 2010/0254960 A1 | 10/2010 | Long et al. |
| 2011/0009438 A1 | 1/2011 | Mita et al. |
| 2011/0059988 A1 | 3/2011 | Heckeroth et al. |
| 2011/0118212 A1 | 5/2011 | Koerber et al. |
| 2011/0152312 A1 | 6/2011 | Le Hir de Fallois et al. |
| 2011/0159107 A1 | 6/2011 | Koerber et al. |
| 2011/0166193 A1 | 7/2011 | Renold et al. |
| 2011/0257011 A1 | 10/2011 | Kaiser et al. |
| 2012/0030841 A1 | 2/2012 | Koerber et al. |
| 2012/0035122 A1 | 2/2012 | Vaillancourt et al. |
| 2012/0077765 A1 | 3/2012 | Curtis et al. |
| 2013/0065846 A1* | 3/2013 | Soll et al. .................. 514/30 |

FOREIGN PATENT DOCUMENTS

| | | |
|---|---|---|
| EP | 0273001 | 6/1988 |
| EP | 492235 | 7/1992 |
| EP | 075443 | 3/1993 |
| EP | 1023841 | 8/2000 |
| EP | 1247456 | 10/2002 |
| GB | 2300103 | 10/1996 |
| NZ | 286545 A1 | 11/1998 |
| NZ | 568394 A | 6/2010 |
| WO | 99/48372 | 9/1999 |
| WO | 02/060255 | 8/2002 |
| WO | 02094288 A1 | 11/2002 |
| WO | 03/030653 A2 | 4/2003 |
| WO | 2005/013714 | 2/2005 |
| WO | 2005/013714 A1 | 2/2005 |
| WO | 2005016356 A1 | 3/2005 |
| WO | 2005/062782 | 7/2005 |
| WO | 2005/099453 | 10/2005 |
| WO | 2005/099692 | 10/2005 |
| WO | 2007/070606 | 6/2007 |
| WO | 2007/075459 | 7/2007 |
| WO | 2007/079162 | 7/2007 |
| WO | 2007/123855 | 11/2007 |
| WO | 2008/030469 | 3/2008 |
| WO | 2008/134819 | 11/2008 |
| WO | 2008/136791 | 11/2008 |
| WO | 2008/144275 | 11/2008 |
| WO | 2008/148027 | 12/2008 |
| WO | 2008/154528 | 12/2008 |
| WO | 2009/002809 | 12/2008 |
| WO | WO2009/002809 * | 12/2008 |
| WO | 2010/003923 | 1/2010 |
| WO | 2010/056999 | 5/2010 |
| WO | 2010/079077 | 7/2010 |
| WO | 2010/084067 | 7/2010 |
| WO | 2011/067272 | 6/2011 |
| WO | 2011/092287 | 8/2011 |
| WO | 2011/104087 | 9/2011 |
| WO | 2011/149749 | 12/2011 |
| WO | 2011/154433 | 12/2011 |
| WO | 2011/154434 | 12/2011 |
| WO | 2011/154494 | 12/2011 |
| WO | 2011/157733 | 12/2011 |
| WO | 2012/007426 | 1/2012 |
| WO | 2012/038851 | 3/2012 |
| WO | 2012/049156 | 4/2012 |

OTHER PUBLICATIONS

Starch 1500 Partially pregelatinized maize starch technical information brochure; Colorcon company, 1999.

* cited by examiner

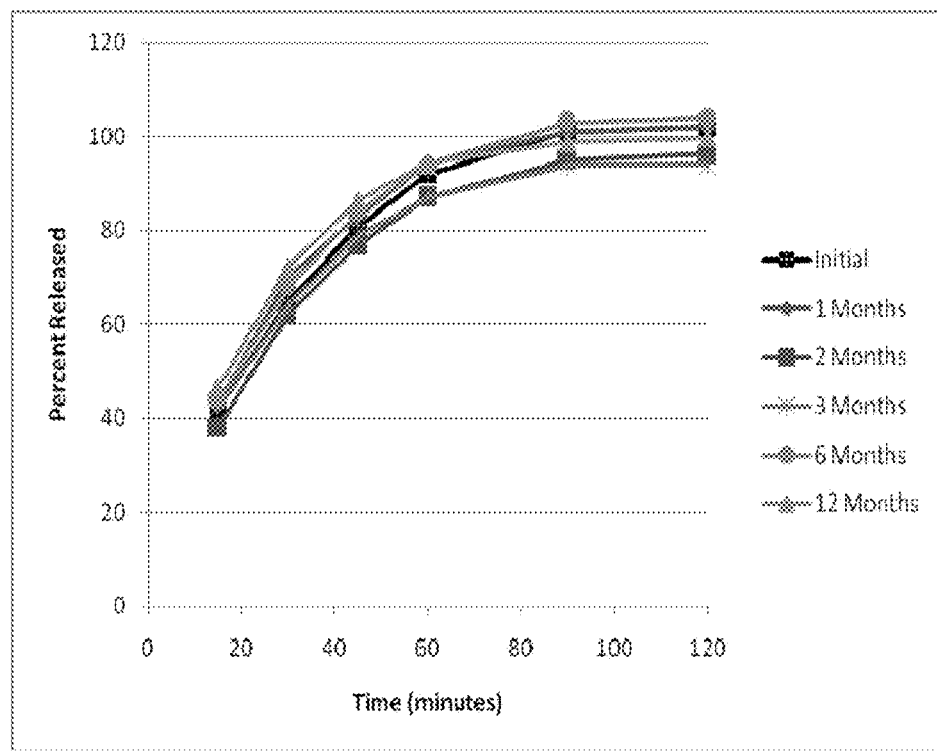
Figure 1: Average Dissolution of 2g Chewables Stored at 25°C/60%RH
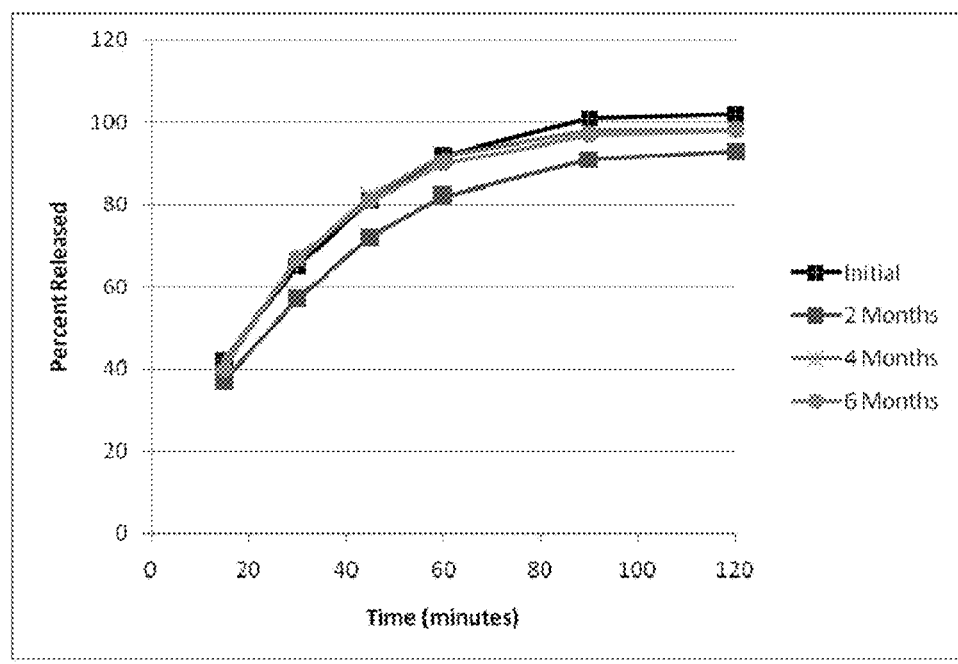
Figure 2. Average Dissolution of 2g Chewables Stored at 40°C/75%RH

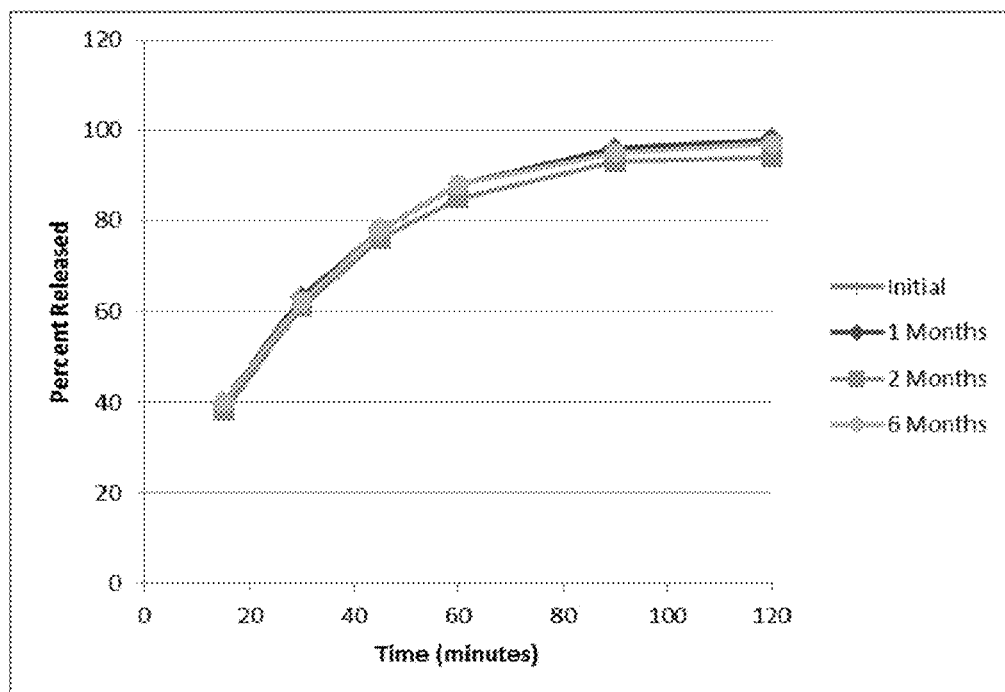
Figure 3. Average Dissolution of 4g Chewables Stored at 25°C/60%RH
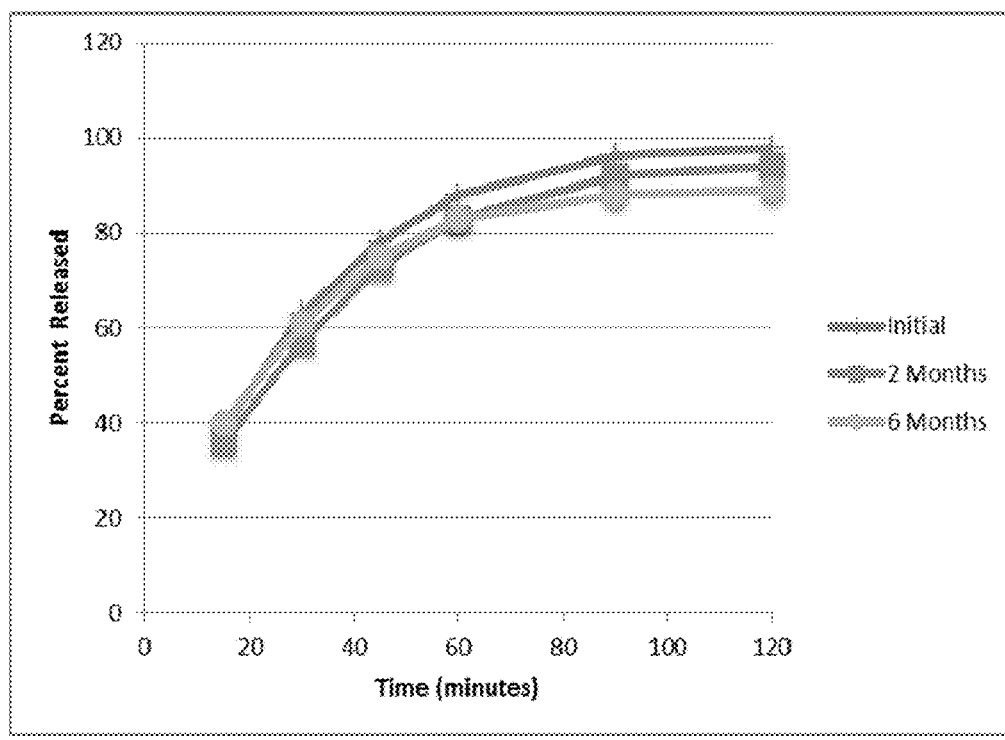
Figure 4. Average Dissolution of 4g Chewables Stored at 40°C/75%RH

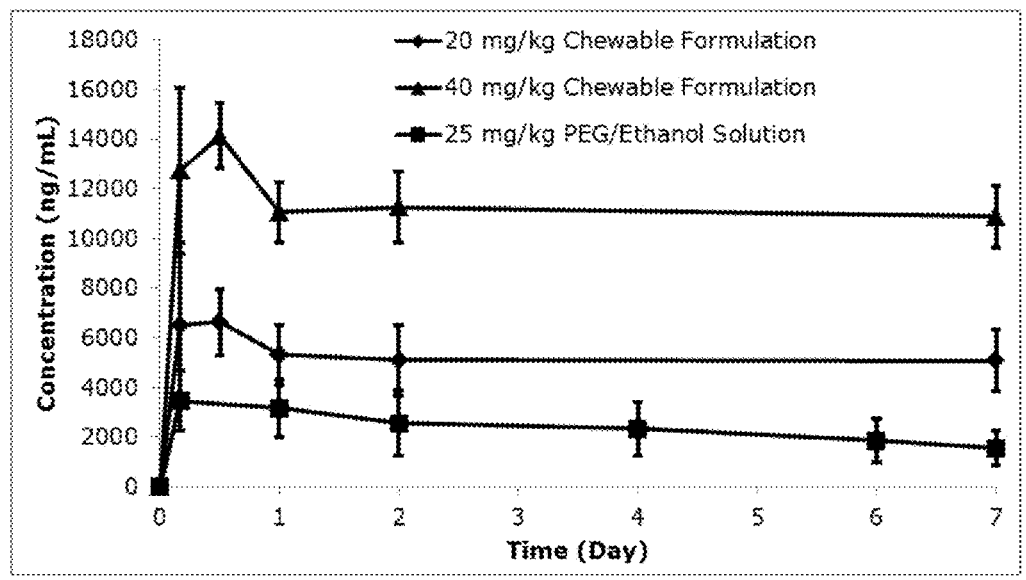
Figure 5: Plasma Concentration of Compound A from Chewable Compositions

PARASITICIDAL ORAL VETERINARY COMPOSITIONS COMPRISING SYSTEMICALLY-ACTING ACTIVE AGENTS, METHODS AND USES THEREOF

CROSS REFERENCE TO RELATED APPLICATIONS

This application claims the benefit of priority to U.S. Provisional Application No. 61/595,463 filed Feb. 6, 2012, which is incorporated herein by reference in its entirety.

FIELD OF THE INVENTION

The present invention provides oral veterinary compositions comprising at least one systemically-acting active agent for controlling ectoparasites and/or endoparasites in animals; the use of these compositions to control ectoparasites and/or endoparasites, and methods for preventing or treating parasitic infections and infestations in animals.

BACKGROUND OF THE INVENTION

Animals including mammals and birds are often susceptible to parasite infestations/infections. These parasites may be ectoparasites or endoparasites. Domesticated animals, such as cats and dogs, are often infested with one or more of the following ectoparasites:

fleas (e.g. *Ctenocephalides* spp., such as *Ctenocephalides fells* and the like);

ticks (e.g. *Rhipicephalus* spp., *Ixodes* spp., *Dermacentor* spp., *Amblyoma* spp., *Haemaphysalis* spp., and the like);

mites (e.g. *Demodex* spp., *Sarcoptes* spp., *Otodectes* spp., *Cheyletiella* spp., and the like);

lice (e.g. *Trichodectes* spp., *Felicola* spp., *Linognathus* spp., and the like);

mosquitoes (*Aedes* spp., *Culex* spp., *Anopheles* spp. and the like); and flies (*Musca* spp., *Stomoxys* spp., *Dermatobia* spp., and the like).

Fleas are a problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and/or psychological health of the animal or human. However, the most serious problem associated with ticks is that they are vectors of pathogenic agents affecting both humans and animals. Major diseases which may be transmitted by ticks include borreliosis (Lyme disease caused by *Borrelia burgdorferi*), babesiosis (or *piroplasmosis* caused by *Babesia* spp.) and rickettsioses (e.g. Rocky Mountain spotted fever). Ticks also release toxins which cause inflammation or paralysis in the host. Occasionally, these toxins may be fatal to the host.

Animals and humans also suffer from endoparasitic infections caused by parasitic worms categorized as cestodes (tapeworms), nematodes (roundworms) and trematodes (flatworms or flukes). These parasites cause a variety of pathologic conditions in domestic animals including dogs, cats, pigs, sheep, horses, cattle and poultry. Nematode parasites which occur in the gastrointestinal tract of animals and humans include those of the genera *Ancylostoma, Necator, Ascaris, Strongyloides, Trichinella, Capillaria, Toxocara, Toxascaris, Trichuris, Enterobius, Haemonchus, Trichostrongylus, Ostertagia, Cooperia, Oesophagostomum, Bunostomum, Strongylus, Cyathostomum,* and *Parascaris* among others, and those that are found in the blood vessels or other tissues and organs include *Onchocerca, Dirofilaria, Wuchereria* and the extra intestinal stages of *Strongyloides, Toxocara* and *Trichinella*. Therapeutic agents are administered to animals by a variety of routes.

These routes include, for example, oral ingestion, topical application or parenteral administration. The particular route selected by the practitioner depends upon factors such as the physicochemical properties of the pharmaceutical or therapeutic agent, the condition of the host and economics. In certain cases, it is convenient and efficient to administer veterinary medicines orally by placing the therapeutic agent in a solid or liquid matrix that is suitable for oral delivery. These methods include chewable drug-delivery formulations. The problem associated with administering oral formulations to animals is that the therapeutic agent often provides an unpleasant taste, aroma, or texture, which causes the animals to reject the composition. This is further exacerbated by compositions that are hard and difficult to swallow.

Oral veterinary compositions in the form of soft chewable compositions ("soft chews"), or chewable tablets that are palatable are usually convenient to administer to certain animals, particularly cats and dogs, and may be used effectively to dose veterinary medicine to these animals. However, many oral compositions comprising active agents with a bitter or unpleasant taste are not well accepted by cats and dogs. Furthermore, when the bioavailability of an active agent from an oral dosage form is not sufficient or is variable, the required exposure of the animal to the active ingredient may not be sufficient to provide the desired efficacy. Problems such as these often lead to low or sub-optimal efficacy and control of parasites.

Chewable dosage forms for drug delivery are well known to pharmaceutical technology. It is known in the pharmaceutical industry that the act of chewing increases the surface area of the available active ingredient and may increase the rate of absorption by the digestive tract. Chewable systems are also advantageous where it is desirable to make an active ingredient available topically to the mouth or throat areas for both local effects and/or systemic absorption. Further, chewable dosage forms are also utilized to ease drug administration in pediatric and geriatric patients. Examples of chewable dosage forms may be found in U.S. Pat. Nos. 6,387,381; 4,284,652; 4,327,076; 4,935,243; 6,270,790; 6,060,078; 4,609,543; and, 5,753,255, all incorporated herein by reference.

Palatability and "mouth feel" are important characteristics to be considered in providing a dosage form, or matrix, for an active pharmaceutical or medicinal. Unfortunately, many pharmaceuticals and other active ingredients have a bitter or otherwise unpalatable taste, or an unacceptable mouth feel, due to the grittiness or chalkiness of the compound, or both. These characteristics make it difficult to incorporate such active ingredients into the current state of the art for chewable dosage forms because the objectionable taste and/or mouth feel make it less likely to obtain compliance by the user. Oral veterinary dosage forms that are not palatable to the animal treated result in low acceptance of the medicament by the animal and a low level of compliance. Thus, there is a need for improved oral veterinary dosage forms that are palatable and well accepted by the treated animal.

Another challenge with oral veterinary compositions, particularly soft chewable compositions, is that the release and dissolution of the active agent from the composition after it is ingested by the animal can be variable and incomplete. This leads to variability in the amount of the drug that is absorbed from the digestive tract of the animal.

U.S. Pat. No. 7,955,632 (incorporated herein by reference) describes palatable, edible soft chewable medication vehicles for the delivery of pharmaceutically acceptable active ingredients to an animal and processes of making the same.

US 2004/0037869 A1 and WO 2004/016252 to Cleverly et al. (incorporated herein by reference) describe non-animal product containing veterinary formulations, including chewable veterinary formulations and tablets, that contain at least one pharmaceutical active agent and do not contain animal products.

US 2004/0151759 A1 and WO 2005/062782 to Cleverly et al. (incorporated herein by reference) describe non-animal product containing veterinary formulations comprising a) at least one nodulisporamide or a nodulisporic acid derivative; or b) a combination comprising i) at least one avermectin or milbemycin derivative; and ii) at least one of praziquantel or pyrantel.

WO 2009/02451A2 and US 2011/0059988 to Heckeroth et al. describe various parasiticidal compositions comprising isoxazoline active agents for the control of parasites on animals. The compositions include compositions for oral administration.

Traditionally, in veterinary formulations, palatability had been achieved by the inclusion of animal byproducts or flavors derived from animal sources into the formulation. For example, it is customary to include excipients, such as chicken powder, liver powder, beef, ham, fish, or rawhide-derived products in dog chews to make the chew attractive and palatable to the dog. See, e.g., U.S. Pat. No. 6,086,940; U.S. Pat. No. 6,093,441; U.S. Pat. No. 6,159,516; U.S. Pat. No. 6,110,521; U.S. Pat. No. 5,827,565; U.S. Pat. No. 6,093,427, all to Axelrod et al. (all incorporated herein by reference).

Notwithstanding the compositions comprising parasiticidal active agents described in the documents above, there is a need for palatable oral veterinary compositions that are well accepted by the animals treated and methods with improved duration of efficacy, bioavailability, and spectrum of coverage to protect animals against endoparasites and/or ectoparasites. Optimal compositions should be palatable and well accepted by the animals, provide good oral bioavailability, be efficacious against external and/or internal parasites, have a quick onset of activity, have a long duration of activity, and be safe to the animal recipients and/or their human owners. This invention addresses this need.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention is directed to soft chewable veterinary compositions comprising at least one systemically-acting parasiticidal active agent and their use to control external and/or internal parasites in or on warm-blooded animals and birds. In accordance with this invention, it has been discovered that these oral compositions surprisingly provide exceptionally high bioavailability of the active agent resulting in plasma levels sufficient to provide excellent protection against parasites for an extended period of time, unmatched by known oral veterinary compositions. The oral compositions of the invention are exceptionally palatable and provide desirable safety profiles for warm-blooded animals and birds, while providing excellent protection against parasites. In addition, it has been discovered that a single administration of the inventive compositions generally provides potent activity against one or more ectoparasites and/or endoparasites with a fast onset of activity and at the same time providing a long duration of efficacy.

In certain embodiments, the veterinary compositions of the invention are advantageously in the form of soft chewable formulations that are palatable for animals, including cats and dogs. In another embodiment, the oral veterinary compositions of the invention are in the form of a chewable tablet.

The invention encompasses uses of the soft chewable veterinary compositions for the treatment and/or prophylaxis of parasitic infections and infestations of animals (either wild or domesticated), including livestock and companion animals with the aim of ridding these hosts of parasites commonly encountered by such animals. Animals that may benefit from the inventive oral compositions include, but are not limited to, cats, dogs, horses, chickens, sheep, goats, pigs, turkeys and cattle, among others.

The invention also provides methods for the treatment and/or prevention of parasitic infections and infestations in animals, comprising administering an effective amount of a composition of the invention comprising at least one systemically-acting parasiticide to the animal. Surprisingly, it has been found that the inventive compositions and formulations described herein exhibit superior broad spectrum efficacy against harmful ectoparasites and/or endoparasites more rapidly, and over a longer duration compared to oral veterinary compositions known in the art.

In one embodiment, the invention provides soft chewable veterinary compositions comprising effective amounts of a) (i) at least one isoxazoline active agent; or
  (ii) at least one systemically-acting active agent that is active against internal parasites, wherein the systemically-acting active agent that is active against internal parasites is one or more macrocyclic lactones, one or more benzimidazoles, levamisole, pyrantel, morantel, praziquantel, closantel, clorsulon, one or more amino acetonitrile active agents or one or more aryloazol-2-yl cyanoethylamino active agents, or a combination of thereof; or
  (iii) a combination of at least one isoxazoline active agent of formula (I) and at least one additional systemically-acting active agent, wherein the systemically active agent is one or more macrocyclic lactones, one or more spinosyn compounds, one or more spinosoid compounds, one or more benzimidazoles, levamisole, pyrantel, morantel, praziquantel, closantel, clorsulon, one or more amino acetonitrile active agents, one or more arylpyrazoles, one or more insect growth regulators, one or more neonicotinoids or one or more aryloazol-2-yl cyanoethylamino active agents, or a combination of thereof; and b) a pharmaceutically acceptable carrier.

In one embodiment, the isoxazoline active agent has the formula (I) below where variables $A^1, A^2, A^3, A^4, A^5, A^6, B^1, B^2, B^3, R^1, R^2, R^4, R^5$, W and n are defined herein:

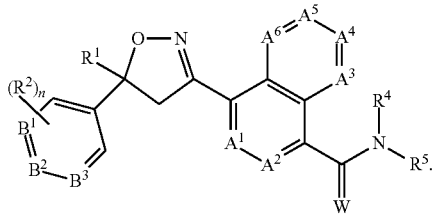

In another embodiment, the compositions of the invention comprise an isoxazoline compound of formula (II), (III) or (IV) described herein.

In one embodiment, the invention provides soft chewable compositions comprising an isoxazoline active agent of formula (I) wherein W is O, $R^1$ is $CF_3$, $B^2$ is CH, $B^1$ is C—Cl, $B^3$ is C—$CF_3$, each of $A^1$, $A^2$, $A^3$, $A^4$, $A^5$ and $A^6$ is CH; $R^4$ is H and $R^5$ is —$CH_2C(O)NHCH_2CF_3$. In some embodiments, the soft chewable veterinary compositions and methods comprise 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (Compound A) as the isoxazoline active agent.

In still another embodiment of the invention, the compositions comprise an isoxazoline Compound B or Compound 1.001-1.025 or Compound 2.001-2.018 described below.

In another embodiment, the compositions of the invention may include at least one isoxazoline active agent in combination with one or more additional active agents. In one embodiment, the composition may comprise at least one isoxazoline active agent in combination with at least one macrocyclic lactone active agent, including, but not limited to, an avermectin or milbemycin compound. In some embodiments, the avermectin or milbemycin active agent is eprinomectin, ivermectin, selamectin, abamectin, emamectin, latidectin, lepimectin, milbemectin, milbemycin D, milbemycin oxime, or moxidectin, or a combination thereof.

In one embodiment, the soft chewable compositions of the invention comprise one or more fillers, one or more flavoring agents, one or more binders, one or more solvents, one or more surfactants, one or more humectants and optionally an antioxidant or a preservative.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 is a plot showing the average dissolution of 2 gram size soft chewable compositions of the invention containing about 2.3% (w/w) of Compound A which have been stored at 25° and 60% relative humidity (RH).

FIG. 2 is a plot showing the average dissolution of 2 gram size soft chewable compositions of the invention containing about 2.3% (w/w) of Compound A which have been stored at 40° and 75% relative humidity (RH).

FIG. 3 is a plot showing the average dissolution of 4 gram size soft chewable compositions of the invention containing about 2.3% (w/w) of Compound A which have been stored at 25° and 60% relative humidity (RH).

FIG. 4 is a plot showing the average dissolution of 4 gram size soft chewable compositions of the invention containing about 2.3% (w/w) of Compound A which have been stored at 40° and 75% relative humidity (RH).

FIG. 5 shows the plasma concentration of Compound A in dogs over time after administration of soft chewable compositions at doses of 20 mg/kg and 40 mg/kg compared with administration of Compound A in a polyethyleneglycol/alcohol based solution.

DETAILED DESCRIPTION

The present invention provides novel and inventive oral veterinary compositions comprising at least one systemically-acting parasiticide together with a pharmaceutically acceptable carrier or diluent.

In one embodiment of the invention, the veterinary compositions are in the form of a soft chewable composition. In another embodiment of the invention, the oral veterinary compositions are in the form of a chewable tablet. Each of the compositions of the invention is palatable to the animal and provides for easy administration of the composition to the animal. These compositions provide surprisingly effective protection of the animals against parasites for an extended period of time, while also providing a fast onset of action. The compositions of the invention have been surprisingly found to have an exceptionally high bioavailability with rapid absorption of the active into the blood stream of the animal. The exceptional bioavailability of the compositions is the result of the combination of the non-active components of the compositions together with the properties of the active agent. In one embodiment of the invention, the exceptionally high bioavailability of an isoxazoline active ingredient from the oral veterinary compositions along with the intrinsic half-life of the active agent in the body and its potency provide for unparalleled long lasting efficacy against ectoparasites from an oral dosage form. This effect is quite surprising and unexpected.

Also provided are methods for the treatment and/or prophylaxis of parasitic infections and infestations of animals, comprising administering an effective amount of an oral veterinary composition of the invention to the animal. The invention also provides uses of the inventive compositions in the treatment and/or prophylaxis of parasitic infections and/infestations and in the manufacture of a medicament for the treatment and/or prophylaxis of parasitic infections and/or infestations in animals.

The oral veterinary compositions of the invention include, but are not limited to, soft chewable and chewable tablet compositions. The invention includes at least the following features:

(a) palatable oral veterinary compositions, including soft chewable and chewable tablet compositions, that provide superior efficacy against parasites comprising an effective amount of at least one isoxazoline active agent together with a pharmaceutically acceptable carrier or diluent;

(b) palatable oral veterinary compositions comprising an effective amount at least one isoxazoline active agent formula (I), formula (II), formula (III) or formula (IV) that provide surprisingly high plasma concentrations and bioavailability of the isoxazoline active agent;

(c) palatable oral veterinary compositions that exhibit superior fast-acting efficacy that comprise an effective amount of at least one isoxazoline compound of formula (I), formula (II), formula (III) or formula (IV) described herein together with a pharmaceutically acceptable carrier or diluent;

(d) palatable oral veterinary compositions that exhibit superior fast acting and long lasting efficacy that comprise an effective amount of at least one isoxazoline Compound A, Compound B, Compound 1.001-1.025 or Compound 2.001-2.018 described herein together with a pharmaceutically acceptable carrier or diluent;

(e) palatable oral veterinary compositions comprising an effective amount of at least one isoxazoline active agent in combination with one or more macrocyclic lactones, one or more spinosyn compounds, one or more spinosoid compounds, a benzimidazole, levamisole, pyrantel, morantel, praziquantel, closantel, clorsulon, one or more amino acetonitrile active agent, one or more insect growth regulators, one or more neonicotinoids, one or more arylpyrazoles, or one or more aryloazol-2-yl cyanoethylamino active agents, or a combination of thereof, in combination with a pharmaceutically acceptable carrier or diluent;

(f) palatable oral veterinary compositions that exhibit superior fast acting and long lasting efficacy that comprise an effective amount of at least one isoxazoline Compound A, Compound B, Compound 1.001-1.025 or Compound 2.001-2.018 described herein in combination with one or more macrocyclic lactone active agent, together with a pharmaceutically acceptable carrier or diluent;

(g) palatable oral veterinary compositions, including soft chewable and chewable tablet compositions, comprising an effective amount of at least one systemically-active parasiticide that is active against internal parasites together with a pharmaceutically acceptable carrier or diluent.

(h) palatable oral veterinary compositions, including soft chewable and chewable tablet compositions, comprising an effective amount of at least one systemically-active parasiticide active agent that is active against internal parasites selected from the group consisting of one or more macrocyclic lactones, a benzimidazole, levamisole, pyrantel, morantel, praziquantel, closantel, clorsulon, one or more amino acetonitrile active agent, and one or more aryloazol-2-yl cyanoethylamino active agents, or a combination of thereof;

(i) a chewable oral composition comprising an isoxazoline active agent of formulae (I), (II), (III) or formula (IV) for use in the treatment or prophylaxis of a parasitic infection or infestation in an animal;

(j) a chewable oral composition comprising an effective amount of at least one systemically-acting active agent that is active against internal parasites selected from the group consisting of one or more macrocyclic lactones, one or more benzimidazoles, levamisole, pyrantel, morantel, praziquantel, closantel, clorsulon, one or more amino acetonitrile active agents and one or more aryloazol-2-yl cyanoethylamino active agents, or a combination of thereof, for use in the treatment or prophylaxis of a parasitic infection or infestation in an animal;

(k) methods for the treatment and/or prevention of parasitic infections and infestations in an animal comprising administering an effective amount of an oral veterinary composition of the invention comprising at least one isoxazoline compound together with a pharmaceutically acceptable carrier or diluent;

(l) methods for the treatment and/or prevention of parasitic infections and infestations in an animal comprising administering an effective amount of an oral veterinary composition of the invention comprising at least one isoxazoline of formula (I), formula (II), formula (III) or formula (IV), alone or in combination with one or more macrocyclic lactones, one or more spinosyn compounds, one or more spinosoid compounds, a benzimidazole, levamisole, pyrantel, morantel, praziquantel, closantel, clorsulon, one or more amino acetonitrile active agent, one or more insect growth regulators, one or more neonicotinoids, one or more arylpyrazoles, or one or more aryloazol-2-yl cyanoethylamino active agents, or a combination of thereof, together with a pharmaceutically acceptable carrier or diluent;

(m) methods for the treatment and/or prevention of parasitic infections and infestations in an animal comprising administering to an animal an effective amount of an oral veterinary composition of the invention comprising at least one isoxazoline Compound A, Compound B, Compound 1.001-1.025 or Compound 2.001-2.018 described herein in combination with one or more macrocyclic lactone active agents, together with a pharmaceutically acceptable carrier or diluent;

(n) methods for the treatment and/or prevention of parasitic infections and infestations in an animal comprising administering an effective amount of an oral veterinary composition of the invention comprising at least one isoxazoline Compound A, Compound B, Compound 1.001-1.025 or Compound 2.001-2.018, alone or in combination with one or more macrocyclic lactones, one or more spinosyn compounds, one or more spinosoid compounds, a benzimidazole, levamisole, pyrantel, morantel, praziquantel, closantel, clorsulon, one or more amino acetonitrile active agent, one or more insect growth regulators, one or more neonicotinoids, one or more arylpyrazoles, or one or more aryloazol-2-yl cyanoethylamino active agents, or a combination of thereof, together with a pharmaceutically acceptable carrier or diluent;

(o) methods for the treatment and/or prevention of endoparasitic infections in an animal comprising administering an effective amount of an oral veterinary compositions, including soft chewable and chewable tablet compositions, comprising an effective amount of at least one systemically-active parasiticide active agent that is active against internal parasites selected from the group consisting of one or more macrocyclic lactones, one or more benzimidazoles, levamisole, pyrantel, morantel, praziquantel, closantel, clorsulon, one or more amino acetonitrile active agent and one or more aryloazol-2-yl cyanoethylamino active agents, or a combination of thereof;

(p) use of oral veterinary compositions of the invention comprising at least one isoxazoline compound of formula (I), formula (II), formula (III) or formula (IV), alone or in combination with one or more macrocyclic lactones, one or more spinosyn compounds, one or more spinosoid compounds, a benzimidazole, levamisole, pyrantel, morantel, praziquantel, closantel, clorsulon, one or more amino acetonitrile active agent, one or more insect growth regulators, one or more neonicotinoids, one or more arylpyrazoles, or one or more aryloazol-2-yl cyanoethylamino active agents, or a combination of thereof, together with a pharmaceutically acceptable carrier or diluent in the prevention or treatment of animal parasites;

(q) use of the oral veterinary compositions of the invention comprising at least one of Compound A, Compound B, Compound 1.001 to 1.025 or Compound 2.001 to 2.018, alone or in combination with one or more macrocyclic lactones, one or more spinosyn compounds, one or more spinosoid compounds, a benzimidazole, levamisole, pyrantel, morantel, praziquantel, closantel, clorsulon, one or more amino acetonitrile active agent, one or more insect growth regulators, one or more neonicotinoids, one or more arylpyrazoles, or one or more aryloazol-2-yl cyanoethylamino active agents, or a combination of thereof, together with a pharmaceutically acceptable carrier or diluent in the treatment and/or prevention of a parasitic infestation and infections in an animal;

(r) the use of an isoxazoline active agent of formulae (I), (II), (III) or (IV) in the preparation of a chewable oral veterinary composition for the treatment of a parasitic infection or infestation in an animal;

(s) use of the oral veterinary compositions of the invention comprising at least one systemically-acting active agent that is active against internal parasites selected from the group consisting of one or more macrocyclic lactones, one or more benzimidazoles, levamisole, pyrantel, morantel, praziquantel, closantel, clorsulon, one or more amino acetonitrile active agent, and one or more aryloazol-2-yl cyanoethylamino active agents, or a combination of thereof, together with a pharmaceutically acceptable carrier or diluent in the treatment and/or prevention of a parasitic infection in an animal; or a combination thereof; and (t) the use of at least one systemically-active parasiticide active agent that is active against internal parasites selected from the group consisting of one or more macrocyclic lactones, one or more benzimidazoles, levamisole, pyrantel, morantel, praziquantel, closantel, clorsulon, one or more amino acetonitrile active agents, and one or more aryloazol-2-yl cyanoethylamino active agents, or a combination of thereof, in the in the preparation of a chewable oral veterinary composition for the treatment of a parasitic infection or infestation in an animal.

In this disclosure and in the claims, terms such as "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

DEFINITIONS

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals. Animals include, but are not limited to, cats, dogs, cattle, chickens, turkeys, deer, goats, horses, llamas, pigs, sheep, yaks, rodents and birds. It also includes an individual animal in all stages of development, including embryonic and fetal stages. In some embodiments, the animal will be a non-human animal.

The expression "effective amount" as used herein means a concentration of the active agent in the composition sufficient to elicit the desired biological response to the target parasite(s) after administration of the composition to the animal, as measured by methods known in the art and/or described in the examples herein. In some embodiments, an "effective amount" of the active agent in the composition will provide an efficacy of at least 70% against the target parasite compared to an untreated control. In other embodiments, "an effective amount" of the active agent will provide an efficacy of at least 80%, or at least 85% compared to untreated controls. More typically, "an effective amount" of the active agent will provide an efficacy of at least 90%, at least 93%, at least 95% or at least 97% against the target parasite. In certain embodiments, including the prevention of *Dirofilaria immitis*, the term "effective amount" may provide efficacy as high as 100%.

As used herein, the terms "systemically-acting" or "systemically active" will be understood to mean that the active compounds are active when administered orally and may be distributed through the plasma and/or tissues of the animal treated and act on the parasite when a blood meal is taken or when the parasite comes in contact with the active agent.

As used herein, the term "amylaceous ingredients" is meant those food-stuffs containing a preponderance of starch and/or starch-like material. Examples of amylaceous ingredients are cereal grains and meals or flours obtained upon grinding cereal grains such as corn, oats, wheat, milo, barley, rice, and the various milling by-products of these cereal grains such as wheat feed flour, wheat middlings, mixed feed, wheat shorts, wheat red dog, oat groats, hominy feed, and other such material. Also included as sources of amylaceous ingredients are the tuberous food stuffs such as potatoes, tapioca, and the like.

As used herein the term "palatable" means an oral veterinary composition that is readily accepted by dogs without any coaxing or with limited coaxing. Palatable compositions are compositions that are consumed by at least 75% of dogs without manual administration of the composition.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl", which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-S(O)$_2$—, wherein alkyl is as defined above. Similarly, the term "haloalkylsulfonyl" refers to haloalkyl-S(O)$_2$— where haloalkyl is as defined above.

The term alkylamino and dialkylamino refer to alkyl-NH— and (alkyl)$_2$N— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl refer to alkyl-C (O)—, alkoxy-C(O)—, alkylamino-C(O)— and dialkylamino-C(O)— where alkyl, alkoxy, alkylamino and dialkylamino are as defined above. Similarly, the terms "halo alkylcarbonyl," "halo alkoxycarbonyl," "halo alkylamino carbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—CH$_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, isoxazolinyl, quinazolinyl, quinoxalinyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolinyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl), or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$)).

Stereoisomers and Polymorphic Forms

It will be appreciated by those of skill in the art that certain compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that compounds containing a sulfoxide functional group may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents.

Salts

Also contemplated within the scope of the invention are acid or base salts, where applicable, of the compounds of the invention provided for herein.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids, fatty acids and sulfonic acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid. Sulfonic acids include alkyl or haloalkylsulfonic acids and arylsulfonic acids including, but not limited to methane sulfonic acid, ethane sulfonic acid, benzenesulfonic acid and naphthalenesulfonic acid, among others.

The term "base" contemplates all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkyl- and dialkylammonium salts, and salts of cyclic amines such as the morpholine and piperidine salts.

In one embodiment, the invention provides a soft chewable veterinary composition comprising an effective amount of at least one isoxazoline compound of formula (I) below in combination with a pharmaceutically or veterinarily acceptable carrier:

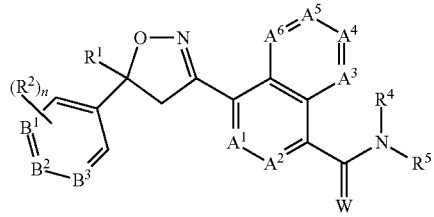
(I)

wherein
$A^1$, $A^2$, $A^3$, $A^4$, $A^5$ and $A^6$ are independently $CR^3$ or N, provided that at most 3 of $A^1$, $A^2$, $A^3$, $A^4$, $A^5$ and $A^6$ are N;
$B^1$, $B^2$ and $B^3$ are independently $CR^2$ or N;
W is O or S;
$R^1$ is alkyl, alkenyl, alkynyl, cycloalkyl, alkylcycloalkyl or cycloalkylalkyl, each optionally substituted with one or more substituents independently selected from $R^6$;

each $R^2$ is independently H, halogen, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —CN or —$NO_2$;
each $R^3$ is independently H, halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN or —$NO_2$;
$R^4$ is H, alkyl, alkenyl, alkynyl, cycloalkyl, alkylcycloalkyl, cycloalkylalkyl, alkylcarbonyl or alkoxycarbonyl;
$R^5$ is H, $OR^{10}$, $NR^{11}R^{12}$ or $Q^1$; or alkyl, alkenyl, alkynyl, cycloalkyl, alkylcycloalkyl or cycloalkylalkyl, each optionally substituted with one or more substituents independently selected from $R^7$; or
$R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;
each $R^6$ is independently halogen, alkyl, alkoxy, alkylthio, alkylsulfinyl, alkylsulfonyl, —CN or —$NO_2$;
each $R^7$ is independently halogen; alkyl, cycloalkyl, alkoxy, alkylthio, alkylsulfinyl, alkylsulfonyl, alkylamino, dialkylamino, cycloalkylamino, alkylcarbonyl, alkoxycarbonyl, alkylaminocarbonyl, dialkylaminocarbonyl, haloalkylcarbonyl, halo alkoxycarbonyl, haloalkylaminocarbonyl, dihaloalkylaminocarbonyl, hydroxy, —$NH_2$, —CN or —$NO_2$; or $Q^2$;
each $R^8$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —CN or —$NO_2$;
each $R^9$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN or —$NO_2$, phenyl or pyridinyl;
$R^{10}$ is H; or alkyl, alkenyl, alkynyl, cycloalkyl, alkylcycloalkyl or cycloalkylalkyl, each optionally substituted with one of more halogen;
$R^{11}$ is H, alkyl, alkenyl, alkynyl, cycloalkyl, alkylcycloalkyl, cycloalkylalkyl, alkylcarbonyl or alkoxycarbonyl;
$R^{12}$ is H; $Q^3$; or alkyl, alkenyl, alkynyl, cycloalkyl, alkylcycloalkyl or cycloalkylalkyl, each optionally substituted with one or more substituents independently selected from $R^7$; or
$R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;
$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each Q² is independently a phenyl ring or a 5- or 6-membered heterocyclic ring, each ring optionally substituted with one or more substituents independently selected from R⁹;

Q³ is a phenyl ring or a 5- or 6-membered heterocyclic ring, each ring optionally substituted with one or more substituents independently selected from R⁹; and n is 0, 1 or 2.

In another embodiment, the invention provides soft chewable veterinary compositions comprising an effective amount of at least one isoxazoline of formula (I) in combination with a pharmaceutically or veterinarily acceptable carrier:

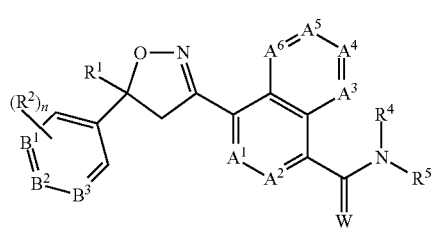

(I)

wherein:
A¹, A², A³, A⁴, A⁵ and A⁶ are independently CR³ or N, provided that at most 3 of A¹, A², A³, A⁴, A⁵ and A⁶ are N;
B¹, B² and B³ are independently CR² or N;
W is O or S;
R¹ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from R⁶;
each R² is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO₂;
each R³ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —NO₂;
R⁴ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
R⁵ is H, OR¹⁰, NR¹¹R¹² or Q¹; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from R⁷; or
R⁴ and R⁵ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO₂ and $C_1$-$C_2$ alkoxy;
each R⁶ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO₂;

each R⁷ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —NH₂, —CN or —NO₂; or Q²;
each R⁸ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or NO₂;
each R⁹ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO₂, phenyl or pyridinyl;
R¹⁰ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;
R¹¹ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
R¹² is H; Q³; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from R⁷; or
R¹¹ and R¹² are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO₂ and $C_1$-$C_2$ alkoxy;
Q¹ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from R⁸;
each Q² is independently a phenyl ring or a 5- or 6-membered heterocyclic ring, each ring optionally substituted with one or more substituents independently selected from R⁹;
Q³ is a phenyl ring or a 5- or 6-membered heterocyclic ring, each ring optionally substituted with one or more substituents independently selected from R⁹; and
n is 0, 1 or 2.

In one embodiment of formula (I), W is O. In another embodiment, W is S.

In another embodiment of formula (I), A¹, A², A³, A⁴, A⁵ and A⁶ are each CR³.

In another embodiment of formula (I), B¹, B² and B³ are each CR².

In still another embodiment of formula (I), W is O and A¹, A², A³, A⁴, A⁵ and A⁶ are each CR³.

In yet another embodiment of formula (I), W is O; A¹, A², A³, A⁴, A⁵ and A⁶ are each CR³; and B¹, B² and B³ are each CR².

In another embodiment of formula (I), A¹, A², A³, A⁴, A⁵ and A⁶ are each CH.

In another embodiment of formula (I), $B^1$, $B^2$ and $B^3$ are each $CR^2$; and $R^2$ is H, halogen, $C_1$-$C_6$ alkyl or $C_1$-$C_6$ haloalkyl.

In still another embodiment of formula (I), $R^1$ is $C_1$-$C_3$ alkyl optionally substituted by one or more of $R^6$;

$R^2$ is independently H, halogen, $C_1$-$C_6$ haloalkyl, $C_1$-$C_6$ haloalkoxy or —CN; and each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, —CN or —$NO_2$.

In still another embodiment, the invention provides a soft chewable veterinary composition comprising an isoxazoline of formula (I) wherein:

W is O or S; $R^4$ is H or $C_1$-$C_6$ alkyl; $R^5$ is —$CH_2C(O)NHCH_2CF_3$; each of $A^1=A^2=A^3=A^4=A^5=A^6$ is CH;

$R^1$ is $C_1$-$C_6$ alkyl each optionally substituted with one or more substituents independently selected from $R^6$;

$R^6$ is halogen or $C_1$-$C_6$ alkyl; and $B^1$, $B^2$, and $B^3$ are independently CH, C-halogen, C—$C_1$-$C_6$ alkyl, C—$C_1$-$C_6$haloalkyl, or C—$C_1$-$C_6$ alkoxy.

In another embodiment of formula (I), $B^1$, $B^2$ and $B^3$ are independently $CR^2$;

W is O;

$R^4$ is H, $C_1$-$C_6$ alkyl, $C_2$-$C_7$ alkylcarbonyl or $C_2$-$C_7$ alkoxycarbonyl; and $R^5$ is H, $NR^{11}R^{12}$ or $Q^1$; or $C_1$-$C_4$ alkyl, $C_2$-$C_4$ alkenyl, $C_2$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more of $R^7$.

In still another embodiment of formula (I), $R^1$ is $C_1$-$C_3$ alkyl optionally substituted with halogen;

each $R^2$ is independently H, $CF_3$, $OCF_3$, halogen or —CN;

each $R^3$ is independently H, $C_1$-$C_4$ alkyl, $C_1$-$C_4$ haloalkyl, $C_3$-$C_6$ cycloalkyl, $C_1$-$C_4$ alkoxy or —CN; and each $R^7$ is independently halogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkylcarbonyl, $C_2$-$C_4$ alkoxycarbonyl, $C_2$-$C_5$ alkylaminocarbonyl, $C_2$-$C_5$ haloalkylcarbonyl, $C_2$-$C_5$ haloalkoxycarbonyl, $C_2$-$C_5$ haloalkylaminocarbonyl, —$NH_2$, —CN or $NO_2$; or $Q_2$.

In yet another embodiment of formula (I), $R^4$ is H;

$R^5$ is $C_1$-$C_4$ alkyl optionally substituted with one or more $R^7$;

each $R^7$ is independently halogen or $Q^2$; and each $Q^2$ is independently phenyl, pyridinyl or thiazolyl.

In still another embodiment of formula (I), $R^1$ is $CF_3$;

$A^1$, $A^2$, $A^3$, $A^4$, $A^5$ and $A^6$ are each $CR^3$;

$B^2$ is $CR^2$; and each $R^3$ is independently H, $C_1$-$C_4$ alkyl or —CN.

In another embodiment, $B^2$ is CH;

$B^1$ and $B^3$ are each $CR^2$ where each $R^2$ is independently halogen or $C_1$-$C_3$ haloalkyl;

$A^1$, $A^2$, $A^3$, $A^4$, $A^5$ and $A^6$ are each $CR^3$;

$R^3$ is H; and n is 2.

In still another embodiment of formula (I), $R^1$ is $CF_3$;

$A^1$, $A^2$, $A^3$, $A^4$, $A^5$ and $A^6$ are each $CR^3$;

$B^2$ is CH;

each of $B^1$ and $B^3$ are $CR^2$;

each $R^3$ is independently H or $C_1$-$C_4$ alkyl;

each $R^2$ is independently halogen or $C_1$-$C_3$haloalkyl;

$R^4$ is H;

$R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl.

In yet another embodiment of formula (I), $R^1$ is $CF_3$;

$A^1$, $A^2$, $A^3$, $A^4$, $A^5$ and $A^6$ are each CH;

$B^2$ is CH;

each of $B^1$ and $B^3$ are $CR^2$;

each $R^2$ is independently halogen or $C_1$-$C_3$haloalkyl;

$R^4$ is H;

$R^5$ is $C_1$-$C_4$ alkyl optionally substituted with one or more $R^7$; and $R^7$ is $C_2$-$C_7$ alkylaminocarbonyl, $C_3$-$C_9$ dialkylaminocarbonyl, $C_2$-$C_7$ haloalkylaminocarbonyl or $C_3$-$C_9$ dihaloalkylaminocarbonyl.

In a preferred embodiment, a soft chewable veterinary composition comprising an isoxazoline active agent of formula (I) is provided, wherein:

$R^1$ is $CF_3$;

W is O;

$A^1$, $A^2$, $A^3$, $A^4$, $A^5$ and $A^6$ are each CH;

$B^2$ is CH;

$B^1$ is chloro;

$B^2$ is CF3;

$R^4$ is H;

$R^5$ is $CH_2C(O)NHCH_2CF_3$; and n is 2.

In one embodiment, the invention provides soft chewable veterinary compositions comprising an effective amount of the isoxazoline compound 1-4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (Compound A). This compound has the following structure:

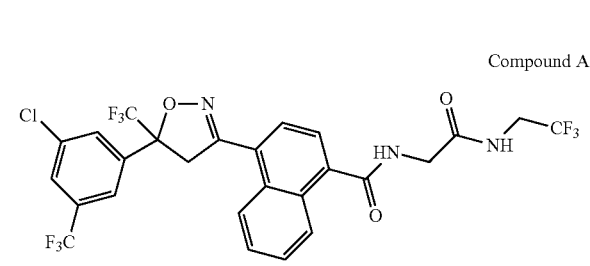 [SMILES: O=C(CNC(=O)c1ccc(C2=NOC(c3cc(Cl)cc(C(F)(F)F)c3)(C(F)(F)F)C2)c2ccccc12)NCC(F)(F)F]

Compound A

In other embodiments, the invention provides soft chewable veterinary compositions comprising an effective amount of an isoxazoline active agent described in WO 2009/02451A2 and US 2011/0059988, both incorporated herein by reference in their entirety, in combination with a pharmaceutically acceptable carrier or diluent. The compounds of general formula (II) shown below are described in US 2011/0059988 and WO 2009/02451 A2.

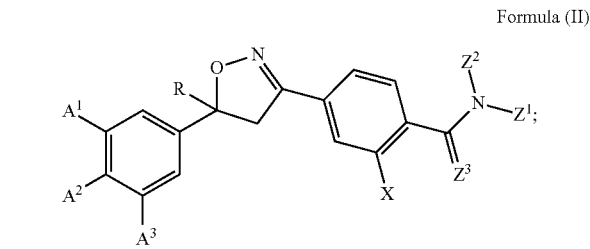

Formula (II)

In still another embodiment, the invention provides soft chewable veterinary compositions comprising an effective amount of compound 11-1 described in US 2011/0059988, which is referred to as Compound B herein and has the structure:

Compound B

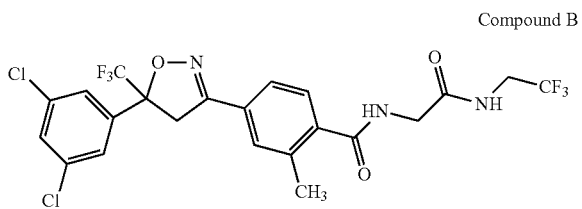 [SMILES: Cc1cc(C2=NOC(c3cc(Cl)cc(Cl)c3)(C(F)(F)F)C2)ccc1C(=O)NCC(=O)NCC(F)(F)F]

in combination with a pharmaceutically acceptable carrier or diluent described herein.

In yet another embodiment of the invention, the soft chewable veterinary compositions of the invention comprise an effective amount of a compound of formulae (III) or (IV) shown below, which are described in WO 2011/075591 and US 2011/0152312, both incorporated herein by reference in their entirety. In one embodiment, the isoxazoline has the structure of formula (III) or (IV), wherein:

$B_1$, $B_2$, $B_3$, $B_4$ and $B_5$ are independently N or C—$R_9$;

each Z is independently halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$R_{15}$ and $R_{16}$ are independently hydrogen, alkyl, haloalkyl, thioalkyl, alkylthioalkyl, hydroxyalkyl, alkoxylakyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$R_7$ and $R_8$ are independently hydrogen, alkyl, haloalkyl, thioalkyl, alkylthioalkyl, hydroxyalkyl, alkoxylakyl, alkenyl, haloalkenyl, alkynyl or haloalkynyl; and p is 1, 2 or 3.

In another embodiment the invention provides soft chewable veterinary compositions comprising an effective amount of at least one of compounds 1.001 to 1.025 or 2.001 to 2.018 described in WO 2011/075591 and US 2011/0152312 shown in Tables 1 and 2 below, in combination with a pharmaceutically acceptable carrier described herein:

Formula (III)

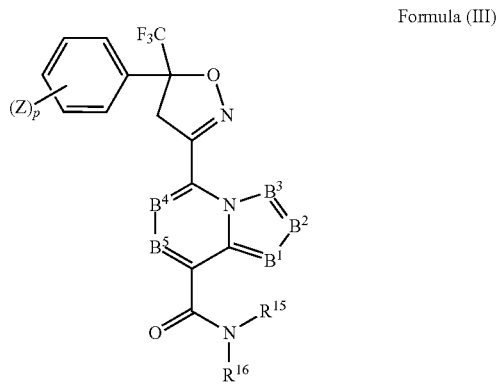

TABLE 1

Compounds 1.001 to 1.025

| Compound No. | $(Z)_p$ | $B^5$ | $B^4$ | $B^3$ | $B^2$ | $B^1$ | $R^{15}$ | $R^{16}$ | MS $MH^+$ | RT (min) | LCMS Method |
|---|---|---|---|---|---|---|---|---|---|---|---|
| 1.001 | 3,5-$Cl_2$ | C—H | C—H | C—H | C—H | N | H | $CH_2C(O)NHCH_2CF_3$ | 582 | 2.21 | 1 |
| 1.002 | 3,5-$Cl_2$ | C—H | C—H | C—H | C—H | N | H | $CH_2CF_3$ | 525 | 2.32 | 1 |
| 1.003 | 3,5-$(CF_3)_2$ | C—H | C—H | C—H | C—H | N | $CH_3$ | $CH_2CO_2CH_3$ | 597 | 2.06 | 1 |
| 1.004 | 3,5-$(CF_3)_2$ | C—H | C—H | C—H | C—H | N | $CH_3$ | $CH_2CO_2H$ | 583 | 2.07 | 1 |
| 1.005 | 3,5-$(CF_3)_2$ | C—H | C—H | C—H | C—H | N | $CH_3$ | $CH_2C(O)NHCH_2CF_3$ | 664 | 2.14 | 1 |
| 1.006 | 3,5-$(CF_3)_2$ | C—H | C—H | C—H | C—H | N | H | $CH_2C(O)NHCH_2CF_3$ | 650 | 2.18 | 1 |
| 1.007 | 3,5-$(CF_3)_2$ | C—H | C—H | C—H | C—H | N | H | $CH_2CH_2SCH_3$ | 585 | 2.31 | 1 |
| 1.008 | 3,5-$(CF_3)_2$ | C—H | C—H | C—H | C—H | C—H | H | $CH_2C(O)NHCH_2CF_3$ | 648 | 2.18 | 1 |
| 1.009 | 3,5-$(CF_3)_2$ | C—H | C—H | C—H | C—H | C—H | H | $CH_2CH_2SCH_3$ | 584 | 2.24 | 1 |
| 1.010 | 3,5-$(CF_3)_2$ | C—H | C—H | C—H | C—H | C—H | H | $CH_2CF_3$ | | | |
| 1.011 | 3,5-$Cl_2$ | C—H | C—H | C—H | C—H | C—H | H | $CH_2C(O)NHCH_2CF_3$ | 581 | 2.20 | 1 |
| 1.012 | 3,5-$Cl_2$ | C—H | C—H | C—H | C—H | C—H | H | $CH_2CF_3$ | | | |
| 1.013 | 3,5-$Cl_2$ | C—H | C—H | C—H | C—H | C—H | H | $CH_2CH_2SCH_3$ | 516 | 2.26 | 1 |
| 1.014 | 3-Cl,5-$CF_3$ | C—H | C—H | C—H | C—H | C—H | H | $CH_2C(O)NHCH_2CF_3$ | | | |
| 1.015 | 3-Cl,5-$CF_3$ | C—H | C—H | C—H | C—H | C—H | H | $CH_2CF_3$ | | | |
| 1.016 | 3-Cl,5-$CF_3$ | C—H | C—H | C—H | C—H | C—H | H | $CH_2CH_2SCH_3$ | | | |
| 1.017 | 3,5-$Cl_2$ | C—H | C—H | C—Me | C—H | C—Me | H | $CH_2C(O)NHCH_2CF_3$ | 609 | 2.12 | 1 |
| 1.018 | 3,5-$Cl_2$ | C—H | C—H | C—Me | C—H | C—Me | H | $CH_2CF_3$ | 552 | 2.17 | 1 |
| 1.019 | 3,5-$Cl_2$ | C—H | C—H | C—Me | C—H | C—Me | H | $CH_2CH_2SCH_3$ | 544 | 2.18 | 1 |
| 1.020 | 3,5-$(CF_3)_2$ | C—H | C—H | C—Me | C—H | C—Me | H | $CH_2C(O)NHCH_2CF_3$ | | | |
| 1.021 | 3,5-$(CF_3)_2$ | C—H | C—H | C—Me | C—H | C—Me | H | $CH_2CF_3$ | | | |
| 1.022 | 3,5-$(CF_3)_2$ | C—H | C—H | C—Me | C—H | C—Me | H | $CH_2CH_2SCH_3$ | | | |
| 1.023 | 3-Cl,5-$CF_3$ | C—H | C—H | C—Me | C—H | C—Me | H | $CH_2C(O)NHCH_2CF_3$ | | | |
| 1.024 | 3-Cl,5-$CF_3$ | C—H | C—H | C—Me | C—H | C—Me | H | $CH_2CF_3$ | | | |
| 1.025 | 3-Cl,5-$CF_3$ | C—H | C—H | C—Me | C—H | C—Me | H | $CH_2CH_2SCH_3$ | | | |

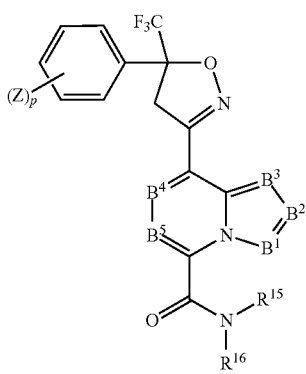

Formula (IV)

of administration. Furthermore, in some embodiments the compositions of the invention provide extremely long-lasting efficacy against ectoparasites and/or endoparasites that is unexpected and surprising from an immediate release oral dosage form.

In one embodiment, the soft chewable compositions of the invention provide exceptionally high bioavailability for systemically-acting isoxazoline active agents. The surprisingly high bioavailability of the isoxazoline active agents achieved from the compositions of the invention is a key factor in achieving the fast onset of action and the very long lasting efficacy against ectoparasites observed.

In order for the compositions of the invention to be efficacious against ectoparasites such as ticks and fleas for an extended period of time, the isoxazoline active agent must be present at a minimally effective concentration in the plasma and/or tissues of the animal for the desired period of time. The

TABLE 2

Compounds 2.001 to 2.018

| Compound No. | $(Z)_p$ | $B^5$ | $B^4$ | $B^3$ | $B^2$ | $B^1$ | $R^{15}$ | $R^{16}$ | MS $MH^+$ | RT (min) | LCMS Method |
|---|---|---|---|---|---|---|---|---|---|---|---|
| 2.001 | 3,5-$Cl_2$ | C—H | C—H | N | | C—H | C—H | H | $CH_2C(O)NHCH_2CF_3$ | | | |
| 2.002 | 3,5-$Cl_2$ | C—H | C—H | N | | C—H | C—H | H | $CH_2CF_3$ | | | |
| 2.003 | 3,5-$Cl_2$ | C—H | C—H | N | | C—H | C—H | H | $CH_2CH_2SCH_3$ | | | |
| 2.004 | 3,5-$(CF_3)_2$ | C—H | C—H | N | | C—H | C—H | H | $CH_2C(O)NHCH_2CF_3$ | 650 | 1.85 | 1 |
| 2.005 | 3,5-$(CF_3)_2$ | C—H | C—H | N | | C—H | C—H | H | $CH_2CF_3$ | | | |
| 2.006 | 3,5-$(CF_3)_2$ | C—H | C—H | N | | C—H | C—H | H | $CH_2CH_2SCH_3$ | | | |
| 2.007 | 3-Cl,5-$CF_3$ | C—H | C—H | N | | C—H | C—H | H | $CH_2C(O)NHCH_2CF_3$ | | | |
| 2.008 | 3-Cl,5-$CF_3$ | C—H | C—H | N | | C—H | C—H | H | $CH_2CF_3$ | | | |
| 2.009 | 3-Cl,5-$CF_3$ | C—H | C—H | N | | C—H | C—H | H | $CH_2CH_2SCH_3$ | | | |
| 2.010 | 3,5-$Cl_2$ | C—H | C—H | C—H | C—H | C—H | H | $CH_2C(O)NHCH_2CF_3$ | | | |
| 2.011 | 3,5-$Cl_2$ | C—H | C—H | C—H | C—H | C—H | H | $CH_2CF_3$ | | | |
| 2.012 | 3,5-$Cl_2$ | C—H | C—H | C—H | C—H | C—H | H | $CH_2CH_2SCH_3$ | | | |
| 2.013 | 3,5-$(CF_3)_2$ | C—H | C—H | C—H | C—H | C—H | H | $CH_2C(O)NHCH_2CF_3$ | | | |
| 2.014 | 3,5-$(CF_3)_2$ | C—H | C—H | C—H | C—H | C—H | H | $CH_2CF_3$ | | | |
| 2.015 | 3,5-$(CF_3)_2$ | C—H | C—H | C—H | C—H | C—H | H | $CH_2CH_2SCH_3$ | | | |
| 2.016 | 3-Cl,5-$CF_3$ | C—H | C—H | C—H | C—H | C—H | H | $CH_2C(O)NHCH_2CF_3$ | | | |
| 2.017 | 3-Cl,5-$CF_3$ | C—H | C—H | C—H | C—H | C—H | H | $CH_2CF_3$ | | | |
| 2.018 | 3-Cl,5-$CF_3$ | C—H | C—H | C—H | C—H | C—H | H | $CH_2CH_2SCH_3$ | | | |

In another embodiment, the soft chewable veterinary compositions of the invention may include one or more compounds of the isoxazolines disclosed in US 2010/0254960 A1, US2011/0159107, US2012/0309620, US2012/0030841, US2010/0069247, WO 2007/125984, WO 2012/086462, U.S. Pat. No. 8,318,757, US 2011/0144349, U.S. Pat. No. 8,053,452; US 2010/0137612, US 2010/0254959, US 2011/152081, WO 2012/089623, WO 2012/089622, U.S. Pat. No. 8,119,671; U.S. Pat. No. 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, US7951828 & US7662972, US 2010/0137372 A1, US 2010/0179194 A2, US 2011/0086886 A2, US 2011/0059988 A1, US 2010/0179195 A1, U.S. Pat. No. 7,897,630, U.S. Pat. No. 7,951,828 and U.S. Pat. No. 7,662,972, all of which are incorporated herein by reference in their entirety.

Bioavailability of Active Agents

It has been surprisingly found that the compositions of the invention provide exceptionally high bioavailability for the systemically-acting active agents in the blood of the animal to which the compositions are administered within a few hours time that the active agent remains in the systemic circulation (measured as half-life or $T_{1/2}$, the period of time it takes for the amount of active agent undergoing decay to decrease by half) is based on the intrinsic structure of the compound and how it behaves in vivo. However, the amount of the active agent that is absorbed into the systemic circulation from an oral dosage form may be significantly affected by the non-active excipients of the composition. As such, the specific combination of non-active excipients in a composition can have a major effect on the bioavailability of a given active agent.

In order for an active ingredient to be readily bioavailable and absorbed from the gastrointestinal lumen into the bloodstream of the animal, the active agent must first be effectively released from the solid composition after ingestion. Secondly, in the case of active agents with low water solubility, the active agent must be maintained in solution at the appropriate location in the gastrointestinal lumen to be absorbed across the intestinal epithelium and into the bloodstream. Both of these factors can be significantly affected by the combination of non-active excipients in the oral dosage forms.

It is well known that one of the drawbacks of oral dosage forms is that the amount of the drug that can be absorbed from the digestive tract into the systemic circulation is limited. In fact, it is well established in the literature that low bioavailability is one of the leading causes of new drug candidate failures in pre-clinical and clinical development, especially for compounds with low aqueous solubility. Compounds that achieve poor bioavailability tend to have low plasma exposure and high variability between subjects, limiting their therapeutic usefulness (see V. Hayden et al. The Road Map to Oral Bioavailability: an Industrial Perspective, *Expert Opin. Drug Metab. Toxicol.* 2006, 2(4):591-608). Poor bioavailability limits the choice of drugs for oral administration, and in other cases significant allowances must be made to account for the low absorption of the active agent. This is reflected in the established minimal acceptable oral bioavailability of only 30% for typical oral dosage drug development programs (V. Hayden et al., Ibid.). Further, a number of well-known human drugs are known to have bioavailabilities of ≤20% (see Fasinu et al., *Biopharm. Drug Dispos.* 2011, 32, 1185-209).

In one embodiment, the compositions of the invention comprising at least one isoxazoline active agent have exceptionally consistent and predictable dissolution profiles in vitro over a range of dosage form sizes, releasing a high percentage of the isoxazoline active ingredient. In an embodiment, the compositions of the invention release at least about 70% (w/w) of the available isoxazoline active ingredient within 60 minutes, as measured by a standard dissolution test. In other embodiments, the compositions of the invention release at least about 80% (w/w) of the available isoxazoline active agent within about 60 minutes. In still another embodiment, the compositions of the invention release at least about 85% (w/w) or about 90% (w/w) of the available isoxazoline active agent within about 60 minutes. The predictable and consistent dissolution profiles exhibited by the compositions of the invention are unusual for chewable compositions and are indicative of the excellent bioavailability in vivo.

FIGS. 1 and 2 show the dissolution profiles of 2 gram soft chewable compositions of the invention that have been stored at 25° C. and 60% relative humidity (RH) and 40° C. and 75% RH, respectively, taken at 1, 2, 3, 6 and 12 months. FIGS. 3 and 4 show the dissolution profiles of 4 gram soft chewable compositions of the invention that have been stored at 25° C. and 60% relative humidity (RH) and 40° C. and 75% RH, respectively, taken at 0, 2 and 6 months. As the figures show, both the 2 gram and 4 gram size soft chewable compositions exhibit extremely reproducible dissolution profiles, even after storage at accelerated stability conditions. This demonstrates the predictable and consistent release profile of the compositions of the invention, which is an important factor in obtaining the surprising and unexpected bioavailability observed.

Consistent with the predictable and efficient dissolution profile exhibited in vitro, animals treated with the compositions of the invention absorb a very high proportion of the isoxazoline active agent in vivo after administration. Thus in one embodiment, the compositions of the invention provide a maximum drug concentration in plasma after as little as about 3 hours after administration. In other embodiments, the compositions of the invention provide a maximum concentration of the drug after about 3 and a half hours or after about 4 hours after administration. In still other embodiments, the compositions of the invention provide a maximum concentration of the isoxazoline in the plasma after about 4 and a half or about 5 hours after administration.

The compositions of the invention comprising at least one isoxazoline active agent exhibit surprisingly high bioavailability of the isoxazoline active agent in vivo. Thus, in one embodiment, the soft chewable veterinary compositions of the invention provide at least about 70% bioavailability of the isoxazoline active agent relative to intravenous dosing. In other embodiments of the invention, the soft chewable compositions provide at least about 85% or at least about 95% bioavailability of the isoxazoline active agent after administration. In some embodiments, the bioavailability of the isoxazoline active agent from the inventive chewable compositions is even up to about 100% relative to intravenous administration of the active agent.

These levels of bioavailability of an isoxazoline active agent having low water solubility from a soft chewable veterinary composition are surprisingly high and unexpected. Although the extremely high bioavailability of the chewable compositions is in part due to the physico-chemical properties of the isoxazoline active agents, the high levels observed from the chewable compositions of the invention are made possible by the presence and combination of the non-active excipients, which ensure complete and predictable dissolution of the composition and maintain the active agents in solution in the digestive tract of the animal. The significant effect of the non-active excipients of the compositions of the invention on the bioavailability of the isoxazoline active agent is demonstrated by FIG. 5. This plot compares the plasma concentration of an isoxazoline active agent (Compound A) delivered from soft chewable compositions of the invention designed to deliver 20 mg/kg and 40 mg/kg of body weight with administration of a polyethylene glycol/alcohol solution of the active agent at 25 mg/kg body weight. The figure shows that the soft chewable compositions of the invention provide significantly higher plasma levels even when dosed at lower levels compared to a solution of the active agent (20 mg/kg chewable composition vs. 25 mg/kg solution). This is particularly surprising since the chewable compositions are in the form of a solid that must disintegrate and completely release and solubilize the active agent for efficient absorption during digestion. One would expect the solution to provide higher bioavailability because the active agent is completely dissolved when administered. The significantly higher bioavailability achieved from the chewable compositions of the invention is clearly the result of the non-active excipients in the composition rather than the natural permeability of the active agent since the same active is used.

The surprisingly high bioavailability of the isoxazoline active agents in the oral veterinary compositions of the invention significantly contributes to the fast onset of action and the extremely long lasting efficacy against fleas and ticks. Thus, in some embodiments, the ability of the compositions to safely and predictably achieve a desired concentration of the isoxazoline active agent in the blood stream without having to dose very high levels of the compound to the animal coupled with the residence time of the active agent in the blood stream results in superior control of ectoparasites, including for up to about 90 days or longer against fleas. This length of efficacy from a once-dosed immediate release oral dosage form is unparalleled and very surprising.

In another embodiment, the soft chewable compositions of the invention may provide exceptionally high and unexpected bioavailability of parasiticidal active agents that are active against endoparasites. Thus, in one embodiment, the soft chewable compositions of the invention may provide a bioavailability of at least about 70% relative to intravenous dosing of a parasiticide selected from the group consisting of a macrocyclic lactone active agent, a benzimidazole agent including thiabendazole, oxibendazole, mebendazole, fenbendazole, oxfendazole, albendazole, triclabendazole and febantel; levamisole, pyrantel, morantel, closantel, clorsulon, an amino acetonitrile active agent and an aryloazol-2-yl cyanoethylamino active agent. In another embodiment, the soft chewable compositions of the invention may provide a bioavailability of at least about 80%, at least about 85% or at least about 90% relative to intravenous dosing of a parasiticide selected from a macrocyclic lactone active agent, a benzimidazole agent including thiabendazole, oxibendazole, mebendazole, fenbendazole, oxfendazole, albendazole, triclabendazole and febantel; levamisole, pyrantel, morantel, closantel, clorsulon, an amino acetonitrile active agent and an aryloazol-2-yl cyanoethylamino active agent.

Ectoparasiticidal Compositions

The soft chewable veterinary compositions of the invention, which include at least one isoxazoline active agent and a pharmaceutically acceptable carrier that is suitable for oral administration to an animal, have been surprisingly discovered to be safe and effective against a broad spectrum of ectoparasites for an extended period of time. For example, in one embodiment of the invention, the soft chewable compositions of the invention provide protection of at least 90% efficacy against fleas (*C. felis*) for at least 30 days or at least 36 days as measured against untreated controls according to the methods described in the examples. In another embodiment, the soft chewable compositions of the invention provide at least 90% efficacy against fleas for at least 44 days or for at least 58 days.

In some embodiments of the invention, the compositions of the invention comprising at least one isoxazoline active provide a high level of efficacy against fleas for periods of time in excess of 60 days. For example, in one embodiment, the compositions of the invention provide an efficacy of at least 90% against fleas for at least 72 days. In other embodiments, the compositions of the invention provide an efficacy of at least 90% against fleas for at least 79 days, at least 86 days or even at least 93 days. In still other embodiments, the very long lasting oral compositions of the invention provide an efficacy of at least 90% against fleas for at least about 100 days, at least about 107 days or even at least about 114 days.

In yet another embodiment, the soft chewable veterinary compositions of the invention comprising at least one isoxazoline active provide an efficacy of at least about 95% against fleas (*C. felis*) for at least about 30 days or at least about 36 days. In yet another embodiment, the soft chewable veterinary compositions of the invention provide an efficacy of at least about 95% for at least about 44 days, at least about 58 days or at least about 72 days. In still other embodiments, the very long lasting oral compositions of the invention provide an efficacy of at least about 95% for at least about 79 days, at least about 86 days or even about 93 days.

In yet another embodiment of the invention, the soft chewable compositions comprising an effective amount of at least one isoxazoline active agent provide about 100% efficacy against fleas for at least about 23 days, at least about 30 days or at least about 36 days. In still other embodiments, the compositions of the invention provide an efficacy of about 100% against fleas for at least about 44 days, at least about 58 days or at least about 72 days.

In another embodiment of the invention, the soft chewable veterinary compositions comprising an isoxazoline active agent provide an efficacy of at least about 90% against ticks (including, but not limited to, *Dermacentor variabilis, Ixodes scapularis, Amblyomma americanum, Rhipicephalus sanguineus, Ixodes ricinus, Dermacentor reticulatus* and *Ixodes holocyclus*) for at least about 30 days or at least about 36 days. In still another embodiment, the soft chewable veterinary compositions of the invention will provide an efficacy of at least about 95% for at least about 23 days, at least about 30 days or at least about 36 days.

In some embodiments, the very long lasting oral veterinary compositions of the invention comprising at least one isoxazoline active provide an efficacy against certain species of ticks of at least about 90% for at least about 44 days, at least about 58 days, or at least about 72 days. In other embodiments, the oral veterinary compositions of the invention provide an efficacy against certain species of ticks of at least about 90% for at least about 79 days, at least about 86 days, at least about 93 days, at least about 100 days or even at least about 107 days. In some embodiments, the oral compositions of the invention provide an efficacy of at least about 95% against ticks for at least about 44 days, at least about 58 days, at least about 72 days or at least about 79 days. In certain other embodiments, the compositions of the invention will provide an efficacy of at least 95% for at least about 100 days or even at least about 107 days against certain species of ticks (e.g. *D. variabilis*). In other embodiments, the compositions of the invention will even provide an efficacy of about 100% against certain species of ticks for at least about 93 days, at least about 100 days or even at least about 107 days. This very high level of efficacy against ticks for such extended periods of time from an oral dosage form is striking and without precedence in immediate release oral dosage forms. Furthermore, the oral compositions of the invention are surprisingly effective against hard to control ticks including *Amblyomma americanum* and others.

The soft chewable veterinary compositions of the invention comprising at least one isoxazoline active agent have been found to exhibit a very fast onset of action against parasites that harm animals. For example, in some embodiments of the invention, the soft chewable veterinary compositions of the invention provide an efficacy of at least about 15%, at least about 20% or at least about 30% against fleas (*C. felis*) only about 30 minutes after administration to the animal compared with untreated controls, as measured according to the methods described in the examples.

In other embodiments, the soft chewable compositions of the invention provide an efficacy of at least about 30%, at least about 40% or at least about 50% against fleas only about 4 hours after administration. In still other embodiments, the compositions of the invention provide an efficacy of at least about 50%, at least about 60% or at least about 70% against fleas about 8 hours after administration to the animal. In yet other embodiments, the compositions of the invention provide an efficacy of at least about 85%, at least about 90%, at least about 95% or at least about 98% about 12 hours after administration of the composition to the animal. This surprisingly fast onset of efficacy is very important for effectively treating animals with established severe ectoparasitic infestations.

Typically, the isoxazoline(s) active agents may be present in the composition at a concentration of about 0.1 to about 40% (w/w). In another embodiment, the concentration of the isoxazoline(s) active agents is about 0.1 to about 30% (w/w). In some embodiments of the invention, the isoxazoline active agents are present in the composition at a concentration from about 1 to about 25% (w/w), about 1 to about 20% (w/w), about 1 to about 10% (w/w), about 1 to about 5% (w/w), or about 1 to about 3% (w/w). In still other embodiments, the isoxazoline(s) active agents are present in a concentration of about 0.1 to about 5% (w/w), about 0.5 to about 5% (w/w), about 0.5 to about 3% (w/w) or about 1 to about 3% (w/w) in the composition. In yet other embodiments, the isoxazoline(s) active agents are present in a concentration of about 3 to about 6% (w/w), or about 5 to 10% (w/w). In other embodiments, the isoxazoline active agent is present in a relatively higher concentration in the dosage form, including about 5%

(w/w) to about 15% (w/w), about 10% (w/w) to about 20% (w/w), about 10% (w/w) to about 15% (w/w) or about 15% (w/w) to about 20% (w/w) in the composition.

Some dosage units may contain from about 0.5 mg to about 2000 mg of at least one isoxazoline active agent or a combination of isoxazoline active agents. In one embodiment, the isoxazoline active is present in an amount of from about 1 mg to about 200 mg in the composition. More typically, the isoxazoline active agent is present in an amount of about 1 mg to about 150 mg or about 10 mg to about 150 mg per chewable unit. In some embodiments, the amount of at least one isoxazoline active agent in a dosage unit is about 5 mg to about 50 mg, bout 1 mg to about 30 mg, or about 5 mg to about 30 mg. In other embodiments, the amount of at least one isoxazoline active agent in a dosage unit of the invention is about 1 mg to about 20 mg or about 1 mg to about 15 mg. In other embodiments, the dosage units will contain about 50 mg to about 150 mg, about 50 mg to about 100 mg, or about 75 mg to about 140 mg of at least one isoxazoline active agent.

In other embodiments, the amount of at least one isoxazoline active agent will be about 100 mg to about 2000 mg per dosage unit. More typically, the amount of at least one isoxazoline active agent in a dosage unit will be about 100 mg to about 1500 mg, about 100 mg to about 1000 mg or about 500 mg to about 1200 mg per dosage unit.

Additional Active Agents

In another aspect of the invention, oral veterinary compositions, including soft chewable compositions and chewable tablet compositions, that comprise one or more additional systemically-acting parasiticidal active agents are provided. The active agents that may be included in the composition can be from various classes of systemically-acting parasiticides and may be included in the oral veterinary compositions of the invention alone or in combination with an isoxazoline active agent and/or other systemically-acting ectoparasiticides including, but not limited to, one or more spinosyn or spinosoid, one or more insect growth regulators, one or more arylpyrazoles and one or more neonicotinoids. When the compositions comprise a combination of a systemically-acting endoparasiticidal agent in combination with an ectoparasiticidal agent including, but not limited to, an isoxazoline active agent, the compositions will be effective against both endoparasitic and ectoparasitic infections and infestations.

In one embodiment, the invention provides a soft chewable veterinary composition comprising at least one isoxazoline active agent in combination with at least one other systemically-acting active agent that is active against endoparasites, and a pharmaceutically acceptable carrier or diluent. In another embodiment, the invention provides a soft chewable veterinary composition comprising at least one isoxazoline active agent in combination with at least one systemically-acting active agent that is active against ectoparasites, together with a pharmaceutically acceptable carrier or diluent.

In some embodiments, the additional active agents combined with an isoxazoline active agent may include, but are not limited to, acaricides, anthelmintics, insecticides and other parasiticides of various classes presented herein.

In another embodiment, the soft chewable compositions may also include veterinary therapeutic agents. Veterinary pharmaceutical agents that may be included in the compositions of the invention are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/- clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *propionibacterium* acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles may be included in the oral veterinary compositions of the invention. The arylpyrazoles are known in the art and are suitable for combination with the isoxazoline compounds in the soft chewable compositions of the invention. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil. In one embodiment, the arylpyrazole may be included in the soft chewable compositions in combination with one or more isoxazoline active agents, one or more macrocyclic lactones, one or more spinosyn compounds, one or more spinosoid compounds, a benzimidazole, levamisole, pyrantel, morantel, praziquantel, closantel, clorsulon, one or more amino acetonitrile active agent, one or more insect growth regulators, one or more neonicotinoids or one or more aryloazol-2-yl cyanoethylamino active agents, or a combination of thereof.

In another embodiment of the invention, one or more macrocyclic lactones or lactams, which act as an acaricide, an anthelmintic agent and/or an insecticide, can be included in the compositions of the invention. The macrocyclic lactone active agents are very potent and may be included alone in the compositions or in combination with one or more isoxazoline active agents, one or more spinosyn compounds, one or more spinosoid compounds, a benzimidazole, levamisole, pyrantel, morantel, praziquantel, closantel, clorsulon, one or more amino acetonitrile active agent, one or more insect growth regulators, one or more neonicotinoids or one or more aryloazol-2-yl cyanoethylamino active agents, or a combination of thereof. Furthermore, in one embodiment, the oral veterinary compositions of the invention may comprise a combination of two or more macrocyclic lactone active agents, alone or in combination with other systemically-acting active agents. For the avoidance of doubt, the term "macrocyclic lactone" as used herein includes both naturally occurring and synthetic or semi-synthetic avermectin and milbemycin compounds.

The macrocyclic lactones that may be used in the compositions of the invention include, but are not limited to, the naturally produced avermectins (e.g. including the components designated as $A_1a$, $A_1b$, $A_2a$, $A_1b$, $B_1a$, $B_1b$, $B_2a$ and $B_2b$) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" $12^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In one embodiment, the oral veterinary compositions of the invention, including soft chewable compositions and chewable tablet compositions, comprise an effective amount of at least one of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the invention provides a soft chewable veterinary composition comprising an effective amount of at least one of abamectin, emamectin, eprinomectin, ivermectin, doramectin or selamectin, or a combination thereof. In still another embodiment, the soft chewable veterinary compositions of the invention comprise an effective amount of at least one of ivermectin, milbemectin, milbemycin oxime or moxidectin, or a combination thereof.

In another embodiment, oral veterinary compositions comprising at least one isoxazoline active agent in combination with abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof, are provided. In still another embodiment, oral veterinary compositions comprising at least one isoxazoline active agent in combination with abamectin, emamectin, eprinomectin, ivermectin, doramectin or selamectin, or a combination thereof, are provided.

In yet another embodiment, soft chewable veterinary compositions comprising at least one isoxazoline active agent of formula (I), formula (II), formula (III) or formula (IV) in combination with an effective amount of ivermectin, milbemectin, milbemycin oxime or moxidectin, or a combination thereof, are provided.

In another embodiment, the invention provides a soft chewable veterinary composition comprising an effective amount of at least one of Compound A, Compound B, Compound 1.001 to 1.025 or Compound 2.001 to 2.018 in combination with an effective amount of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the invention provides a soft chewable veterinary composition comprising an effective amount of at least one of Compound A, Compound B, Compound 1.001 to 1.025 or Compound 2.001 to 2.018 in combination with an effective amount of abamectin, emamectin, eprinomectin, ivermectin, doramectin or selamectin, or a combination thereof. In still another embodiment, the invention provides a soft chewable veterinary composition comprising an effective amount of at least one of Compound A, Compound B, Compound 1.001 to 1.025 or Compound 2.001 to 2.018 in combination with an effective amount of at least one of ivermectin, milbemectin, milbemycin D, milbemycin $A_3$, milbemycin $A_4$, milbemycin oxime, moxidectin or nemadectin, or a combination thereof.

In some embodiments, the chewable veterinary compositions may comprise a combination of at least one isoxazoline active agent with two different macrocyclic lactone active agents.

In still another embodiment, the invention provides a soft chewable veterinary composition comprising an effective amount of Compound A in combination with an effective amount of abamectin, emamectin, eprinomectin, ivermectin or selamectin, or a combination thereof. In yet another embodiment, the invention provides a soft chewable veterinary composition comprising an effective amount of Compound A in combination with an effective amount of ivermectin, milbemycin oxime or moxidectin, or a combination thereof.

In another embodiment of the invention, a composition comprising a class of acaricides or insecticides known as insect growth regulators (IGRs) are provided. The IGR active agents may be included in the oral veterinary compositions of the invention. The IGR active agents may be included in the composition alone, or in combination with at least one isoxazoline active agent or another systemically-acting active agent described herein including, but not limited to, one or more macrocyclic lactones, one or more spinosyn compounds, one or more spinosoid compounds, a benzimidazole, levamisole, pyrantel, morantel, praziquantel, closantel, clorsulon, one or more amino acetonitrile active agent, one or more insect growth regulators, one or more neonicotinoids or one or more aryloazol-2-yl cyanoethylamino active agents, or a combination of thereof. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751, 225, EP 0 179 022 or U.K. 2 140 010 as well as U.S. Pat. Nos. 6,096,329 and 6,685,954 (all incorporated herein by reference).

In one embodiment the compositions of the invention may include an IGR compound that mimics juvenile hormone or that modulates levels of juvenile hormones in insects. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one. In another embodiment, the compositions of the invention comprise an isoxazoline compound in combination with methoprene or pyriproxyfen and a pharmaceutically acceptable carrier.

In another embodiment, the compositions of the invention include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In some embodiments, the compositions of the invention may include one or more antinematodal agents including, but not limited to, active agents in the benzimidazoles, imidazothiazoles, tetrahydropyrimidines and the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions. The aforementioned active agents may be included in the compositions alone or in combination with other systemically-acting parasiticides described herein including, but not limited to, one or more isoxazoline active agents, one or more macrocyclic lactone active agents, one or more spinosyn or spinosoid compounds, levamisole, pyrantel, morantel, praziquantel, closantel, clorsulon, one or more amino acetonitrile active agents, one or more insect growth regulators, one or more neonicotinoids or one or more aryloazol-2-yl cyanoethylamino active agents, or a combination thereof.

In other embodiments, the compositions may include an imidazothiazole compounds including, but not limited to, tetramisole, levamisole and butamisole, alone or in combination with one or more systemically-active active agents described herein including, but not limited to, one or more isoxazoline active agents, one or more macrocyclic lactone active agents, one or more spinosyn or spinosoid compounds, one or more benzimidazole agents including thiabendazole, oxibendazole, mebendazole, fenbendazole, oxfendazole, albendazole, triclabendazole and febantel; pyrantel, morantel, praziquantel, closantel, clorsulon, one or more amino acetonitrile active agents, one or more insect growth regulators, one or more neonicotinoids and one or more aryloazol-2-yl cyanoethylamino active agents, or a combination thereof.

In still other embodiments, the compositions of the invention may include tetrahydropyrimidine active agents including, but not limited to, pyrantel, oxantel, and morantel, alone or in combination with one or more systemically-acting active agents including, but not limited to, one or more isoxazoline active agents, one or more macrocyclic lactone active agents, one or more spinosyn or spinosoid compounds, one or more benzimidazole agents including thiabendazole, oxibendazole, mebendazole, fenbendazole, oxfendazole, albendazole, triclabendazole and febantel; levamisole, praziquantel, closantel, clorsulon, one or more amino acetonitrile active agents, one or more insect growth regulators, one or more neonicotinoids and one or more aryloazol-2-yl cyanoethylamino active agents, or a combination thereof.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid. These antinematodal active agents may be included in the compositions alone or in combination one or more of the systemically-acting parasiticides described herein.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, nitroxynil, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin, paromomycin II, praziquantel and epsiprantel.

The antinematodal, antitrematodal and anticestodal active agents described above may be included in the compositions alone or in combination with one or more of the systemically-acting active agents described herein including, but not limited to, one or more isoxazoline active agents, one or more macrocyclic lactone active agents, one or more spinosyn or spinosoid active agents, one or more benzimidazole agents including thiabendazole, oxibendazole, mebendazole, fenbendazole, oxfendazole, albendazole and febantel; levamisole, pyrantel, morantel, one or more amino acetonitrile active agent, one or more insect growth regulators, one or more neonicotinoids and one or more aryloazol-2-yl cyanoethylamino active agents, or a combination thereof.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfuram, isobornyl thiocyanato acetate, methoprene, monosulfuram, pirenonylbutoxide, rotenone, triphenyltin acetate, triphenyltin hydroxide, deet, dimethyl phthalate, and the compounds 1,5a,6,9,9a,9b-hexahydro-4-a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

In another embodiment, an antiparasitic agent that can be included in the soft chewable veterinary composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Wilson et al., *Parasitology*, January 2003, 126(Pt 1):79-86).

In another embodiment, the compositions of the invention may comprise an active agent from the neonicotinoid class of parasiticides. The neonicotinoids bind and inhibit insect specific nicotinic acetylcholine receptors. In one embodiment, the neonicotinoid insecticidal agent that can be combined with an isoxazoline compound to form a topical composition of the invention is imidacloprid. Agents of this class are described, for example, in U.S. Pat. No. 4,742,060 or in EP 0 892 060 (both incorporated herein by reference). In another embodiment, the compositions of the invention may comprise nitenpyram, another active agent of the neonicotinoid class of pesticides. The use of nitenpyram for controlling fleas is described in U.S. Pat. No. 5,750,548, which is incorporated herein by reference in its entirety. The neonicotinoid active agents may be included in the compositions alone, or in combination with one or more of the other systemically-acting active agents described herein including, but not limited to, one or more isoxazoline active agents, one or more macrocyclic lactone active agents, one or more spinosyn or spinosoid active agents, one or more benzimidazole agents including thiabendazole, oxibendazole, mebendazole, fenbendazole, oxfendazole, albendazole, triclabendazole and febantel; levamisole, pyrantel, morantel, praziquantel, closantel, clorsulon, one or more amino acetonitrile active agents, one or more insect growth regulators and one or more aryloazol-2-yl cyanoethylamino active agents, or a combination thereof. In another embodiment, the soft chewable compositions of the invention comprise the isoxazoline Compound A in combination with nitenpyram and/or imidacloprid.

In other certain embodiments of the invention, an insecticidal agent that can be combined with the compositions of the invention is a semicarbazone, such as metaflumizone.

In another embodiment, the compositions of the invention may advantageously include a mixture of one or more other isoxazoline compounds known in the art, in addition to or in place of the isoxazoline active agents described above. These active agents are described in US 2010/0254960 A1, US2011/0159107, US2012/0309620, US2012/0030841, US2010/0069247, WO 2007/125984, WO 2012/086462, U.S. Pat. No. 8,318,757, US 2011/0144349, U.S. Pat. No. 8,053,452; US 2010/0137612, US 2010/0254959, US 2011/152081, WO 2012/089623, WO 2012/089622, U.S. Pat. No. 8,119,671; U.S. Pat. No. 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, US7951828 & US7662972, US 2010/0137372 A1, US 2010/0179194 A2, US 2011/0086886 A2, US 2011/0059988 A1, US 2010/0179195 A1, U.S. Pat. No. 7,897,630, U.S. Pat. No. 7,951,828 and U.S. Pat. No. 7,662,972, all of which are incorporated herein by reference in their entirety.

In another embodiment of the invention, nodulisporic acid and its derivatives may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in U.S. Pat. No. 7,084,280 to Ducray et al. (incorporated herein by reference); Sager et al., Veterinary Parasitology, 2009, 159, 49-54; Kaminsky et al., Nature vol. 452, 13 Mar. 2008, 176-181. The AAD class of compounds may be included in the oral veterinary compositions of the invention alone or in combination with one or more of the systemically-acting parasiticides described herein including, but not limited to, one or more isoxazoline active agents, one or more macrocyclic lactone active agents, one or more spinosyn or spinosoid active agents, one or more benzimidazole agents including thiabendazole, oxibendazole, mebendazole, fenbendazole, oxfendazole, albendazole, triclabendazole and febantel; levamisole, pyrantel, morantel, praziquantel, closantel, clorsulon, one or more insect growth regulators, one or more neonicotinoid active agents and one or more aryloazol-2-yl cyanoethylamino active agents, or a combination thereof.

The compositions of the invention may also include aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621 to Le Hir de Fallois, which is also incorporated herein by reference. Aryloazol-2-yl cyanoethylamino active agents, which are systemically-acting against endoparasites may be used alone in the oral veterinary compositions of the invention or in some embodiments in combination with one or more systemically-acting active agents described herein including, but not limited to, one or more isoxazoline active agents, one or more macrocyclic lactone active agents, one or more spinosyn or spinosoid active agents, one or more benzimidazole agents including thiabendazole, oxibendazole, mebendazole, fenbendazole, oxfendazole, albendazole, triclabendazole and febantel, or anthelmintics of other classes including levamisole, pyrantel, morantel, praziquantel, closantel, clorsulon, one or more insect growth regulators, one or more neonicotinoid active agents and one or more amino acetonitrile active agents (AAD), or a combination thereof.

The compositions of the invention may also include paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tett. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432 and US 2010/0197624, U.S. Pat. No. 5,703,078 and U.S. Pat. No. 5,750,695, all of which are hereby incorporated by reference in their entirety. In one embodiment, the paraherquamide and/or marcfortine active agents may be included in the oral veterinary compositions of the invention alone. In other embodiments, the paraherquamide and/or marcfortine active agents may be combined with at least one additional systemically-acting active agents described herein including, but not limited to, one or more isoxazoline active agents, one or more macrocyclic lactone active agents, one or more spinosyn or spinosoid compounds, one or more benzimidazole agents including thiabendazole, oxibendazole, mebendazole, fenbendazole, oxfendazole, albendazole, triclabendazole and febantel, or anthelmintics of other classes including levamisole, pyrantel, morantel, praziquantel, closantel, clorsulon, one or more amino acetonitrile active agents, one or more insect growth regulators, one or more neonicotinoid active agents or one or more aryloazol-2-yl cyanoethylamino active agents, or a combination thereof.

In another embodiment of the invention, the compositions may include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance*," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In one embodiment, oral veterinary compositions, including soft chewable compositions and chewable tablet compositions, comprising a spinosyn and/or a spinosoid active agent, are provided. In some embodiments, the compositions may contain a combination of two or more spinosyn and/or spinosoid active agents. For example, in one embodiment, the compositions may include spinosad, which is a combination of spinosyn A and spinosyn D. Other combinations are also contemplated. In another embodiment, the compositions may include a spinosyn and/or a spinosoid active agent, or a combination thereof, in combination with one or more additional systemically-acting active agents described herein including, but not limited to, one or more isoxazoline active agents, one or more macrocyclic lactone active agents, one or more benzimidazole agents including thiabendazole, oxibendazole, mebendazole, fenbendazole, oxfendazole, albendazole, triclabendazole and febantel, or anthelmintics of other classes including levamisole, pyrantel, morantel, praziquantel, closantel, clorsulon, one or more amino acetonitrile active agents, one or more insect growth regulators, one or more neonicotinoid active agents or an aryloazol-2-yl cyanoethylamino active agent, or a combination thereof.

In general, the systemically-acting active agent (other than an isoxazoline active agent of formula (I), (II), (III) or (IV) described above) is included in the dosage units of the invention in an amount of between about 0.1 μg and about 1000 mg. Typically, the active agent may be included in an amount of about 10 μg to about 500 mg, about 10 μg to about 400 mg, about 1 mg to about 300 mg, about 10 mg to about 200 mg or about 10 mg to about 100 mg. More typically the active agent will be present in an amount of about 5 mg to about 50 mg in the compositions of the invention.

The concentration of systemically-acting active agents (other than an isoxazoline active agent of formula (I), (II), (III) or (IV) described above) in the soft chewable compositions of the invention will typically be from about 0.01% to about 30% (w/w) depending on the potency of the active agent. In certain embodiments for very potent active agents including, but not limited to a macrocyclic lactone active agent, the concentration of the active agent will typically be from about 0.01% to about 10% (w/w), from about 0.01 to about 1% (w/w), from about 0.01% to about 0.5% (w/w), from about 0.1% to about 0.5% (w/w) or from about 0.01% to about 0.1% (w/w). In other embodiments, the concentration of the active agent will typically be from about 0.1% to about 2% (w/w) or about 0.1% to about 1% (w/w).

In other embodiments, the systemically-acting active agent (other than an isoxazoline active agent of formula (I), (II), (III) or (IV) described above) will typically be present at higher concentrations to achieve the desired efficacy. In some embodiments, the active agent will be present in a concentration of about 1% to about 30% (w/w), about 1% to about 20% (w/w) or about 1% to about 15% (w/w). In still other embodiments, the active agent will be present in a concentration of about 5% to about 20% (w/w) or about 5% to about 15% (w/w) in the composition.

In various embodiments of the invention, a systemically-acting active agent (other than an isoxazoline active agent of formula (I), (II), (III) or (IV) described above) may be included in the composition to deliver a dose of about 0.001 mg/kg to about 50 mg/kg or about 0.5 mg/kg to about 50 mg/kg of body weight of the animal. In other embodiments, the active agent will typically be present in an amount sufficient to deliver a dose of about 0.05 mg/kg to about 30 mg/kg, about 0.1 mg/kg to about 20 mg/kg. In other embodiments, the active agent will be present in an amount sufficient to deliver a dose of about 0.1 mg/kg to about 10 mg/kg, about 0.1 mg/kg to about 1 mg/kg or about 0.5 mg/kg to about 50 mg/kg per body weight of the animal.

In certain embodiments of the invention where the systemically-acting active agent is a very potent compound such as a macrocyclic lactone or other potent compounds, the active agent will be present in a concentration to provide a dose of about 0.001 mg/kg to about 5 mg/kg, about 0.001 mg/kg to about 0.1 mg/kg or about 0.001 mg/kg to about 0.01 mg/kg. In still other embodiments, the active agent is present in an amount sufficient to deliver a dose of about 0.01 mg/kg to about 2 mg/kg or about 0.1 mg/kg to about 1 mg/kg per body weight of the animal. In still other embodiments, the additional active agent may be present in an amount to deliver a dose of about 1 μg/kg to about 200 μg/kg or about 0.1 mg/kg to about 1 mg/kg of weight of animal.

Endoparasiticidal Compositions

In one embodiment of the invention, soft chewable veterinary compositions comprising one or more systemically-acting active agents that are active against internal parasites are provided. In this embodiment, the compositions will provide a high level of efficacy against roundworms, whipworms and hookworms while also preventing development of heartworm. In one embodiment, the active agent is a macrocyclic lactone active agent or a combination of two or more macrocyclic lactones. In another embodiment, the active agent is one or more benzimidazole active agents including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue; levamisole, pyrantel, morantel, praziquantel, closantel, clorsulon, one or more amino acetonitrile active agents or one or more aryloazol-2-yl cyanoethylamino active agents, or a combination of thereof.

In another embodiment, the invention provides soft chewable compositions comprising one or more macrocyclic lactones in combination with one or more benzimidazole active agents, levamisole, pyrantel, morantel, praziquantel, closantel, clorsulon, one or more amino acetonitrile active agents or one or more aryloazol-2-yl cyanoethylamino active agents, or a combination of thereof. In still another embodiment, the invention provides soft chewable compositions comprising abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the invention provides soft chewable compositions comprising abamectin, emamectin, eprinomectin, ivermectin, doramectin or selamectin, or a combination thereof. In still another embodiment, soft chewable compositions comprising ivermectin, milbemycin oxime or moxidectin, or a combination thereof, are provided.

In another embodiment, soft chewable compositions comprising a combination of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof, with one or more benzimidazole active agents, levamisole, pyrantel, morantel, praziquantel, closantel, clorsulon, one or more amino acetonitrile active agents or one or more aryloazol-2-yl cyanoethylamino active agents, or a combination of thereof, are provided. In another embodiment, the invention provides soft chewable compositions comprising ivermectin, milbemycin oxime or moxidectin, or a combination thereof, in combination with one or more benzimidazole active agents, levamisole, pyrantel, morantel, praziquantel, closantel, clorsulon, one or more amino acetonitrile active agents or one or more aryloazol-2-yl cyanoethylamino active agents, or a combination of thereof.

In yet another embodiment, the invention provides soft chewable compositions comprising ivermectin, milbemycin oxime or moxidectin, or a combination thereof, with praziquantel, pyrantel, febantel or levamisole. In yet another embodiment, soft chewable compositions comprising ivermectin, milbemycin oxime or moxidectin, or a combination thereof, in combination with praziquantel, one or more benzimidazole active agents or pyrantel, or a combination thereof.

In another embodiment, the endoparasiticidal compositions may include a combination of an isoxazoline active agent in combination with one or more macrocyclic lactone active agents, a benzimidazole, levamisole, pyrantel, morantel, praziquantel, closantel, clorsulon, one or more amino acetonitrile active agents, or one or more aryloazol-2-yl cyanoethylamino active agents, or a combination of thereof.

In another embodiment, the invention provides compositions active against both endoparasites and ectoparasites comprising at least one isoxazoline compound of formula (I), (II), (III) or (IV) in combination with abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof, and optionally with a further systemically-active endoparasiticide selected from one or more benzimidazole active agents, levamisole, pyrantel, morantel, praziquantel, closantel, clorsulon, one or more amino acetonitrile active agents and one or more aryloazol-2-yl cyanoethylamino active agents, or a combination of thereof. In another embodiment, the invention provides compositions comprising at least one isoxazoline compound of formula (A), (B), Compound 1.001-1.025 or Compound 2.001-2.018 in combination with abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In still another embodiment, the invention provides soft chewable compositions comprising Compound A in combination with ivermectin, milbemycin oxime or moxidectin, or a combination thereof. In yet another embodiment, the invention provides soft chewable compositions comprising Compound A in combination with ivermectin, milbemycin oxime or moxidectin, or a combination thereof, and with one or more benzimidazole active agents, levamisole, pyrantel, morantel, praziquantel, closantel, clorsulon, one or more amino acetonitrile active agents or one or more aryloazol-2-yl cyanoethylamino active agents, or a combination of thereof. In another embodiment, the invention provides soft chewable compositions comprising Compound A in combination with ivermectin, milbemycin oxime or moxidectin, or a combination thereof, and with pyrantel, praziquantel, febantel, or a combination of thereof.

In some embodiments, the endoparasiticidal compositions comprising one or more macrocyclic lactones alone or in combination with an isoxazoline active agent will provide an efficacy of at least about 90% against roundworm (*Toxocara canis*), whipworm (*Trichuris vulpis*) or hookworm (*Ancylostoma caninum*) while also preventing development of heartworms and controlling ectoparasites (e.g. fleas and ticks) with a high level of efficacy, as described above. In another embodiment, the compositions of the invention comprising one or more macrocyclic lactone active agents alone or in combination with an isoxazoline active agent will provide an efficacy of at least about 95% against roundworm (*Toxocara canis*), whipworm (*Trichuris vulpis*) or hookworm (*Ancylostoma caninum*). In still another embodiment, the soft chewable compositions of the invention may provide an efficacy of up to 100% against *Dirofilaria immitis* (heartworm) while also controlling fleas and ticks with a high level of efficacy (see above). Thus, administration of the soft chewable compositions of the invention comprising one or more macrocyclic lactones in combination with an isoxazoline active agent will prevent heartworm disease and control endoparasite infections while also controlling ectoparasites (e.g. fleas and ticks).

Formulations

In one embodiment of the invention, the soft chewable veterinary compositions are in the form of a soft chewable formulation ("soft chew") which is palatable and acceptable to the animal. In addition to the active ingredient(s), the soft chews of the invention may include one or more of the following components: a solvent or mixture of solvents, one or more fillers, one or more binders, one or more surfactants, one or more humectants, one or more lubricants, one or more disintegrants, one or more colorants, one or more antimicrobial agents, one or more antioxidants, one or more pH modifiers and one or more flavoring agents.

Preferably, the components of the oral veterinary compositions will be classified as food grade quality or higher (e.g. USP or NF grade). The term "food grade" is used to refer to material that is suitable for consumption by animals and will not contain chemical or other agents that are hazardous to the health of the animal. Thus, a food grade component, if of animal origin, will be prepared to substantially reduce or eliminate the presence of infectious agents or contaminants by processes known in the art such as pasteurization, filtration, pressurization or irradiation. More preferably, the components of the soft chewable veterinary compositions of the invention will not be of animal origin to avoid transmission of infective agents.

Solvents that may be used in the compositions of the invention include, but are not limited to, various grades of liquid polyethylene glycol (PEG) including PEG 200, PEG 300, PEG 400 and PEG 540; propylene carbonate; propylene glycol; triglycerides including, but not limited to caprylic/capric triglyceride, caprylic/capric/linoleic triglyceride (e.g. MIGLYOL® 810 and 812, caprylic/capric/succinic triglyceride, propylene glycol dicaprylate/dicaprate, and the like; water, sorbitol solution, glycerol caprylate/caprate and polyglycolized glycerides (GELUCIRE®), or a combination thereof.

Solvents may be included in the compositions in concentrations of about 1 to about 50% (w/w). In other embodiments, the concentration of the solvents will be from about 1 to about 40% (w/w), about 1 to about 30% (w/w) or about 1 to about 20% (w/w). More typically, the solvents will be in the compositions at concentrations of about 5% to about 20% (w/w) or about 5% to about 15% (w/w).

Various fillers known in the art may be used in the soft chewable compositions of the invention. Fillers include, but are not limited to, corn starch, pre-gelatinized corn starch, soy protein fines, corn cob, and corn gluten meal, and the like. In some embodiments, a combination of two or more fillers may be used in the compositions.

The starch component may comprise starch from any source and may act as a binder in the soft chew. In one embodiment, the starch component used in the compositions is unmodified. In another embodiment, the starch component is derivatized and/or pregelatinized. In another embodiment, the starch component is highly derivatized. Some starches that can serve as a base starch for derivatization include regular corn, waxy corn, potato, tapioca, rice, etc. Suitable types of derivatizing agents for the starch include, but are not limited to, ethylene oxide, propylene oxide, acetic anhydride, and succinic anhydride, and other food approved esters or ethers, introducing such chemicals alone or in combination with one another.

In various embodiments, prior cross-linking of the starch in the starch component may or may not be necessary, based on the pH of the system and the temperature used to form the product.

The starch component may also include amylaceous ingredients. The amylaceous ingredients can be gelatinized or cooked before or during the forming step to achieve the desired matrix characteristics. If gelatinized starch is used, it may be possible to prepare the product of the subject invention or perform the process of the subject invention without heating or cooking. However, ungelatinized (ungelled) or uncooked starch may also be used.

Fillers are typically present in the compositions at a concentration of about 5% to about 80% (w/w), about 10% to about 70% (w/w), about 10% to about 60%, about 10% to about 50% (w/w), or about 10% to about 40% (w/w). More typically, the fillers may be present at concentrations of about 30% to about 70%, about 30% to about 60%, about 30% to about 50% or about 35% to about 55%.

Binders that may be used in the compositions of the invention include, but are not limited to, polyvinylpyrrolidone (e.g. Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g. Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders. In one embodiment, the composition comprises the binders Povidone K30 LP and PEG 3350 or PEG 4000, or a combination thereof. Binders are typically present in the compositions at a concentration of about 1% to about 30% (w/w). More typically, the compositions will include binders at a concentration of about 1% to about 20% (w/w), about 1 to about 15% (w/w), about 1% to about 10% (w/w), about 5% to about 15% (w/w) or about 5% to about 10% (w/w).

Humectants that may be used in the compositions include, but are not limited to, glycerol (also referred to herein as glycerin), propylene glycol, cetyl alcohol and glycerol monostearate, and the like. Polyethylene glycols of various grades may also be used as humectants.

In some embodiments, the humectant may comprise more than one oil including, but not limited to, fat or fats, both natural and synthetic. Oil employed as an ingredient in the soft chew may be a saturated or unsaturated liquid fatty acid, its glyceride derivatives or fatty acid derivatives of plant or animal origin or a mixture thereof. A source for typical animal fats or oils are fish oil, chicken fat, tallow, choice white grease, prime steam lard and mixtures thereof. However, other animal fats are also suitable for use in the soft chew. Suitable sources for vegetable fats or oils can be derived palm oil, palm hydrogenated oil, corn germ hydrogenated oil, castor hydrogenated oil, cotton-seed oil, soybean oil, olive oil, peanut oil, palm olein oil, Cacao fat, margarine, butter, shortening and palm stearin oil, and mixtures thereof. Additionally, a mixture of animal or vegetable oils or fats is suitable for use in the matrix.

Humectants may typically present in the compositions at a concentration of about 1% to about 25% (w/w). Typically, the concentration of the humectant in the composition of the invention will be 1% to about 20% (w/w), about 1% to about 15% (w/w) or about 5% to about 15% (w/w). More typically, the compositions of the invention will contain about 1% to about 10% (w/w) humectant.

Surfactants may be present in the composition at concentrations of about 0.1% to about 10% (w/w), about 1% to about 10% (w/w) or about 5% to about 10% (w/w). More typically, surfactants may be present at concentrations of about 0.1% to about 5% (w/w) or about 1 to about 5% (w/w). Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-α-tocopheryl polyethylene glycol 1000 succinate (TPGS), sodium lauryl sulfate, co-polymers of ethylene oxide and propylene oxide (e.g. poloxomers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like. Polyethylene glycol stearates (synonyms include macrogol stearates, polyoxylstearates, polyoxyethylene stearates, ethoxylated stearates; CAS No. 9004-99-3, 9005-08-7) are mixtures of mono- and distearate esters of mixed polyoxyethylene polymers. Polyethylene glycol hydroxystearate is a mixture of mono- and diesters of hydroxystearic acid with polyethylene glycols. One polyethylene glycol hydroxystearate that may be used in the compositions is polyethylene glycol 12-hydroxystearate. In another embodiment, the compositions may include the surfactant polyethylene glycol 15 12-hydroxystearate (Solutol® HS 15 from BASF), a mixture of mono- and diesters of 12-hydroxystearic acid with 15 moles of ethylene oxide. Again, these compounds, as well as their amounts are well known in the art. In another embodiment of the invention, the compositions may include polyoxyl 35 castor oil (Cremophor® EL) as a surfactant. In other embodiments, the chewable compositions may include polyoxyl 40 hydrogenated castor oil (Cremophor® RH 40) or polyoxyl 60 hydrogenated castor oil (Cremophor® RH60) as surfactants. The compositions of the invention may also include a combination of surfactants.

The type and nature of the surfactant has been found to be very important in keeping the active agent(s) in solution after ingestion and dissolution of the oral compositions. This is particularly important for obtaining the very high bioavailability observed from the inventive oral compositions. However, it has been found that inclusion of certain surfactants with the veterinary dosage forms adversely affect the palatability of the dosage form, resulting in low acceptance by the animals treated. In one embodiment, polyethylene glycol 15 hydroxystearate, polyoxyl 40 hydrogenated castor oil or polyoxyl 60 hydrogenated castor oil, are effective for solubilizing active agents with low water solubility including, but not limited to, isoxazoline active agents and the like, after ingestion by the animal while also maintaining the palatability of the oral dosage form. Thus, in one embodiment of the invention, the oral veterinary compositions comprise Polyethylene glycol 15 hydroxystearate, polyoxyl 40 hydrogenated castor oil or polyoxyl 60 hydrogenated castor oil. In another embodiment of the invention, the veterinary soft chewable compositions of the invention comprise Polyethylene glycol 15 hydroxystearate, polyoxyl 40 hydrogenated castor oil or polyoxyl 60 hydrogenated castor oil at a concentration of about 1 to about 5% (w/w).

In some embodiments, the compositions of the invention may contain one or more disintegrants. Examples of disintegrants that may be used in the compositions of the invention include, but are not limited to, cellulose, carboxymethyl cellulose calcium, carboxymethyl cellulose sodium, polacrilin potassium, starch, hydroxypropyl starch, corn starch, pregelatinized starch, modified starch, lactose monohydrate, croscarmellose sodium, hydroxypropyl cellulose, glycine, Crospovidone, magnesium aluminum silicate, sodium starch glycolate, guar gum, colloidal silicon dioxide, polyvinylpyrrolidone (Povidone), alginic acid, sodium alginate, calcium alginate, methylcellulose, chitosan, and the like, or a combination thereof.

In certain embodiments, the oral veterinary compositions of the invention will include up to about 10% (w/w) of one or more disintegrants. In one embodiment, the compositions may include about 1% (w/w) to about 7% (w/w) of one or more disintegrants. In another embodiment, the compositions may include about 1% (w/w) to about 5% (w/w) or about 2% (w/w) to about 4% (w/w) of one or more disintegrants.

The inventive formulations may contain other inert ingredients such as antioxidants, preservatives, or pH stabilizers. These compounds are well known in the formulation art. Antioxidants may be added to the compositions of the invention to inhibit degradation of the active agents. Suitable antioxidants include, but are not limited to, alpha tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol and the like. The antioxidants are generally added to the formulation in amounts of from about 0.01 to about 2.0% (w/w), based upon total weight of the formulation, with about 0.05 to about 1.0% or about 0.1% to about 0.2% (w/w) being especially preferred.

The compositions of the invention may also include one or more lubricants/processing aids. In some cases, the lubricant/processing aid may also behave as a solvent, and accordingly, there some of the components of the inventive compositions may have dual functions. Lubricants/processing aids include, but are not limited to polyethylene glycols of various molecular weight ranges including PEG 3350 (Dow Chemical) and PEG 4000, corn oil, mineral oil, hydrogenated vegetable oils (STEROTEX or LUBRITAB), peanut oil and/or castor oil. In certain embodiments, the lubricant/processing aid is a neutral oil comprising a medium chain triglyceride or propylene glycol fatty acid esters including caprylic/capric triglycerides. Non-limiting examples of neutral oils are known by the trademark MIGLYOL® including MIGLYOL® 810, MIGLYOL® 812, MIGLYOL® 818, MIGLYOL® 829 and MIGLYOL® 840. If present, the lubricant/processing aid may be in the composition at a concentration of about 1% to about 20% (w/w). Typically, the lubricant/processing aid will be present at a concentration of about 1% to about 15% (w/w) or about 1% to about 10% (w/w). Preferably, the lubricant/processing aid will be present in the composition at a concentration of about 1% to about 5% (w/w).

The compositions may also include anti-microbial agents or preservatives. Suitable preservatives include, but are not limited to, the parabens (methylparaben and/or propylparaben), benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. The concentration of the preservatives in the compositions of the invention are typically from about 0.01 to about 5.0% (w/w), about 0.01 to about 2% (w/w) or about 0.05 to about 1.0% (w/w). In one embodiment, the compositions of the invention will contain about 0.1% to about 0.5% (w/w) of the preservative.

In an embodiment, the oral veterinary compositions of the invention may contain one or more stabilizers to stabilize active ingredients that are susceptible. Suitable stabilizer components include, but are not limited to, magnesium stearate, citric acid, sodium citrate, and the like. However, stabilizer components are common in the art and any suitable one or mixture of more than one may be used. In an embodiment, a stabilizer component comprises about 0.0 percent to about 3.0 percent of the soft chew. In an alternate embodiment, a stabilizer component comprises about 0.5 percent to about 1.5 percent of the soft chew.

Compounds which stabilize the pH of the formulation are also contemplated in the compositions of the invention. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate. In one embodiment, the compositions may include the pH modifier citric acid or a citric acid/citrate combination. The amount of the pH modifier required to achieve a desired pH depends on the nature of the active ingredient(s) and non-active excipients. However, in some embodiments the pH modifier may typically be present in an amount of about 0.1 to about 5% (w/w), about 0.1 to about 3% (w/w) or about 0.1 to about 2% (w/w). More typically, the pH modifier may be present in a concentration of about 0.1 to 1% (w/w) in the inventive compositions.

Many flavoring agents may be used in the compositions of the invention to improve the palatability of the oral veterinary formulations. Preferred flavoring agents are those that are not derived from animal sources. In various embodiments, flavoring components derived from fruit, meat (including, but not limited to pork, beef, chicken, fish, poultry, and the like), vegetable, cheese, bacon, cheese-bacon and/or artificial flavorings may be used. A flavoring component is typically chosen based upon consideration related to the organism that will be ingesting the soft chew. For example, a horse may prefer an apple flavoring component, while a dog may prefer a meat flavoring component. Although flavoring components derived from non-animal sources are preferred, in some embodiments, natural flavors containing beef or liver extracts, etc., may be used such as braised beef flavor artificial powdered beef flavor, roast beef flavor and corned beef flavor among others.

Non-animal flavoring agents include, but are not limited to, artificial beef flavors, flavors derived from plant proteins such as soy protein to which artificial flavoring has been added (e.g. soy-derived bacon flavoring), and flavors derived from plant proteins such as soy protein with no artificial flavoring.

Artificial beef flavors may be obtained from a variety of sources including Pharma Chemie Inc., TetraGenx, Givaudan S. A., Firmenich, Kemin Industries, inc., International Flavors & Fragrances Inc., among others.

In another embodiment, the flavoring component include, but is not limited to, strawberry flavor, tutti fruity flavor, orange flavor, banana flavor, mint flavor, and an apple-molasses.

For administration to cattle, sheep, horses and other grazing animals, as well as small animals such as rabbits, hamsters, gerbils, and guinea pigs, grains and seeds are especially appealing additional flavoring agents. The grains may be present in any form consistent with the production of the chew including flour, bran, cereal, fiber, whole grain and meal forms, including gluten meals, and may be rolled, crimped, ground, dehydrated or milled. Minerals may also be added as flavorings, such as salt and other spices. In one embodiment, the grain utilized is dehydrated, milled or flaked. Vegetables such as dehydrated carrots and seeds such as safflower seeds or milo seeds are especially appealing to small animals and may be included. Additionally, flavors such as Sweet Apple and Molasses Flavor Base and others produced by Pharma Chemie, Givaudan S.A. or other suppliers may be utilized in the compositions.

The compositions of the invention may include one or more flavoring agents in an amount that provides the desired level of palatability to the target animal. The one or more flavoring agents will typically be present in a concentration of about 5% to about 40% (w/w). More typically, the flavoring agents will be present in a concentration of about 10% to about 30%, or about 15% to about 25% (w/w).

In one embodiment, the soft chewable compositions of the invention comprise one or more solvents described above, one or more fillers described above, one or more binders described above, one or more humectants described above, one or more surfactants described above, one or more flavors described above, one or more lubricants described above, and optionally one or more disintegrants described above, one or more preservatives described above, one or more stabilizers described above, one or more antioxidants described above and one or more pH modifying agents described above.

In another embodiment, the compositions may comprise one or more solvents selected from various grades of liquid polyethylene glycol (PEG) including PEG 200, PEG 300, PEG 400 and PEG 540; propylene carbonate, propylene glycol; triglycerides including, but not limited to caprylic/capric triglyceride, caprylic/capric/linoleic triglyceride, caprylic/capric/succinic triglyceride, propylene glycol dicaprylate/dicaprate, glycerol caprylate/caprate and polyglycolized glycerides, or a combination thereof; one or more fillers selected from corn starch, pre-gelatinized corn starch, soy protein fines, corn cob, and corn and gluten meal, or a combination thereof; one or more flavors selected from natural and/or artificial pork, beef, fish or poultry flavor, or a combination thereof; one or more binders selected from polyvinylpyrrolidone (e.g. Povidone), cross-linked polyvinylpyrrolidone (Crospovidone), polyethylene glycols of various grades including PEG 3350, PEG 4000, PEG 6000, PEG 8000 and PEG 20,000; and co-polymers of vinylpyrrolidone and vinyl acetate (e.g. Copovidone), or a combination thereof; and one or more surfactants selected from glyceryl monooleate, polyoxyethylene sorbitan fatty acid esters, sorbitan esters including sorbitan monooleate, polyvinyl alcohol, polysorbates including polysorbate 20 and polysorbate 80, d-α-tocopheryl polyethylene glycol 1000 succinate, sodium lauryl sulfate, co-polymers of ethylene oxide and propylene oxide, polyethylene glycol castor oil derivatives including polyoxyl 35 castor oil, polyoxyl 40 hydrogenated castor oil and polyoxyl 60 hydrogenated castor oil; propylene glycol monolaurate; glyceride esters including glycerol caprylate/caprate, polyglycolized glycerides, PEG 300 caprylic/capric glycerides, PEG 400 caprylic/capric glycerides, PEG 300 oleic glycerides, PEG 300 linoleic glycerides; polyethylene glycol stearates and polyethylene glycol hydroxy stearates including polyoxyl 8 stearate, polyoxyl 40 stearate and polyethylene glycol 15 12-hydroxystearate, or a combination thereof; and optionally one or more humectants described above, one or more lubricants described above, one or more preservatives describe above, one or more stabilizers described above, one or more antioxidants described above and one or more pH modifiers described above.

In another embodiment, the compositions comprise one or more solvents selected from various grades of liquid polyethylene glycol including PEG 300, PEG 400 and PEG 540; propylene carbonate; propylene glycol; caprylic/capric triglyceride, caprylic/capric/linoleic triglyceride, propylene glycol dicaprylate/dicaprate and glycerol caprylate/caprate, or a combination thereof; one or more fillers selected from corn starch, pre-gelatinized corn starch, soy protein fines, or a combination thereof; one or more flavors selected from natural and/or artificial pork, beef, fish or poultry flavor, or a combination thereof; one or more binders selected from polyvinylpyrrolidone, cross-linked polyvinylpyrrolidone, polyethylene glycols of various grades including PEG 3350, PEG 4000, PEG 6000 and PEG 8000; and co-polymers of vinylpyrrolidone and vinyl acetate, or a combination thereof; one or more humectants selected from glycerol, propylene glycol, cetyl alcohol and glycerol monostearate, or a combination thereof; and one or more surfactants selected from polyoxyethylene sorbitan fatty acid esters, sorbitan esters including sorbitan monooleate, polysorbates including polysorbate 20 and polysorbate 80, co-polymers of ethylene oxide and propylene oxide, polyethylene glycol castor oil derivatives including polyoxyl 35 castor oil, polyoxyl 40 hydrogenated castor oil and polyoxyl 60 hydrogenated castor oil; propylene glycol monolaurate; PEG 300 caprylic/capric glycerides, PEG 400 caprylic/capric glycerides, PEG 300 oleic glycerides, PEG 300 linoleic glycerides; polyethylene glycol stearates and polyethylene glycol hydroxy stearates including polyoxyl 8 stearate, polyoxyl 40 stearate and polyethylene glycol 15 12-hydroxystearate, or a combination thereof; and optionally one or more lubricants described above, one or more preservatives described above, one or more stabilizers described above, one or more antioxidants described above and one or more pH modifiers described above.

In yet another embodiment, the soft chewable compositions of the invention comprise one or more solvents selected from liquid polyethylene glycols including PEG 200, PEG 300 and PEG 400; caprylic/capric triglyceride and propylene glycol dicaprylate/dicaprate, or a combination thereof; one or more fillers selected from corn starch, pre-gelatinized corn starch and soy protein fines, or a combination thereof; one or more flavors selected from natural and/or artificial beef, fish or poultry flavor, or a combination thereof; one or more binders selected from polyvinylpyrrolidone, cross-linked polyvinylpyrrolidone, polyethylene glycols of various grades including PEG 3350, PEG 4000 and PEG 6000; and copolymers of vinylpyrrolidone and vinyl acetate, or a combination thereof; one or more humectants selected from glycerol, propylene glycol and cetyl alcohol, or a combination thereof; and one or more surfactants selected from polyoxyethylene sorbitan fatty acid esters, sorbitan esters including sorbitan monooleate, polysorbates including polysorbate 20 and polysorbate 80, polyethylene glycol castor oil derivatives including polyoxyl 35 castor oil, polyoxyl 40 hydrogenated castor oil and polyoxyl 60 hydrogenated castor oil; PEG 300 caprylic/capric glycerides, PEG 400 caprylic/capric glycerides and polyethylene glycol stearates and polyethylene glycol hydroxy stearates including polyoxyl 8 stearate, polyoxyl 40 stearate and polyethylene glycol 15 12-hydroxystearate, or a combination thereof; one or more lubricants selected from polyethylene glycols of various molecular weight ranges including PEG 3350 and PEG 4000, hydrogenated vegetable oils, castor oil, a medium chain triglyceride including caprylic/capric triglycerides and propylene glycol fatty acid esters, or a combination thereof; and optionally one or more preservatives described above, one or more stabilizers described above, one or more antioxidants described above and one or more pH modifiers described above.

In another embodiment, the soft chewable compositions of the invention comprise one or more solvents selected from liquid polyethylene glycols including PEG 300 and PEG 400; caprylic/capric triglyceride and propylene glycol dicaprylate/dicaprate, or a combination thereof; one or more fillers selected from corn starch, pre-gelatinized corn starch and soy protein fines, or a combination thereof; one or more flavors selected from natural and/or artificial beef, fish or poultry flavor, or a combination thereof; one or more binders selected from polyvinylpyrrolidone and polyethylene glycols of various grades including PEG 3350, PEG 4000 and PEG 6000, or a combination thereof; one or more humectants selected from glycerol, propylene glycol and cetyl alcohol, or a combination thereof; and one or more surfactants selected from sorbitan esters including sorbitan monooleate, polysorbates including polysorbate 20 and polysorbate 80, polyethylene glycol castor oil derivatives including polyoxyl 40 hydrogenated castor oil and polyoxyl 60 hydrogenated castor oil; PEG 400 caprylic/capric glycerides and polyethylene glycol stearates and polyethylene glycol hydroxy stearates including polyoxyl 8 stearate, polyoxyl 40 stearate and polyethylene glycol 15 12-hydroxystearate, or a combination thereof; one or more lubricants selected from polyethylene glycols of various molecular weight ranges including PEG 3350 and PEG 4000, caprylic/capric triglycerides and propylene glycol fatty acid esters, or a combination thereof; and optionally one or more preservatives described above, one or more stabilizers described above, one or more antioxidants described above and one or more pH modifiers described above.

In still another embodiment, the soft chewable compositions of the invention comprise one or more solvents selected from liquid polyethylene glycols including PEG 300 and PEG 400; caprylic/capric triglyceride and propylene glycol dicaprylate/dicaprate, or a combination thereof, at a concentration of about 1-20% (w/w) or about 5-20% (w/w); one or more fillers selected from corn starch, pre-gelatinized corn starch and soy protein fines, or a combination thereof, at a concentration of about 30-60% (w/w) or about 30-50% (w/w); one or more flavors selected from natural and/or artificial beef, fish or poultry flavor, or a combination thereof, at a concentration of about 10-30% (w/w) or about 15-25% (w/w); one or more binders selected from polyvinylpyrrolidone and polyethylene glycols of various grades including PEG 3350, PEG 4000 and PEG 6000, or a combination thereof, at a concentration of about 1-10% (w/w) or about 5-15% (w/w); one or more humectants selected from glycerol and propylene glycol, or a combination thereof, at a concentration of about 1-15% (w/w) or about 5-15% (w/w); and one or more surfactants selected from sorbitan esters including sorbitan monooleate, polysorbates including polysorbate 20 and polysorbate 80, polyethylene glycol castor oil derivatives including polyoxyl 40 hydrogenated castor oil and polyoxyl 60 hydrogenated castor oil; PEG 400 caprylic/capric glycerides and polyethylene glycol stearates and polyethylene glycol hydroxy stearates including polyoxyl 8 stearate, polyoxyl 40 stearate and polyethylene glycol 15 12-hydroxystearate, or a combination thereof, at a concentration of about 1-5% (w/w) or about 5-10% (w/w); one or more lubricants selected from polyethylene glycols of various molecular weight ranges including PEG 3350 and PEG 4000, caprylic/capric triglycerides and propylene glycol fatty acid esters, or a combination thereof, at a concentration of about 1-10% (w/w) or about 1-5% (w/w); and optionally one or more preservatives described above, one or more stabilizers described above, one or more antioxidants described above and one or more pH modifiers described above.

In another embodiment, the soft chewable compositions of the invention comprise one or more solvents selected from liquid polyethylene glycols including PEG 300 and PEG 400; and caprylic/capric triglyceride, or a combination thereof, at a concentration of about 5-20% (w/w); one or more fillers selected from corn starch, pre-gelatinized corn starch and soy protein fines, or a combination thereof, at a concentration of about 30-50% (w/w); one or more flavors selected from natural and/or artificial beef, fish or poultry flavor, or a combination thereof, at a concentration of about 15-25% (w/w); one or more binders selected from polyvinylpyrrolidone and polyethylene glycols of various grades including PEG 3350, PEG 4000 and PEG 6000, or a combination thereof, at a concentration of about 5-15% (w/w); one or more humectants selected from glycerol and propylene glycol, or a combination thereof, at a concentration of about 5-15% (w/w); and one or more surfactants selected from polysorbates including polysorbate 20 and polysorbate 80, polyethylene glycol castor oil derivatives including polyoxyl 40 hydrogenated castor oil and polyoxyl 60 hydrogenated castor oil; PEG 400 caprylic/capric glycerides and polyethylene glycol stearates and polyethylene glycol hydroxy stearates including polyoxyl 8 stearate, polyoxyl 40 stearate and polyethylene glycol 15 12-hydroxystearate, or a combination thereof, at a concentration of about 1-5% (w/w) or about 5-10% (w/w); one or more lubricants selected from polyethylene glycols of various molecular weight ranges including PEG 3350 and PEG 4000 and caprylic/capric triglycerides, or a combination thereof at a concentration of about 1-5% (w/w); and optionally one or more preservatives described above, one or more stabilizers described above, one or more antioxidants described above and one or more pH modifiers described above.

In another embodiment, the oral veterinary compositions of the invention are in the form of a chewable tablet. The tablet compositions will comprise an effective amount of at least one systemically-acting active agent described herein, and typically a flavor, a filler, a lubricant, and a flow aid. Optionally, the inventive tablets may further contain at least one of the following ingredients: colorants, binders, antioxidants, disintegrants, or preservatives. Moreover, in an alternative embodiment the invention provides for tablets which are coated. The inventive tablets are prepared according to methods conventional in the art, such as wet and dry granulation processes.

Many of the ingredients for the tablet include those provided for in the soft chewable formulations described above. With respect to fillers (or diluents), the inventive tablets contemplate all the fillers which are known in the tablet art. Non-limiting examples of fillers include anhydrous lactose, hydrated lactose, sprayed dried lactose, crystalline maltose and maltodextrins.

Flow aids or glidants are also well known in the art and include, for example, silicon dioxide (CARBOSIL) or silica gel (SYLOID), talc, starch, calcium, stearate, magnesium stearate, and aluminum magnesium silicate (NEUSILIN). Amounts of flow aids are readily determined by a practitioner in this art and include for using about 0.01 to about 25%, based upon weight of total composition. Non-limiting examples of lubricants for the tablets include magnesium and calcium stearate and stearic acid. Again, the various lubricants are well known to a practitioner of this art as well as the amounts of these compounds. Ranges include from about 0.01 to about 20% (w/w).

In various embodiments, the oral compositions of the invention may be coated. Any suitable coating may be used. In an embodiment, a coating is chosen that will not interfere with an additive. In another embodiment, an additive is chosen that can modify the time for digestion of the additive(s), thereby at least partially controlling the release of the additive(s). Suitable coatings include, but are not limited to, and may be any pharmaceutically acceptable, and/or neutraceutically acceptable coating, as is common in the art. (polymers, monomers). Reference can be had to U.S. Pat. No. 6,498,153, incorporated herein by reference, to Cady et al. for a list of polymers that can function as coatings.

In other embodiments, coatings for the oral veterinary formulations include gelatin, glyceryl behenate, coca butter, and beeswax. Other coatings would be known to a practitioner in this art. Coatings for tablets include sugar coatings, such as seal coatings, subcoatings, and syrup coatings, as well as film coatings, such as pan-pour coatings and pan spray coatings. As well known to a practitioner of this art, the coatings contain additional components such as solvents, plasticizers, colorants, opaquant-extenders and film formers.

Method of Manufacture

The soft chews of the invention are prepared by mixing the active ingredient(s) with the non-active excipients in a mixer and mixing the components to achieve a dough-like mixture wherein the active ingredient(s) are homogeneously distributed. The resulting dough-like mixture is then formed into soft chewable dosage units of different sizes for different size animals.

In one embodiment, the process to manufacture the soft chews will not include the addition of water, although there may be some amount of water included with certain components used. The presence of significant amounts of water in veterinary compositions is known to affect the stability of certain active agents. Thus, in certain embodiments of the invention water will not be added to the composition where active agents and/or excipients are used that are susceptible to degradation in the presence of water.

The temperature at which the soft chewable veterinary compositions of the invention are prepared is dependent on the stability requirements of the active and non-active components of the compositions. In certain cases where ingredients that are not temperature-sensitive are used, higher processing temperatures may be tolerable. However, when active and non-active ingredients are used that are sensitive to temperature, the process may be adapted to operate at a temperature range that will not adversely impact the stability of the composition. In some embodiments, the process will preferably not impart significant amounts of heat during any one processing step to avoid the possible degradation of any of the components of the composition. Thus, in some embodiments, any one step of the process may be operated so that the average temperature of the mixture does not rise more than about 20° C. above room temperature (room temperature will be considered 20-25° C.). In other embodiments, the process will be conducted so that the average temperature of the mixture does not rise more than about 15° C., more than about 10° C. or more than about 5° C. above room temperature. In still another embodiment, the process may be conducted so that the average temperature of the mixture will not rise more than about 3° C. above room temperature. In some embodiments, the required temperature may be maintained by the use of process cooling devices. In other embodiments, the required temperature may be maintained by using equipment that does not produce sufficient heat to maintain the required temperature of the mixture during processing.

In one embodiment, active and inactive ingredients for the soft chews of the invention are added to a mixing vessel such as a planetary or double planetary mixer or a horizontal mixer capable of blending the material and casting it against the side of the mixing vessels. This action permits the ingredients to be well and consistently blended without application of heat or addition of pharmaceutical grade water to the mixture.

Horizontal mixers generally comprise a mixing chamber, an elongated, horizontal mixing shaft which rotates, and a plurality of mixing tools which depend generally perpendicularly from the horizontal shaft to rotate around the inside of the chamber (see, e.g., U.S. Pat. No. 5,735,603, the disclosure of which is incorporated herein by this reference). The mixing tools are configured and dimensioned as required for the mixing process to follow the shape of the chamber walls as rotated for proper mixing of all of material present. Some such mixing chambers are cylindrically shaped, while others are trough-shaped, such as mixers which are commonly referred to in the art as double-arm mixers or ribbon mixers.

In one embodiment, the soft chewable compositions of the invention may be formed from the dough-like mixture by any suitable forming techniques known in the art including forming by hand. One of skill in the art will understand that once the homogeneous dough mixture having the required properties is prepared the individual dosage units of various sizes may be formed by weighing the required amount of the dough-like mixture and forming the soft chewable compositions by hand or using any other molding techniques known in the art. In one embodiment, the dough-like mixture is extruded to form the soft chewable dosage forms. In another embodiment, the soft chewable dosage forms are formed using a forming machine. A variety of forming equipment may be utilized in the invention including molding machines developed for use in producing molded food products, such as pre-formed hamburger patties and chicken nuggets. For example, the molding machines described in U.S. Pat. Nos. 3,486,186; 3,887,964; 3,952,478; 4,054,967; 4,097,961; 4,182,003; 4,334,339; 4,338,702; 4,343,068; 4,356,595; 4,372,008; 4,523,520; 4,535,505; 4,597,135; 4,608,731; 4,622,717; 4,697,308; 4,768,941; 4,780,931; 4,818,446; 4,821,376; 4,872,241; 4,975,039; 4,996,743; 5,021,025; 5,022,888; 5,165,218; 5,655,436; 5,980,228 and 7,780,931 (the disclosures of which are incorporated herein by reference) are representative of forming equipment that may be utilized in the invention.

In one embodiment forming equipment that does not apply compression heat to the chew mixture may be utilized. Non-limiting examples of forming machines include those manufactured by NuTec Manufacturing including model nos. 710, 720, 745, 750 and 760; and those manufactured by the Formax Corporation, including the VerTex 1000, NovaMax 500, Maxum 700, Ultra 26, F-19, F-400 and F-6. The order of mixing the components is not critical and various processing schemes may be used to form the dough-like mixture prior to forming the soft chew dosage units. In some embodiments, the active ingredient(s) and possibly some non-active components such as preservatives or antioxidants may first be dissolved in a solvent(s) prior to mixing with other non-active components of the composition in a blender to form a dough-like mixture. The liquid components may be added at a controlled rate to ensure homogeneity of the mixture. Alternatively, the active ingredient(s) may be mixed in dry form (solid state) with other non-active components in a blender and liquid components may be added to the dry blended mixture with further mixing to form a uniform dough-like mixture. In still another embodiment, the liquid components of the invention may first be placed in the blender and the dry components, including active agent(s) may be added to the liquid with further mixing to form a uniform dough-like mixture.

Methods of Treatment

In another aspect of the invention, a method for preventing and/or treating a parasite infestation and/or infection in an animal is provided, comprising administering to the animal an oral veterinary composition comprising an effective amount of at least one systemically-acting active agent together with a pharmaceutically acceptable carrier to the animal. In one embodiment, the compositions comprise at least one isoxazoline active agent. In another embodiment, the compositions may include one or more macrocyclic lactone active agents, one or more spinosyn or spinosoid compounds, one or more benzimidazole agents including thiabendazole, oxibendazole, mebendazole, fenbendazole, oxfendazole, albendazole, triclabendazole and febantel; or active agents of other classes including levamisole, pyrantel, morantel, praziquantel, closantel, clorsulon, one or more insect growth regulators, one or more neonicotinoid active agents, one or more amino acetonitrile active agents, or one or more aryloazol-2-yl cyanoethylamino active agents, or a combination thereof. In still another embodiment the compositions may include at least one isoxazoline active agent in combination with one or more macrocyclic lactones, one or more spinosyn and/or spinosoid compounds, one or more benzimidazole active agents including thiabendazole, oxibendazole, mebendazole, fenbendazole, oxfendazole, albendazole, triclabendazole and febantel; or active agents of other classes including levamisole, pyrantel, morantel, praziquantel, closantel, clorsulon, one or more amino acetonitrile active agents, one or more insect growth regulators, one or more neonicotinoid active agents or one or more aryloazol-2-yl cyanoethylamino active agents, or a combination thereof.

In one embodiment, the oral veterinary composition is a soft chewable composition. In another embodiment, the oral veterinary composition is a chewable tablet composition.

The methods and uses of the invention comprise the administration of any of the compositions of the invention described herein to an animal in need thereof. The compositions of the invention have been found to provide long-lasting efficacy against ectoparasites (e.g. fleas and ticks) and/or endoparasites with a very fast onset of action, as described above. Furthermore, it has been found that the administration of the active agents in the inventive oral compositions of the invention provide a very high level of bioavailability of the active agent after oral administration to the animal. Thus, depending on the active agent included in the compositions, the invention provides methods and uses for the treatment and prevention of endoparasitic infections and/or ectoparasitic infestations in an animal, which comprise administering an effective amount of an oral composition of the invention to the animal.

In one embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Gasterophilus, Lucilia, Dermatobia, Cochliomyia, Chrysomyia, Damalinia, Linognathus, Haematopinus, Solenopotes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include, but are not limited to, cat and dog fleas (*Ctenocephalides felis, Ctenocephalides* sp. and the like), ticks (*Rhipicephalus* sp., *Ixodes* sp., *Dermacentor* sp., *Amblyomma* sp., *Haemaphysalis* sp., and the like), and mites (*Demodex* sp., *Sarcoptes* sp., *Otodectes* sp., *Cheyletiella* sp., and the like), lice (*Trichodectes* sp., *Felicola* sp., *Linognathus* sp., and the like), mosquitoes (*Aedes* sp., *Culex* sp., *Anopheles* sp., and the like) and flies (*Hematobia* sp. including *Haematobia irritans, Musca* sp., *Stomoxys* sp. including *Stomoxys calcitrans, Dermatobia* sp., *Cochliomyia* sp., and the like).

Additional examples of ectoparasites include but are not limited to the tick genus *Boophilus*, especially those of the species microplus (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa) and *Gasterophilus* in horses. Flies proper, namely those whose adult constitutes the parasite, such as *Haematobia irritans* (horn fly) and *Stomoxys calcitrans* (stable fly); lice such as *Linognathus vituli*, etc.; and mites such as *Sarcoptes scabiei* and *Psoroptes ovis*. The above list is not exhaustive and other ectoparasites are well known in the art to be harmful to animals and humans. These include, for example migrating dipteran larvae.

In some embodiments of the invention, the composition can also be used to treat animals for endoparasite infestations such as those comprised of helminths selected from the group consisting of *Anaplocephala, Ancylostoma, Anecator, Ascaris, Capillaria, Cooperia, Cyathostomum, Dipylidium, Dirofilaria, Echinococcus, Enterobius, Fasciola, Haemonchus, Oesophagostumum, Ostertagia, Parascaris, Toxocara, Strongylus, Strongyloides, Toxascaris, Trichinella, Trichuris* and *Trichostrongylus*, among others.

In one embodiment, the invention provides methods for the treatment and prevention of parasitic infections and infestations of animals (either wild or domesticated), including livestock and companion animals such as cats, dogs, horses, birds including chickens, sheep, goats, pigs, turkeys and cattle, with the aim of ridding these hosts of parasites commonly encountered by such animals.

In another embodiment, the invention provides methods for the treatment and/or prevention of parasitic infections and infestations in companion animals including, but not limited to, cats and dogs. Some methods and compositions of the invention that comprise isoxazoline active agents are particularly effective for preventing or treating parasitic infestations of cats and dogs with fleas and ticks or other ectoparasites.

In another embodiment, the methods and compositions of the invention are used for the treatment or prevention of parasitic infections and infestations in cattle or sheep. When treating livestock animals such as cattle or sheep, the methods and compositions of the invention that comprise an isoxazoline active agent are particularly effective against *Rhipicephalus* (*Boophilus*) *microplus, Haematobia irritans* (horn fly), *Stomoxys calcitrans* (stable fly), and sheep myiases such as *Lucilia sericata, Lucilia cuprina* (known as blowfly strike in Australia, New Zealand and South Africa).

In one embodiment, the invention provides a method for preventing and/or treating a parasitic infestation and/or infection in an animal that comprises administering to the animal a soft chewable veterinary composition comprising an effective amount of at least one isoxazoline active agent in combination with an effective amount at least a second active agent in a pharmaceutically acceptable carrier. Any of the additional active agents described above may be combined with the isoxazoline active agent in the soft chewable veterinary compositions.

In another embodiment, the invention provides a method for preventing and/or treating an endoparasitic infection in an animal that comprises administering to the animal a soft chewable veterinary composition comprising an effective amount of a systemically-acting active agent that is active against internal parasites including one or more macrocyclic lactones, one or more benzimidazole active agents including thiabendazole, oxibendazole, mebendazole, fenbendazole, oxfendazole, albendazole, triclabendazole and febantel; or anthelmintics of other classes including levamisole, pyrantel, morantel, praziquantel, closantel, clorsulon, one or more amino acetonitrile active agents, or one or more aryloazol-2-yl cyanoethylamino active agents, or a combination thereof. The methods of the invention for the treatment and/or prevention of endoparasites are effective against parasitic nematodes, (including roundworm, hookworm, whipworm and others), and/or *Dirofilaria immitis* (Heartworm).

In another embodiment, the invention provides a method for preventing and/or treating an endoparasitic infection in an animal that comprises administering to the animal a soft chewable veterinary composition comprising an effective amount of one or more macrocyclic lactones including, but not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin and nemadectin. In another embodiment, method comprises administering an effective amount of a soft chewable composition comprising one or more of abamectin, emamectin, eprinomectin, ivermectin, doramectin or selamectin. In yet another embodiment, the method comprises administering an effective amount of a soft chewable composition comprising ivermectin, milbemectin, milbemycin oxime or moxidectin, or a combination thereof.

In yet embodiment of the invention, the methods and uses of the invention comprising one or more macrocyclic lactones, one or more spinosyn compounds, one or more benzimidazoles, levamisole, pyrantel, morantel, praziquantel, closantel, clorsulon, one or more amino acetonitrile active agents or one or more aryloazol-2-yl cyanoethylamino active agents, or a combination of thereof, in the compositions will provide an efficacy of at least about 90% against roundworm (*Toxocara canis*), whipworm (*Trichuris vulpis*) or hookworm (*Ancylostoma caninum*). In another embodiment, the methods and uses of the invention comprising an active agent that is active against internal parasites including, but not limited to, one or more macrocyclic lactones, will provide an efficacy of at least 95% against roundworm (*Toxocara canis*), whipworm (*Trichuris vulpis*) or hookworm (*Ancylostoma caninum*). In still another embodiment, the methods and uses of the invention will provide an efficacy of up to 100% against *Dirofilaria immitis* (heartworm).

In some embodiments, the combination of certain active agents with an isoxazoline active agent will expand the scope of coverage of the method depending on the biological activity of the additional active agent. For example, it is contemplated that combination of the isoxazoline active agent with one or more additional active agents that are active against internal parasites such as parasitic nematodes, (including roundworm, hookworm, whipworm and others), and/or *Dirofilaria immitis* (Heartworm) will provide treatment and/or protection against internal parasites as well as external parasites (e.g. fleas and ticks, etc.). Thus, the invention provides a method for the treatment and/or prevention of an ectoparasitic infestation and an endoparasitic infection, comprising administering to the animal in need a soft chewable veterinary composition comprising at least one isoxazoline compound in combination with at least one compound that is active against internal parasites.

In one embodiment, the invention provides a method for treating and/or preventing an endoparasitic infestation and ectoparasitic infection in an animal that comprises administering a soft chewable veterinary composition comprising an effective amount at least one isoxazoline active agent together with an effective amount of at least one macrocyclic lactone active agent. In some embodiments, the composition may comprise at least one isoxazoline compound in combination with abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin or nemadectin, or a combination thereof.

In another embodiment, methods and uses for the treatment and/or prevention of an ectoparasitic infestation and endoparasitic infection are provided wherein the composition administered comprises at least one isoxazoline active agent in combination with one or more macrocyclic lactones and one or more spinosyn compounds, one or more spinosoid compounds, one or more benzimidazoles, levamisole, pyrantel, morantel, praziquantel, closantel, clorsulon, one or more amino acetonitrile active agent, one or more insect growth regulators, one or more neonicotinoids or one or more aryloazol-2-yl cyanoethylamino active agents, or a combination of thereof.

In one embodiment, the invention provides methods and uses for the treatment and prevention of parasitic infections and infestations of animals (either wild or domesticated), including livestock and companion animals such as cats, dogs, horses, birds including chickens, sheep, goats, pigs, turkeys and cattle, with the aim of ridding these hosts of parasites commonly encountered by such animals.

In another embodiment, the invention provides methods and uses for the treatment or prevention of parasitic infections and infestations in companion animals including, but not limited to, cats and dogs.

The compositions of the invention are administered in parasiticidally effective amounts which are suitable to control the parasite in question to the required extent, as described herein.

In some embodiments for methods that comprise an isoxazoline active agent, a dose of from about 0.05 about 100 mg per kg of body weight of the isoxazoline active agent given as a single dose or in divided doses for a period of from 1 to 5 days will be satisfactory but, of course, there can be instances where higher or lower dosage ranges are indicated, and such are within the scope of this invention. More typically, the dose of the isoxazoline active agent may be between about 0.1 to about 50 mg per kg, about 0.1 to about 25 mg/kg or about 0.1 to about 10 mg/kg of body weight. In one embodiment, the dose of the isoxazoline active agent administered will be about 0.1 to about 5 mg/kg or about 1 to about 5 mg/kg of body weight. In another embodiment for long-lasting compositions, the compositions will contain a dose of about 10 mg/kg to about 100 mg/kg of an isoxazoline active agent. More typically, the higher dose compositions will contain a dose of about 10 mg/kg to about 50 mg/kg or about 10 mg/kg to about 30 mg/kg of an isoxazoline active agent. In one embodiment, the high dose compositions will contain a dose of about 15 mg/kg to about 25 mg/kg per body weight of an isoxazoline active agent. It is well within the routine skill of the practitioner to determine a particular dosing regimen for a specific host and parasite.

In various other embodiments of the invention, the methods and uses of the invention will include administering a soft chewable veterinary composition comprising systemically-acting active agents that are active against internal parasites (endoparasiticidal) including, but not limited to, one or more macrocyclic lactones, one or more spinosyn compounds, one or more spinosoid compounds, a benzimidazole, levamisole, pyrantel, morantel, praziquantel, closantel, clorsulon, one or more amino acetonitrile active agent, or one or more aryloazol-2-yl cyanoethylamino active agents, or a combination of thereof.

Generally, the active agent active against internal parasites may be included in the composition to deliver a dose of about 0.05 mg/kg to about 50 mg/kg or about 0.5 mg/kg to about 50 mg/kg of body weight of the animal. In other embodiments, the endoparasiticidal active agent will typically be present in an amount sufficient to deliver a dose of about 0.05 mg/kg to about 30 mg/kg, about 0.1 mg/kg to about 20 mg/kg, about 0.1 mg/kg to about 10 mg/kg, about 0.1 mg/kg to about 1 mg/kg or about 0.5 mg/kg to about 50 mg/kg per body weight of the animal.

In certain embodiments of the invention where the endoparasiticidal active agent is a very potent compound such as a macrocyclic lactone, the active agent will be present in a concentration to provide a dose of about 0.001 mg/kg to about 5 mg/kg, about 000.1 mg/kg to about 0.1 mg/kg or about 0.001 mg/kg to about 0.01 mg/kg. In still other embodiments, the active agent is present in an amount sufficient to deliver a dose of about 0.01 mg/kg to about 2 mg/kg or about 0.1 mg/kg to about 1 mg/kg per body weight of the animal. In still other embodiments, the active agent may be present in an amount to deliver a dose of about 1 µg/kg to about 200 µg/kg or about 0.1 mg/kg to about 1 mg/kg weight of animal.

In one embodiment of the invention, the methods and uses of the invention comprising an isoxazoline active agent provide protection of at least 90% efficacy against fleas (*C. felis*) for at least 30 days or at least 36 days as measured against untreated controls according to the methods described in the examples. In another embodiment, the soft chewable compositions of the invention provide at least 90% efficacy against fleas for at least 44 days or for at least 58 days.

In certain embodiments of the invention, methods and uses comprising an isoxazoline active agent are provided that provide a high level of efficacy against fleas for periods of time in excess of 60 days. For example, in one embodiment, the compositions of the invention provide an efficacy of at least 90% against fleas for at least 72 days. In other embodiments, the compositions of the invention provide an efficacy of at least 90% against fleas for at least 79 days, at least 86 days or even at least 93 days. In still other embodiments, the very long lasting oral compositions of the invention provide an efficacy of at least 90% against fleas for at least about 100 days, at least about 107 days or even at least about 114 days.

In yet another embodiment, methods and uses of the invention comprising an isoxazoline active agent provide an efficacy of at least about 95% against fleas (*C. felis*) for at least about 30 days or at least about 36 days. In yet another embodiment, the methods and uses of the invention provide an efficacy of at least about 95% against fleas for at least about 44 days, at least about 58 days or at least about 72 days. In still other embodiments, the methods and uses of the invention provide an efficacy of at least about 95% against fleas for at least about 79 days, at least about 86 days or even about 93 days or longer. For example, the methods and uses of the invention wherein compositions containing higher doses of an isoxazoline active agent are administered may provide an efficacy of at least about 95% against fleas for at least about 100 days, or even at least about 107 days or longer.

In yet another embodiment of the invention, the methods and uses of the invention comprising administering a composition comprising an isoxazoline active agent provide about 100% efficacy against fleas for at least about 23 days, at least about 30 days or at least about 36 days. In still other embodiments, the methods and uses of the invention provide an efficacy of about 100% against fleas for at least about 44 days, at least about 58 days or at least about 72 days.

In another embodiment of the invention, the methods and uses of the invention that comprise administering an oral composition comprising an isoxazoline active agent provide an efficacy of at least about 90% against ticks (including, but not limited to, *Dermacentor variabilis, Ixodes scapularis, Amblyomma americanum, Rhipicephalus sanguineus, Ixodes ricinus, Dermacentor reticulatus* and *Ixodes holocyclus*) for at least about 23 days. More typically, the compositions will provide an efficacy of at least about 90% against ticks for at least about 30 days or at least about 36 days. In still another embodiment, the methods and uses of the invention will provide an efficacy of at least about 95% for at least about 23 days, at least about 30 days or at least about 36 days.

In some embodiments, the methods and uses of the invention comprising administering a composition that includes an isoxazoline active agent provide an efficacy against ticks of at least about 90% for at least about 44 days, at least about 58 days, or at least about 72 days. In other embodiments, the methods and uses of the invention provide an efficacy against ticks of at least about 90% for at least about 79 days, at least about 86 days or at least about 93 days. In other embodiments, the methods and uses of the invention provide an efficacy against ticks of at least about 95% for at least about 44 days, at least about 58 days, at least about 72 days or even at least about 79 days. In certain other embodiments, the methods and uses of the invention with higher doses of the isoxazoline active agent may provide an efficacy against ticks of at least 90%, at least 95% or even 100% for at least about 100 days or even for at least about 107 days, depending on the species of ticks. This very high level of efficacy against ticks for such extended periods of time from an oral dosage form is striking and without precedence in immediate release oral dosage forms. Furthermore, the methods and uses of the invention are surprisingly effective against hard to control ticks, including *Amblyomma americanum* and others.

In yet another embodiment of the invention, the methods and uses of the invention of the invention that comprise a combination of an isoxazoline active agent in combination with a macrocyclic lactone active agent will provide an efficacy of at least about 90% against roundworm (*Toxocara canis*), whipworm (*Trichuris vulpis*) or hookworm (*Ancylostoma caninum*) while also controlling ectoparasites (e.g. fleas and ticks) with a high level of efficacy, as described above. In another embodiment, the methods and uses of the invention comprising an isoxazoline active agent in combination with a macrocyclic lactone will provide an efficacy of at least 95% against roundworm (*Toxocara canis*), whipworm (*Trichuris vulpis*) or hookworm (*Ancylostoma caninum*). In still another embodiment, the methods and uses of the invention will provide an efficacy of up to 100% against *Dirofilaria immitis* (heartworm) while also controlling fleas and ticks with a high level of efficacy (see above). Thus, administration of the soft chewable compositions of the invention will prevent heartworm infection and control infection of endoparasites while also controlling ectoparasites (e.g. fleas and ticks).

In another embodiment, the methods and uses of the invention of the invention that comprise at least one systemically-acting endoparasiticidal active agent, with or without an isoxazoline active agent, including one or more macrocyclic lactones, one or more spinosyn compounds, one or more spinosoid compounds, one or more benzimidazoles, levamisole, pyrantel, morantel, praziquantel, closantel, clorsulon, one or more amino acetonitrile active agents or one or more aryloazol-2-yl cyanoethylamino active agents, or a combination of thereof, will provide an efficacy of at least about 90% against roundworm (*Toxocara canis*), whipworm (*Trichuris vulpis*) or hookworm (*Ancylostoma caninum*). In another embodiment, the methods and uses of the invention comprising comprise at least one systemically-acting endoparasiticidal active agent including one or more macrocyclic lactones, one or more spinosyn compounds, one or more spinosoid compounds, one or more benzimidazoles, levamisole, pyrantel, morantel, praziquantel, closantel, clorsulon, one or more amino acetonitrile active agents or one or more aryloazol-2-yl cyanoethylamino active agents, or a combination of thereof, with or without an isoxazoline active agent, will provide an efficacy of at least 95% against roundworm (*Toxocara canis*), whipworm (*Trichuris vulpis*) or hookworm (*Ancylostoma caninum*). In still another embodiment, the methods and uses of the invention comprising administering a soft chewable composition that includes one or more macrocyclic lactone active agents in combination with an isoxazoline active agent will provide an efficacy of up to 100% against *Dirofilaria immitis* (heartworm) while also controlling fleas and ticks with a high level of efficacy (see above).

By "treating" or "treat" or "treatment" is intended the application or administration of a composition of the invention to an animal that has a parasitic infestation for the eradication of the parasite or the reduction of the number of the parasites infesting the animal undergoing treatment. It is noted that the compositions of the invention may be used to prevent and control such a parasitic infestation.

The compositions of the invention are administered in parasiticidally effective amounts which are suitable to control the parasite in question to the desired extent, as described below. In each aspect of the invention, the compounds and compositions of the invention can be applied against a single pest or combinations thereof.

The compositions of the invention may be administered continuously, for treatment or prevention of parasitic infections or infestations. In this manner, the compositions of the invention deliver an effective amount of the active compounds to the animal in need thereof to control the target parasites.

EXAMPLES

The invention is further described by the following non-limiting examples which further illustrate the invention, and are not intended, nor should they be interpreted to, limit the scope of the invention.

Soft chews containing the isoxazoline active agent 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (Compound A) as a representative isoxazoline compound alone and in combination with a macrocyclic lactone were prepared with a variety of non-active excipients and evaluated for effectiveness to control endoparasites and ectoparasites in cats and dogs. In addition, soft chewable compositions comprising one or more parasiticides that are active against endoparasites were prepared and evaluated for efficacy against various internal parasites.

Example 1

Preparation of Soft Chewable Veterinary Formulations

The soft chewable formulation of Table 1 was prepared by the following procedure: the active agent(s) and potassium sorbate (if present) were dissolved in the corresponding amount of solvent by mixing at ambient temperature. In a blender, the filler (e.g. soy protein fines and/or starch) are mixed together at ambient temperature until blended, then the other non-active components and the pre-made solution of the active agent(s) and potassium sorbate (if present) are added to the mixture. The mixture is stirred further until a well-blended dough-type mixture is formed.

The dough-like mixture is then formed into individual soft chewable dosage units in nominal sizes of 0.5 g, 1 g and 4 g. The formulations in Tables 2-24 may be prepared by similar procedures. In the tables below, the abbreviation "QS" meaning "Quantum sufficit" is intended to mean that the amount of corresponding component may be adjusted to bring the composition to 100% (w/w).

TABLE 1

| Ingredients | Function | % (w/w) |
| --- | --- | --- |
| Cmpd. A | Active | 2.2 |
| Soy Protein Fines | Filler | 26.5 (QS) |
| Corn Starch | Filler | 31.0 |
| artificial meat flavor | Flavoring | 5.1 |
| artificial beef flavor | Flavoring | 7.1 |
| Povidone K-30 | Binder | 2.8 |
| PEG 400 | Solvent | 7.1 |
| PEG 4000 | Binder | 6.4 |
| polyethylene glycol 12-hydroxystearate | Surfactant | 3.0 |
| Glycerin | Humectant | 5.1 |
| Potassium Sorbate | Preservative | 0.3 |
| Caprylic/capric triglyceride | Solvent/Lubricant | 3.2 |

TABLE 2

| Ingredients | Function | % (w/w) |
| --- | --- | --- |
| Cmpd. A | Active | 2.2 |
| Soy Protein Fines | Filler | 56.0 (QS) |
| artificial meat flavor | Flavoring | 5.5 |
| artificial beef flavor | Flavoring | 7.5 |
| Povidone K-30 | Binder | 2.8 |
| PEG 4000 | Binder | 6.4 |
| Sorbitan monooleate | Surfactant | 4.0 |
| Glycerin | Humectant | 5.1 |
| Potassium Sorbate | Preservative | 0.3 |
| Propylene glycol dicaprylate/dicaprate | Solvent/Lubricant | 3.2 |
| Propylene glycol | Solvent | 7.0 |

TABLE 3

| Ingredients | Function | % (w/w) |
| --- | --- | --- |
| Cmpd. A | Active | 2.2 |
| Soy Protein Fines | Filler | 31 (QS) |
| Corn Gluten Meal | Filler | 30.0 |
| artificial beef flavor | Flavoring | 12.0 |
| Povidone K-30 | Binder | 2.8 |
| PEG 4000 | Binder | 6.4 |
| Polyoxyl 60 hydrogenated castor oil | Surfactant | 4.0 |
| Potassium Sorbate | Preservative | 0.3 |
| Propylene glycol dicaprylate/dicaprate | Solvent/Lubricant | 3.2 |
| PEG 400 | Solvent | 8.0 |

TABLE 4

| Ingredients | Function | % (w/w) |
| --- | --- | --- |
| Cmpd. A | Active | 2.2 |
| Soy Protein Fines | Filler | 32.0 (QS) |
| Pre-gelatinized Corn Starch | Filler | 31.0 |
| artificial beef flavor | Flavoring | 12.0 |
| Povidone K-30 | Binder | 2.8 |
| PEG 4000 | Binder | 6.4 |
| polyoxyl 35 castor oil | Surfactant | 4.0 |
| Potassium Sorbate | Preservative | 0.3 |
| Propylene glycol dicaprylate/dicaprate | Solvent/Lubricant | 3.2 |
| PEG 400 | Solvent | 6.0 |

TABLE 5

| Ingredients | Function | % (w/w) |
| --- | --- | --- |
| Cmpd. A | Active | 2.2 |
| Soy Protein Fines | Filler | 26.0 (QS) |
| Pre-gelatinized Corn Starch | Filler | 30.0 |
| beef flavor | Flavoring | 15.0 |
| Copovidone | Binder | 3.3 |
| PEG 4000 | Binder | 5.5 |
| Polyoxyl 60 hydrogenated castor oil | Surfactant | 4.0 |
| Glycerin | Humectant | 5.1 |
| Potassium Sorbate | Preservative | 0.3 |
| Propylene glycol dicaprylate/dicaprate | Solvent/Lubricant | 3.2 |
| PEG 400 | Solvent | 5.4 |

TABLE 6

| Ingredients | Function | % (w/w) |
| --- | --- | --- |
| Cmpd. A | Active | 1.5 |
| Soy Protein Fines | Filler | 46.5 (QS) |
| beef flavor | Flavoring | 20.0 |
| Povidone K-30 | Binder | 7.0 |
| PEG 400 | Solvent | 15 |
| polyethylene glycol 12-hydroxystearate | Surfactant | 3.0 |
| Caprylic/capric triglyceride | Solvent/lubricant | 7.0 |

TABLE 7

| Ingredients | Function | % (w/w) |
| --- | --- | --- |
| Cmpd. A | Active | 1.875 |
| Soy Protein Fines | Filler | 46.1 (QS) |
| beef flavor | Flavoring | 20.0 |
| Povidone K-30 | Binder | 8.5 |
| PEG 400 | Solvent | 15.5 |
| polyethylene glycol 12-hydroxystearate | Surfactant | 3.0 |
| Caprylic/capric triglyceride | Solvent/lubricant | 5.0 |

TABLE 8

| Ingredients | Function | % (w/w) |
| --- | --- | --- |
| Cmpd. A | Active | 1.875 |
| Soy Protein Fines | Filler | 36.1 (QS) |
| beef flavor | Flavoring | 20.0 |
| Povidone K-30 | Binder | 8.5 |
| PEG 400 | Solvent | 15.5 |
| polyethylene glycol 12-hydroxystearate | Surfactant | 3.0 |
| Caprylic/capric triglyceride | Solvent/lubricant | 5.0 |
| Croscarmellose sodium | disintegrant | 10.0 |

TABLE 9

| Ingredients | Function | % (w/w) |
| --- | --- | --- |
| Cmpd. A | Active | 2.3 |
| Soy Protein Fines | Filler | 20.6 (QS) |
| Corn Starch | Filler | 25.0 |
| beef flavor | Flavoring | 20.5 |
| Povidone K-30 | Binder | 2.8 |
| PEG 400 | Solvent | 7.2 |
| PEG 4000 | Binder | 6.4 |
| polyethylene glycol 12-hydroxystearate | Surfactant | 3.1 |
| Glycerin | Humectant | 8.6 |
| Potassium Sorbate | Preservative | 0.3 |
| Caprylic/capric triglyceride | Solvent/Lubricant | 3.1 |

TABLE 10

| Ingredients | Function | % (w/w) |
| --- | --- | --- |
| Cmpd. A | Active | 2.3 |
| Soy Protein Fines | Filler | 20.0 (QS) |
| Corn Starch | Filler | 25.0 |

TABLE 10-continued

| Ingredients | Function | % (w/w) |
|---|---|---|
| beef flavor | Flavoring | 20.0 |
| Povidone K-30 | Binder | 2.8 |
| PEG 400 | Solvent | 7.1 |
| PEG 4000 | Binder | 6.4 |
| polyethylene glycol 12-hydroxystearate | Surfactant | 3.1 |
| Glycerin | Humectant | 10.0 |
| Potassium Sorbate | Preservative | 0.3 |
| Caprylic/capric triglyceride | Solvent/Lubricant | 3.2 |

TABLE 11

| Ingredients | Function | % (w/w) |
|---|---|---|
| Milbemycin oxime | Active | 0.375 |
| Soy Protein Fines | Filler | 21.0 (QS) |
| Corn Starch | Filler | 25.7 |
| beef flavor | Flavoring | 20.2 |
| Povidone K-30 | Binder | 2.7 |
| PEG 400 | Solvent | 7.1 |
| PEG 4000 | Binder | 6.3 |
| polyethylene glycol 12-hydroxystearate | Surfactant | 3.0 |
| Glycerin | Humectant | 10.1 |
| Caprylic/capric triglyceride | Solvent/Lubricant | 3.1 |
| Potassium Sorbate | Preservative | 0.3 |
| BHT | Antioxidant | 0.14 |

TABLE 12

| Ingredients | Function | % (w/w) |
|---|---|---|
| Cmpd. A | Active | 1.89 |
| Milbemycin oxime | Active | 0.375 |
| Soy Protein Fines | Filler | 20.0 (QS) |
| Corn Starch | Filler | 24.7 |
| beef flavor | Flavoring | 20.2 |
| Povidone K-30 | Binder | 2.7 |
| PEG 400 | Solvent | 7.1 |
| PEG 4000 | Binder | 6.3 |
| polyethylene glycol 12-hydroxystearate | Surfactant | 3.0 |
| Glycerin | Humectant | 10.1 |
| Caprylic/capric triglyceride | Solvent/Lubricant | 3.1 |
| Potassium Sorbate | Preservative | 0.3 |
| BHT | Antioxidant | 0.14 |

TABLE 13

| Ingredients | Function | % (w/w) |
|---|---|---|
| Cmpd. A | Active | 1.875 |
| Milbemycin oxime | Active | 0.375 |
| Soy Protein Fines | Filler | 19.4 (QS) |
| Corn Starch | Filler | 25.0 |
| beef flavor | Flavoring | 20.0 |
| Povidone K-30 | Binder | 2.75 |
| PEG 400 | Solvent | 7.1 |
| PEG 4000 | Binder | 6.35 |
| polyethylene glycol 12-hydroxystearate | Surfactant | 3.1 |
| Glycerin | Humectant | 10.0 |
| Caprylic/capric triglyceride | Solvent/Lubricant | 3.15 |
| Potassium Sorbate | Preservative | 0.3 |
| BHT | Antioxidant | 0.14 |
| Citric Acid Monohydrate | pH modifier | 0.50 |

TABLE 14

| Ingredients | Function | % (w/w) |
|---|---|---|
| Cmpd. A | Active | 1.875 |
| Milbemycin oxime | Active | 0.375 |
| Soy Protein Fines | Filler | 20.5 (QS) |
| Corn Starch | Filler | 24.0 |
| beef flavor | Flavoring | 20.0 |
| Copovidone | Binder | 2.75 |
| PEG 300 | Solvent | 8.0 |
| PEG 4000 | Binder | 6.35 |
| Polyoxyl 60 hydrogenated castor oil | Surfactant | 3.1 |
| Glycerin | Humectant | 10.0 |
| Propylene glycol dicaprylate/dicaprate | Solvent/Lubricant | 2.15 |
| Potassium Sorbate | Preservative | 0.3 |
| BHT | Antioxidant | 0.14 |
| Citric Acid Monohydrate | pH modifier | 0.50 |

TABLE 15

| Ingredients | Function | % (w/w) |
|---|---|---|
| Cmpd. A | Active | 1.875 |
| Ivermectin | Active | 0.375 |
| Soy Protein Fines | Filler | 29.4 (QS) |
| Pre-gelatinized corn starch | Filler | 15.0 |
| beef flavor | Flavoring | 20.0 |
| Copovidone | Binder | 2.75 |
| Caprylate/caprate glyceride | Solvent | 8.0 |
| PEG 4000 | Binder | 6.35 |
| polyoxyl 35 castor oil (Cremophor ® EL) | Surfactant | 3.1 |
| Propylene glycol | Humectant | 10.0 |
| Propylene glycol dicaprylate/dicaprate | Solvent/Lubricant | 2.2 |
| Potassium Sorbate | Preservative | 0.3 |
| BHT | Antioxidant | 0.14 |
| Citric Acid Monohydrate | pH modifier | 0.50 |

TABLE 16

| Ingredients | Function | % (w/w) |
|---|---|---|
| Cmpd. A | Active | 2.2 |
| moxidectin | Active | 0.50 |
| Soy Protein Fines | Filler | 29.4 (QS) |
| Pre-gelatinized corn starch | Filler | 15.0 |
| beef flavor | Flavoring | 20.0 |
| Povidone K30 | Binder | 2.75 |
| Caprylate/caprate glyceride | Solvent | 8.0 |
| PEG 4000 | Binder | 6.0 |
| Polyoxyl 40 hydrogenated castor oil (Cremophor ® RH40) | Surfactant | 3.1 |
| Propylene glycol | Humectant/Solvent | 10.0 |
| Propylene glycol dicaprylate/dicaprate | Solvent/Lubricant | 2.2 |
| Potassium Sorbate | Preservative | 0.3 |
| BHT | Antioxidant | 0.14 |
| Citric Acid Monohydrate | pH modifier | 0.50 |

TABLE 17

| Ingredients | Function | % (w/w) |
|---|---|---|
| Cmpd. A | Active | 0.5 |
| Soy Protein Fines | Filler | 16.6 |
| Corn Starch | Filler | 32.5 (QS) |
| beef flavor | Flavoring | 19.4 |
| Povidone K-30 | Binder | 2.6 |
| PEG 400 | Solvent | 7.8 |
| PEG 4000 | Binder | 6.1 |
| polyethylene glycol 12-hydroxystearate | Surfactant | 4.7 |
| Lauroyl polyoxyl-32 glycerides | Surfactant | 4.7 |
| Potassium Sorbate | Preservative | 0.3 |
| Caprylic/capric triglyceride | Solvent/Lubricant | 4.9 |

TABLE 18

| Ingredients | Function | % (w/w) |
| --- | --- | --- |
| Cmpd. A | Active | 0.5 |
| Soy Protein Fines | Filler | 19.4 |
| Pre-gelatinized corn Starch | Filler | 29.7 (QS) |
| beef flavor | Flavoring | 18.0 |
| Copovidone | Binder | 3.0 |
| PEG 540 | Solvent | 8.3 |
| PEG 4000 | Binder | 6.1 |
| Polyoxyl 60 hydrogenated castor oil (Cremophor ® RH60) | Surfactant | 5.1 |
| Lauroyl polyoxyl-32 glycerides | Surfactant | 4.7 |
| Potassium Sorbate | Preservative | 0.3 |
| Caprylic/capric triglyceride | Solvent/Lubricant | 4.9 |

TABLE 19

| Ingredients | Function | % (w/w) |
| --- | --- | --- |
| Cmpd. A | Active | 0.5 |
| Soy Protein Fines | Filler | 26.9 (QS) |
| Corn Starch | Filler | 23.4 |
| beef flavor | Flavoring | 20.0 |
| PEG 400 | Solvent | 6.8 |
| PEG 4000 | Binder | 5.8 |
| polyethylene glycol 12-hydroxystearate | Surfactant | 4.8 |
| Lauroyl polyoxyl-32 glycerides | Surfactant | 6.3 |
| Potassium Sorbate | Preservative | 0.3 |
| Caprylic/capric triglyceride | Solvent/Lubricant | 5.2 |

TABLE 20

| Ingredients | Function | % (w/w) |
| --- | --- | --- |
| Cmpd. A | Active | 0.5 |
| Soy Protein Fines | Filler | 24.3 (QS) |
| Pre-gelatinized corn starch | Filler | 26.0 |
| beef flavor | Flavoring | 19.0 |
| PEG 540 | Solvent | 6.8 |
| Crospovidone | Binder | 5.8 |
| polyoxyl 35 castor oil (Cremophor ® EL) | Surfactant | 5.2 |
| Lauroyl polyoxyl-32 glycerides | Surfactant | 6.9 |
| Potassium Sorbate | Preservative | 0.3 |
| Caprylic/capric triglyceride | Solvent/Lubricant | 5.2 |

TABLE 21

| Ingredients | Function | % (w/w) |
| --- | --- | --- |
| Cmpd. A | Active | 0.5 |
| Soy Protein Fines | Filler | 41.6 (QS) |
| beef flavor | Flavoring | 19.9 |
| Povidone K-30 | Binder | 4.6 |
| PEG 400 | Solvent | 15.1 |
| PEG 4000 | Binder | 8.1 |
| polyethylene glycol 12-hydroxystearate | Surfactant | 4.6 |
| Potassium Sorbate | Preservative | 0.3 |
| Caprylic/capric triglyceride | Solvent/Lubricant | 4.6 |

TABLE 22

| Ingredients | Function | % (w/w) |
| --- | --- | --- |
| Cmpd. A | Active | 0.5 |
| Soy Protein Fines | Filler | 44.2 (QS) |
| beef flavor | Flavoring | 18.0 |
| Povidone K-30 | Binder | 4.6 |
| PEG 400 | Solvent | 15.1 |
| Cross-linked polyvinylpyrrolidone | Binder | 7.1 |
| propylene glycol monolaurate | Surfactant | 4.6 |
| Potassium Sorbate | Preservative | 0.3 |
| Caprylic/capric triglyceride | Solvent/Lubricant | 5.6 |

TABLE 23

| Ingredients | Function | % (w/w) |
| --- | --- | --- |
| Cmpd. A | Active | 0.5 |
| Corn Starch | Filler | 40.8 (QS) |
| beef flavor | Flavoring | 19.9 |
| Povidone K-30 | Binder | 5.7 |
| PEG 400 | Solvent | 11.4 |
| PEG 4000 | Binder | 5.7 |
| polyethylene glycol 12-hydroxystearate | Surfactant | 2.7 |
| Lauroyl polyoxyl-32 glycerides | Surfactant | 2.7 |
| Potassium Sorbate | Preservative | 0.3 |
| Caprylic/capric triglyceride | Solvent/Lubricant | 5.4 |
| Sodium Starch glycolate | Disintegrate | 5.0 |

TABLE 24

| Ingredients | Function | % (w/w) |
| --- | --- | --- |
| Cmpd. A | Active | 0.5 |
| Soy Protein Fines | Filler | 19.4 |
| Corn Starch | Filler | 24.0 (QS) |
| beef flavor | Flavoring | 19.2 |
| Povidone K-30 | Binder | 2.6 |
| PEG 400 | Solvent | 8.6 |
| PEG 4000 | Binder | 6.0 |
| polyethylene glycol 12-hydroxystearate | Surfactant | 4.6 |
| Lauroyl polyoxyl-32 glycerides | Surfactant | 4.6 |
| Potassium Sorbate | Preservative | 0.3 |
| Caprylic/capric triglyceride | Solvent/Lubricant | 5.3 |
| Glycerin | Humectant | 4.8 |

TABLE 25

| Ingredients | Function | % (w/w) |
| --- | --- | --- |
| Cmpd. A | Active | 2.3 |
| Soy Protein Fines | Filler | 22.0 (QS) |
| Corn Starch | Filler | 26.4 |
| beef flavor | Flavoring | 10.0 |
| Artificial Powdered Meat Flavor | Flavoring | 10.0 |
| Povidone K-30 | Binder | 2.7 |
| PEG 400 | Solvent | 7.0 |
| PEG 4000 | Binder | 6.25 |
| polyethylene glycol 12-hydroxystearate | Surfactant | 3.0 |
| Glycerin | Humectant | 7.0 |
| Potassium Sorbate | Preservative | 0.3 |
| Caprylic/capric triglyceride | Solvent/Lubricant | 3.0 |

TABLE 26

| Ingredients | Function | % (w/w) |
| --- | --- | --- |
| Cmpd. A | Active | 13.6 |
| Soy Protein Fines | Filler | 15-25 (QS) |
| Corn Starch | Filler | 15-25 |
| beef flavor | Flavoring | 20 |
| PEG 400 | Solvent | 11.9 |
| PEG 4000 | Binder | 5 |
| polyethylene glycol 12-hydroxystearate | Surfactant | 3-5 |
| Glycerin | Humectant | 2-5 |
| Potassium Sorbate | Preservative | 0.3 |

TABLE 27

| Ingredients | Function | % (w/w) |
| --- | --- | --- |
| Cmpd. A | Active | 13.6 |
| Corn Starch | Filler | 41 (QS) |
| beef flavor | Flavoring | 15-25 |
| PEG 400 | Solvent | 11.9 |
| Cross-linked polyvinylpyrrolidone | Binder | 5 |
| polyoxyl 35 castor oil | Surfactant | 3-5 |
| Propylene glycol | Humectant | 2-5 |
| Potassium Sorbate | Preservative | 0.3 |

TABLE 28

| Ingredients | Function | % (w/w) |
| --- | --- | --- |
| Cmpd. A | Active | 13.6 |
| Soy Protein Fines | Filler | 12.6 |
| Corn Starch | Filler | 25 (QS) |
| beef flavor | Flavoring | 20 |
| Povidone K-30 | Binder | 2.75 |
| PEG 400 | Solvent | 5.5 |
| PEG 4000 | Binder | 6.2 |
| polyethylene glycol 12-hydroxystearate | Surfactant | 5.0 |
| Glycerin | Humectant | 7-8 |
| Potassium Sorbate | Preservative | 0.3 |
| Caprylic/capric triglyceride | Solvent/Lubricant | 2.0 |

TABLE 29

| Ingredients | Function | % (w/w) |
| --- | --- | --- |
| Cmpd. A | Active | 13.6 |
| Soy protein fines | Filler | 25.0 (QS) |
| Corn Starch | Filler | 15-18 |
| beef flavor | Flavoring | 20 |
| PEG 400 | Solvent | 11.9 |
| Cross-linked polyvinylpyrrolidone | Binder | 5 |
| polyoxyl 35 castor oil | Surfactant | 3-5 |
| Propylene glycol | Humectant | 2-5 |
| Potassium Sorbate | Preservative | 0.3 |

TABLE 30

| Ingredients | Function | % (w/w) |
| --- | --- | --- |
| Cmpd. A | Active | 13.6 |
| Soy protein fines | Filler | 15.2 (QS) |
| Corn Starch | Filler | 25 |
| beef flavor | Flavoring | 20 |
| PEG 400 | Solvent | 11.9 |
| PEG 4000 | Binder | 5.0 |
| polyethylene glycol 12-hydroxystearate | Surfactant | 5.0 |
| Caprylic/capric triglyceride | Solvent/lubricant | 1.0 |
| Glycerin | Humectant | 3.0 |
| Potassium Sorbate | Preservative | 0.3 |

TABLE 31

| Ingredients | Function | % (w/w) |
| --- | --- | --- |
| Cmpd. A | Active | 13.6 |
| Soy protein fines | Filler | 19.2 (QS) |
| Corn Starch | Filler | 20 |
| beef flavor | Flavoring | 20 |
| PEG 400 | Solvent | 11.9 |
| PEG 4000 | Binder | 5.0 |
| polyethylene glycol 12-hydroxystearate | Surfactant | 5.0 |
| Caprylic/capric triglyceride | Solvent/lubricant | 1.0 |
| Glycerin | Humectant | 4.0 |
| Potassium Sorbate | Preservative | 0.3 |

TABLE 32

| Ingredients | Function | % (w/w) |
| --- | --- | --- |
| Cmpd. A | Active | 13.6 |
| Soy protein fines | Filler | 24.2 (QS) |
| Corn Starch | Filler | 15 |
| beef flavor | Flavoring | 20 |
| PEG 400 | Solvent | 11.9 |
| PEG 4000 | Binder | 5.0 |
| polyethylene glycol 12-hydroxystearate | Surfactant | 5.0 |
| Caprylic/capric triglyceride | Solvent/lubricant | 1.0 |
| Glycerin | Humectant | 4.0 |
| Potassium Sorbate | Preservative | 0.3 |

TABLE 33

| Ingredients | Function | % (w/w) |
| --- | --- | --- |
| Milbemycin oxime | Active | 0.375 |
| Soy protein fines | Filler | 47.7 (QS) |
| beef flavor | Flavoring | 20.0 |
| Povidone K-30 | Binder | 7.5 |
| PEG 400 | Solvent | 16.0 |
| polyethylene glycol 12-hydroxystearate | Surfactant | 3.0 |
| Caprylic/capric triglyceride | Solvent/lubricant | 5.0 |
| Potassium sorbate | Preservative | 0.3 |
| BHT | Antioxidant | 0.14 |

TABLE 34

| Ingredients | Function | % (w/w) |
| --- | --- | --- |
| Compound A | Active | 1.875 |
| Milbemycin oxime | Active | 0.375 |
| Corn starch | Filler | 20.0 |
| Soy protein fines | Filler | 28.3 (QS) |
| beef flavor | Flavoring | 25.0 |
| Povidone K-30 | Binder | 6.0 |
| PEG 400 | Solvent | 12.0 |
| polyethylene glycol 12-hydroxystearate | Surfactant | 3.0 |
| Caprylic/capric triglyceride | Solvent/lubricant | 3.0 |
| Potassium sorbate | Preservative | 0.3 |
| BHT | Antioxidant | 0.14 |

TABLE 35

| Ingredients | Function | % (w/w) |
| --- | --- | --- |
| Milbemycin oxime | Active | 0.375 |
| Soy protein fines | Filler | 21 (QS) |
| Starch | Filler | 25 |
| beef flavor | Flavoring | 20 |
| Povidone K-30 | Binder | 2.75 |
| PEG 400 | Solvent | 7.1 |
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

TABLE 36

| Ingredients | Function | % (w/w) |
| --- | --- | --- |
| Moxidectin | Active | 0.03 |
| Soy protein fines | Filler | 21 (QS) |
| Starch | Filler | 25 |
| beef flavor | Flavoring | 20 |
| Povidone K-30 | Binder | 2.75 |
| PEG 400 | Solvent | 7.1 |

TABLE 36-continued

| Ingredients | Function | % (w/w) |
|---|---|---|
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

TABLE 37

| Ingredients | Function | % (w/w) |
|---|---|---|
| Ivermectin | Active | 0.02 |
| Soy protein fines | Filler | 21 |
| Starch | Filler | 25 |
| beef flavor | Flavoring | 20 |
| Povidone K-30 | Binder | 2.75 |
| PEG 400 | Solvent | 7.1 |
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

TABLE 38

| Ingredients | Function | % (w/w) |
|---|---|---|
| Moxidectin | Active | 0.03 |
| Milbemycin oxime | Active | 0.375 |
| Compound A | Active | 1.875 |
| Soy protein fines | Filler | 23 (QS) |
| Starch | Filler | 21 |
| beef flavor | Flavoring | 20 |
| Povidone K-30 | Binder | 2.75 |
| PEG 400 | Solvent | 7.1 |
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

TABLE 39

| Ingredients | Function | % (w/w) |
|---|---|---|
| Moxidectin | Active | 0.015 |
| Soy protein fines | Filler | 21 (QS) |
| Starch | Filler | 25 |
| beef flavor | Flavoring | 20 |
| Povidone K-30 | Binder | 2.75 |
| PEG 400 | Solvent | 7.1 |
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

TABLE 40

| Ingredients | Function | % (w/w) |
|---|---|---|
| Praziquantel | Active | 1.875 |
| Febantel | Active | 9.375 |
| Soy protein fines | Filler | 44.23 (QS) |
| beef flavor | Flavoring | 15 |
| Povidone K-30 | Binder | 6 |
| Propylene glycol | Solvent | 7.0 |
| polyoxyl 40 hydrogenated castor oil | Surfactant | 4 |
| Ethanol | Solvent | 5 |
| Caprylic/capric triglyceride | Solvent/lubricant | 6 |
| Tocopherol | Antioxidant | 1 |
| Potassium sorbate | Preservative | 0.30 |
| BHT | Antioxidant | 0.14 |

TABLE 41

| Ingredients | Function | % (w/w) |
|---|---|---|
| Praziquantel | Active | 1.875 |
| Febantel | Active | 9.375 |
| Moxidectin | Active | 0.075 |
| Soy protein fines | Filler | 44.16 (QS) |
| beef flavor | Flavoring | 15 |
| Povidone K-30 | Binder | 6 |
| Propylene glycol | Solvent | 7.0 |
| polyoxyl 40 hydrogenated castor oil | Surfactant | 4 |
| Ethanol | Solvent | 5 |
| Caprylic/capric triglyceride | Solvent/lubricant | 6 |
| Tocopherol | Antioxidant | 1 |
| Potassium sorbate | Preservative | 0.30 |
| BHT | Antioxidant | 0.14 |

TABLE 42

| Ingredients | Function | % (w/w) |
|---|---|---|
| Praziquantel | Active | 1.875 |
| Febantel | Active | 9.375 |
| Milbemycin oxime | Active | 0.375 |
| Soy protein fines | Filler | 43.85 (QS) |
| beef flavor | Flavoring | 15 |
| Povidone K-30 | Binder | 6 |
| Propylene glycol | Solvent | 7.0 |
| polyoxyl 40 hydrogenated castor oil | Surfactant | 4 |
| Ethanol | Solvent | 5 |
| Caprylic/capric triglyceride | Solvent/lubricant | 6 |
| Tocopherol | Antioxidant | 1 |
| Potassium sorbate | Preservative | 0.30 |
| BHT | Antioxidant | 0.14 |

TABLE 43

| Ingredients | Function | % (w/w) |
|---|---|---|
| Milbemycin oxime | Active | 0.375 |
| Soy protein fines | Filler | 47.69 (QS) |
| beef flavor | Flavoring | 20 |
| Povidone K-30 | Binder | 7.5 |
| PEG 400 | Solvent | 16.0 |
| polyethylene glycol 12-hydroxystearate | Surfactant | 3.0 |
| Caprylic/capric triglyceride | Solvent/lubricant | 5 |
| Potassium sorbate | Preservative | 0.30 |
| BHT | Antioxidant | 0.14 |

TABLE 44

| Ingredients | Function | % (w/w) |
|---|---|---|
| Milbemycin oxime | Active | 0.375 |
| Soy protein fines | Filler | 47.69 (QS) |

TABLE 44-continued

| Ingredients | Function | % (w/w) |
| --- | --- | --- |
| beef flavor | Flavoring | 20 |
| Povidone K-30 | Binder | 7.5 |
| Propylene glycol | Solvent | 16.0 |
| polyoxyl 40 hydrogenated castor oil | Surfactant | 3.0 |
| Caprylic/capric triglyceride | Solvent/lubricant | 5 |
| Potassium sorbate | Preservative | 0.30 |
| BHT | Antioxidant | 0.14 |

TABLE 45

| Ingredients | Function | % (w/w) |
| --- | --- | --- |
| Milbemycin oxime | Active | 0.375 |
| Soy protein fines | Filler | 21.24 (QS) |
| Corn starch | Filler | 25 |
| beef flavor | Flavoring | 20 |
| Povidone K-30 | Binder | 2.75 |
| PEG 400 | Solvent | 7.1 |
| PEG 4000 | Binder | 6.35 |
| polyethylene glycol 12-hydroxystearate | Surfactant | 3.1 |
| Glycerin | Humectant | 10 |
| Caprylic/capric triglyceride | Solvent/lubricant | 3.15 |
| Potassium sorbate | Preservative | 0.30 |
| BHT | Antioxidant | 0.14 |

TABLE 46

| Ingredients | Function | % (w/w) |
| --- | --- | --- |
| Ivermectin | Active | 0.015 |
| Milbemycin oxime | Active | 0.375 |
| Compound A | Active | 1.875 |
| Soy protein fines | Filler | 19.3 (QS) |
| Corn starch | Filler | 25 |
| beef flavor | Flavoring | 20 |
| Povidone K-30 | Binder | 2.75 |
| PEG 400 | Solvent | 7.1 |
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

TABLE 47

| Ingredients | Function | % (w/w) |
| --- | --- | --- |
| Ivermectin | Active | 0.015 |
| Milbemycin oxime | Active | 0.375 |
| Soy protein fines | Filler | 21.2 (QS) |
| Corn starch | Filler | 25 |
| beef flavor | Flavoring | 20 |
| Povidone K-30 | Binder | 2.75 |
| PEG 400 | Solvent | 7.1 |
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

TABLE 48

| Ingredients | Function | % (w/w) |
| --- | --- | --- |
| Moxidectin | Active | 0.03 |
| Milbemycin oxime | Active | 0.375 |
| Compound A | Active | 1.875 |
| Soy protein fines | Filler | 19.3 (QS) |
| Corn starch | Filler | 25 |
| beef flavor | Flavoring | 20 |
| Povidone K-30 | Binder | 2.75 |
| PEG 400 | Solvent | 7.1 |
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

TABLE 49

| Ingredients | Function | % (w/w) |
| --- | --- | --- |
| Moxidectin | Active | 0.03 |
| Milbemycin oxime | Active | 0.375 |
| Soy protein fines | Filler | 21.2 (QS) |
| Corn starch | Filler | 25 |
| beef flavor | Flavoring | 20 |
| Povidone K-30 | Binder | 2.75 |
| PEG 400 | Solvent | 7.1 |
| polyethylene glycol 12-hydroxystearate | Surfactant | 3.1 |
| PEG 4000 | Binder | 6.35 |
| Caprylic/capric triglyceride | Solvent/lubricant | 3.15 |
| Glycerin | Humectant | 10.0 |
| Potassium sorbate | Preservative | 0.3 |
| BHT | Antioxidant | 0.14 |
| Citric acid | Preservative | 0.5 |

Example 2

Efficacy of Soft Chewable Compositions Comprising Compound A Against Fleas (*Ctenocephalides felis*) and Ticks (*Dermacentor variabilis*) on Dogs Sixteen beagles were studied to determine the effectiveness of a soft chewable veterinary composition comprising Compound A against induced infestations of *Dermacentor variabilis* and *Ctenocephalides felis*.

Four Treatment Groups containing four dogs each were formed. Dogs in Group 1 were untreated. Dogs in Groups 2, 3 and 4 were treated with the soft chewable composition described in Table 6 of nominal sizes of 0.5 g and 1 g containing Compound A at concentrations of 7.35 mg/chew and 14.7 mg/chew, respectively, to deliver doses of approximately 1.5 mg/kg, 2.5 mg/kg or 3.5 mg/kg. All dogs were treated once on Day 0.

All dogs were infested with approximately 100 *C. felis* on Days—1, 8, 15, 22, 29, 35, 43, 57 and 71. All dogs were also infested with approximately 50 *D. variabilis* on Days—1, 7, 14, 21, 28, 34 and 42. Both ticks and fleas were counted upon removal on Days 2, 9, 16, 23, 30, 36 and 44. Fleas were counted upon removal for all Treatment Groups on Days 58 and 72. Flea efficacy is listed in Table 50 and tick efficacy is listed in Table 51 below.

Percent reduction (also referred as efficacy) against fleas was 100% through and including Day 30 for all treatment groups (see Table 50). Percent reduction against fleas was above 95% through Day 44 for all groups and above 95% through Day 58 for Groups 3 and 4.

The percent reduction against ticks was >90% through and including Day 30 (see Table 51) for all treatment groups and remained above 90% through Day 36 for Groups 3 and 4.

These study data demonstrate that soft chewable compositions comprising an isoxazoline compound (Cmpd. A) at three different doses provides excellent efficacy against fleas and ticks in dogs.

TABLE 50

Flea Efficacy

| Treatment Study Group[1] | % Reduction Fleas | | | | | | | | |
|---|---|---|---|---|---|---|---|---|---|
| | Day 2 | Day 9 | Day 16 | Day 23 | Day 30 | Day 36 | Day 44 | Day 58 | Day 72 |
| Group 2 | | | | | | | | | |
| % Reduction | 100.0 | 100.0 | 100.0 | 100.0 | 100.0 | 99.2 | 97.8 | 89.4 | 79.6 |
| Group 3 | | | | | | | | | |
| % Reduction | 100.0 | 100.0 | 100.0 | 100.0 | 100.0 | 100.0 | 99.3 | 96.7 | 94.4 |
| Group 4 | | | | | | | | | |
| % Reduction | 100.0 | 100.0 | 100.0 | 100.0 | 100.0 | 99.6 | 98.3 | 95.2 | 80.6 |

TABLE 51

Tick Efficacy

| Treatment Group[1] | % Reduction Ticks | | | | | | |
|---|---|---|---|---|---|---|---|
| | Day 2 | Day 9 | Day 16 | Day 23 | Day 30 | Day 36 | Day 44 |
| Group 2 | | | | | | | |
| % Reduction | 100.0 | 99.2 | 100.0 | 92.1 | 99.5 | 82.4 | 68.3 |
| Group 3 | | | | | | | |
| % Reduction | 100.0 | 100.0 | 99.1 | 97.2 | 94.3 | 96.9 | 88.1 |
| Group 4 | | | | | | | |
| % Reduction | 100.0 | 100.0 | 99.5 | 100.0 | 98.1 | 91.9 | 84.7 |

Example 3

Efficacy and Speed of Kill Efficacy of Soft Chewable Compositions Comprising Compound A Against Fleas (*Ctenocephalides felis*) on Dogs Following a procedure very similar to that described in Example 2 above, beagles were studied to determine the effectiveness and speed of kill against induced infestations of *Ctenocephalides felis*.

Three Treatment Groups were formed. Dogs in Group 1 were untreated. Dogs in Groups 2 and 3 were treated with the soft chewable compositions containing Compound A described in Tables 7 and 8, respectively, at concentrations to deliver a dose of approximately 2.5 mg/kg. Groups 1 and 2 contained 12 dogs each and Group 3 contained 4 dogs. All dogs were treated once on Day 0.

All dogs were infested with approximately 75 *C. felis* on Days 0 and 7. The dogs in Group 3 and dogs in pre-allocated subgroups in Groups 1 and 2 were also infested with approximately 75 *C. felis* on Days 14, 21 and 28. Fleas were counted upon removal from selected subjects at 30 minutes, 4 hours, and 12 hours after treatment or infestation on Days 0 and 7. On Days 14, 21 and 28, fleas were counted upon removal from selected subjects at 8 and 12 hours after infestation. The data shows that the compositions started working within 30 minutes after treatment on Day 0 and that 12 hours after administration of the composition, flea efficacy of 100% was observed. Following infestation at later timepoints, the composition started working within 30 minutes, and by 12 hours after infestation on Days 7, 14 and 21, efficacy of >98% was achieved.

Example 4

Efficacy of Soft Chewable Compositions Comprising Compound A Against *Amblyomma americanum* Ticks on Dogs Following a procedure very similar to that described in Example 2 above with the chewable formulation described in Table 10, sixteen beagles were studied to determine the effectiveness of a soft chewable veterinary composition comprising Compound A against induced infestations of *Amblyomma americanum* (lone star tick).

Two treatment groups were formed, each containing eight dogs each. Dogs in Group 1 were untreated. Dogs in Group 2 were treated once on Day 0 with soft chewable compositions containing Compound A at a concentration to deliver a dose of at least approximately 2.5 mg/kg.

Dogs in both groups were infested with approximately 50 *Amblyomma americanum* on Days—1, 7, 14, 21, 28 and 35. Ticks were counted on Days 2, 9, 16, 23, 30 and 38. The percent efficacy of the treated group versus the untreated control group 48 hours after infestation exceeded 91% at Days 2, 9, 16 and 23, with percent efficacy values of 99.2, 98.7, 99.4 and 91.7, respectively (p-values≤0.001). At Day 38 the percent efficacy was measured at 89.7%. The study demonstrates that the chewable compositions of the invention provided excellent control of *Amblyomma americanum* in excess of 30 days.

Example 5

Efficacy of Soft Chewable Compositions Comprising Compound A Against *Ixodes holocyclus* Ticks on Dogs Following a procedure very similar to that described in Example 2 and Example 3 above with the chewable formulations described in Tables 10 and 13, twenty four foxhounds were studied to determine the effectiveness of two soft chewable veterinary compositions comprising Compound A alone and Compound A in combination with milbemycin oxime (Tables 10 and 13, respectively), against induced infestations of *Ixodes holocyclus*. Three treatment groups consisting of eight dogs each were formed. Group 1 was an untreated control. The dogs in Group 2 were treated on Day 0 with a soft chewable composition comprising Compound A alone to deliver a dose of at least 2.5 mg/kg body weight and dogs in Group 3 were treated on Day 0 with a soft chewable composition comprising a combination of Compound A and milbemycin oxime to deliver doses of at least 2.5 mg/kg of body weight of Compound A and at least 0.5 mg/kg of body weight of milbemycin oxime.

Dogs in the three groups were infested with approximately 50 *Ixodes* holocyclus on Days—1, 7, 14, 21, 28 and 35. Ticks were counted on at 24 hours, 48 hours and 72 hours post infestation on Days 1, 2, 3, 8, 9, 10, 15, 16, 17, 22, 23, 24, 29, 30, 31, 36, 37 and 38.

Treatment Group 2 (Compound A alone) exhibited a percent efficacy of at least 99.2% at 72 hours post infestation at all time points measured. At 48 hours post infestation, dogs in Group 2 had percent efficacies of at least 98.7% at all time points measured. At 24 hours post infestation, dogs in Group 2 had efficacies of at least 95.8% on Days 1, 8, 15 and 22.

Treatment Group 3 (Compound A and milbemycin oxime) exhibited an efficacy of at least 98.6% 72 hours post infestation at all time points. At 48 hours post infestation, dogs in Group 3 demonstrated an efficacy of at least 99.1% for all time points. At 24 hours post infestation, dogs in Group 3 had efficacies of at least 96.1% for all time points. This example demonstrates the exceptional efficacy of the soft chewable compositions of the invention against ticks for duration of at least 38 days post treatment. The extent and duration of efficacy from one oral dose is exceptional and surprising.

Example 6

Long Lasting Efficacy of Soft Chewable Composition Containing Compound A Against *Amblyomma americanum* and *Dermacentor variabilis* on Dogs The efficacy of a soft chewable composition of the invention comprising a higher concentration of the active agent against two tick species was evaluated using a procedure similar to that described in Examples 2 and 3 above with the chewable formulations described in Tables 30, 31 and 32. Forty two beagles were allotted to seven groups of six dogs each. Groups 1 and 2 served as untreated controls. Groups 3, 4 and 5 were each treated on Day 0 with three different compositions of the invention described in Tables 30, 31 and 32, respectively, containing Compound A in an amount to deliver a dose of about 20 mg/kg of body weight. Similarly, on Day 0, Groups 6 and 7 were each treated with the compositions described in Tables 30 and 32, respectively, containing Compound A to deliver a dose of about 20 mg/kg of body weight.

Dogs in Groups 1, 3, 4 and 5 were infested with approximately 50 *A. americanum* and dogs in Groups 2, 6 and 7 were infested with approximately 50 *D. variabilis* on Days—1, 42, 56, 70, 77, 84, 91 and 98. Dogs in Groups 1, 2, 3, 6 and 7 were also infested on Day 105. Ticks were counted upon removal at approximately 48 hours post treatment on Day 2 and 48 hours post infestation on Days 44, 58, 72, 79, 86, 93, 100 and 107. Tables 52 and 53 below show the exceptional long-lasting efficacy of the inventive compositions against *A. americanum* and *D. variabilis*. The efficacy exhibited against these two tick species is remarkable considering that the dogs were treated only once on Day 0.

TABLE 52

Efficacy Against *A. americanum*

| | % Reduction Ticks | | | | | | | | |
|---|---|---|---|---|---|---|---|---|---|
| Treatment Group[1] | Day 2 | Day 44 | Day 58 | Day 72 | Day 79 | Day 86 | Day 93 | Day 100 | Day 107 |
| Group 3 | | | | | | | | | |
| % Reduction | 100.0 | 98.4 | 98.8 | 99.5 | 94.4 | 98.9 | 99.5 | 95.6 | 93.4 |
| Group 4 | | | | | | | | | |
| % Reduction | 100.0 | 99.4 | 99.4 | 97.7 | 88.6 | 97.5 | 97.7 | 90.9 | |
| Group 5 | | | | | | | | | |
| % Reduction | 100.0 | 100.0 | 99.5 | 100.0 | 98.8 | 97.8 | 98.2 | 87.8 | |

TABLE 53

Efficacy Against *D. variabilis*

| | % Reduction Ticks | | | | | | | | |
|---|---|---|---|---|---|---|---|---|---|
| Treatment Group[1] | Day 2 | Day 44 | Day 58 | Day 72 | Day 79 | Day 86 | Day 93 | Day 100 | Day 107 |
| Group 6 | | | | | | | | | |
| % Reduction | 100.0 | 100.0 | 99.5 | 100.0 | 98.8 | 100.0 | 98.9 | 99.4 | 99.4 |
| Group 7 | | | | | | | | | |
| % Reduction | 100.0 | 100.0 | 100.0 | 100.0 | 100.0 | 100.0 | 97.9 | 100.0 | 100.0 |

Examples 7-12

Following similar procedures to those described in Examples 2 and 3, the oral compositions of the invention were found to be highly effective against *Rhipicephalus sanguineus, Dermacentor reticulatus, Dermacentor variabilis, Ixodes ricinus, Ixodes scapularis* and *Haemaphysalis longicornis* on dogs. For example, at a dose of 2.5 mg/kg, a chewable composition according to Table 10 was found to be have an efficacy of greater than 95% through Day 37 against *D. sanguineus*; an efficacy of greater than 95% through Day 30 against *D. reticulatus* and *D. variabilis*; and an efficacy of 100% against *I. ricinus* (99.6% at Day 30 and 100.0% again at Day 37); greater than 98% through Day 23 and greater than 94% through Day 30 against *I. scapularis*; and greater than 95% through Day 23 and greater than 90% through Day 30 against *H. longicornis*.

Example 13

Efficacy of Soft Chewable Compositions Comprising Compound a in Combination with a Macrocyclic Lactone Against *Toxocara canis* (Roundworm) in Dogs Three Treatment Groups of nine Beagle dogs infected with *T. canis* were formed. Dogs in Group 1 were not treated. On Day 0 of the study, dogs in Group 2 were treated with the soft chewable composition described in Table 11 containing 7.5 mg milbemycin oxime, a macrocyclic lactone active agent, per 2 gram soft chew to deliver a dose of approximately 0.5 mg/kg of the active agent per body weight of animal. The On Day 0, the dogs in Group 3 were treated with the soft chewable composition described in Table 12 containing 7.5 mg milbemycin oxime and 37.5 mg Compound A per 2 gram chew to deliver doses of 0.5 mg/kg milbemycin oxime and 2.5 mg/kg Compound A. After 8 days, the dogs were evaluated for the presence of *T. canis* infections.

The dogs in the control group (Group 1) were found to contain from 6 to 32 adult *T. canis* worms (geometric mean 13.5). No worms were found in any dog in Group 2 and one worm was found in one dog of Group 3. The study shows that soft chewable compositions containing milbemycin oxime alone or in combination with an isoxazoline active agent (Compound A) were highly efficacious against *T. canis* infections in dogs.

Example 14

Efficacy of Soft Chewable Compositions Comprising Compound A in Combination with a Macrocyclic Lactone Against *Trichuris vulpis* (Whipworm) in Dogs Three Treatment Groups of eight dogs naturally infected with *T. vulpis* were formed. Dogs in Group 1 were not treated. On Day 0 of the study, dogs in Groups 2 and 3 were treated with the soft chewable compositions described in Example 13 containing milbemycin oxime alone (Group 2) or a combination of milbemycin oxime with Compound A (Group 3) to deliver doses of 0.5 mg/kg milbemycin oxime and 2.5 mg/kg Compound A.

After 7 days, the dogs were evaluated for the presence of *T. vulpis* infections. Seven of the dogs in Group 1 were found to contain at least nine *T. vulpis*. Parasite counts indicated that the composition containing milbemycin oxime alone had an efficacy of >94% against *T. vulpis* while the soft chew composition containing a combination of milbemycin oxime and Compound A exhibited an efficacy of >98% against *T. vulpis*. The study shows that soft chewable compositions containing milbemycin oxime alone or in combination with an isoxazoline active agent (Compound A) are highly effective against *T. vulpis*.

Example 15

Efficacy of Soft Chewable Compositions Comprising Compound A in Combination with a Macrocyclic Lactone Against *Ancylostoma caninum* (hookworms) in Dogs Three Treatment Groups of nine dogs naturally infected with *A. caninum* were formed. Dogs in Group 1 were not treated. On Day 0 of the study, dogs in Groups 2 and 3 were treated with the soft chewable compositions described in Example 13 containing milbemycin oxime alone (Group 2) or a combination of milbemycin oxime and Compound A (Group 3) to deliver doses of 0.5 mg/kg milbemycin oxime and 2.5 mg/kg Compound A.

After 7 days, the dogs were evaluated for the presence of *A. caninum* infections. Examination of fecal samples prior to administration of the soft chew compositions confirmed that the dogs in the study shed ≥50 hookworm eggs per gram of fecal matter. Parasite counts indicated that the composition containing either milbemycin oxime alone or a combination of milbemycin oxime and Compound A had efficacies of >95% against *A. caninum*. The study shows that soft chewable compositions containing milbemycin oxime alone or in combination with an isoxazoline active agent (Compound A) are highly effective against *A. caninum*.

Example 16

Efficacy of Soft Chewable Compositions Comprising Compound A in Combination with a Macrocyclic Lactone Against *Dirofilaria immitis* (heartworm) in Dogs Three Treatment Groups of eight dogs infected with *D. immitis* were formed. Dogs in Group 1 were not treated. On Day 0 of the study, dogs in Group 2 were treated with the soft chewable composition described in Table 33 containing 7.5 mg milbemycin oxime, a macrocyclic lactone active agent, per 2 gram soft chew to deliver a dose of approximately 0.5 mg/kg of the active agent per body weight of animal. The dogs in Group 3 were treated with the soft chewable composition described in Table 34 containing 7.5 mg milbemycin oxime and 37.5 mg Compound A per 2 gram chew to deliver doses of 0.5 mg/kg milbemycin oxime and 2.5 mg/kg Compound A on Day 0 of the study.

After 119 days, the dogs were evaluated for the presence of *D. immitis* infections. Dogs in the control group exhibited 0 to 15 adult *D. immitis* worms (geometric mean of 2.4). Adult worms were recovered from 5 of the 8 control animals. No worms were recovered from any of the treated dogs in Groups 2 and 3. Therefore, the study demonstrates that soft chewable compositions containing milbemycin oxime alone or in combination with an isoxazoline active agent (Compound A) are highly effective against *D. immitis* (heartworm) in dogs.

Example 17

Efficacy of Soft Chewable Compositions Comprising a Combination of Moxidectin and Milbemycin Oxime Against *Dirofilaria immitis* (Heartworm) in Dogs Following a procedure similar to that of Example 16, the effectiveness of the soft chewable compositions comprising moxidectin and milbemycin oxime were evaluated against *D. immitis* in dogs. Dogs in the treatment group were treated with the soft chewable compositions containing moxidectin or milbemycin oxime described in Tables 35 and 36 to provide doses of 40 micrograms/kg moxidectin and 500 micrograms/kg milbemycin oxime. At the conclusion of the study, the soft chewable compositions were found have a high level of efficacy versus an untreated control group.

Example 18

Efficacy of Soft Chewable Compositions Comprising a Combination of Ivermectin and Milbemycin Oxime Against *Dirofilaria immitis* (Heartworm) in Dogs Following a procedure similar to that of Example 16, the effectiveness of the soft chewable compositions comprising ivermectin and milbemycin oxime were evaluated against *D. immitis* in dogs. Dogs in the treatment group were treated with the soft chewable compositions containing ivermectin or milbemycin oxime described in Tables 37 and 39 to provide doses of 20 micrograms/kg ivermectin and 500 micrograms/kg milbemycin oxime. At the conclusion of the study, the soft chewable compositions were found have a high level of efficacy versus an untreated control group.

As the non-limiting examples above demonstrate, the soft chewable veterinary compositions of the invention comprising at least one isoxazoline active agent show superior long lasting efficacy against ectoparasites in a mammal (e.g. dog and cat), and compositions comprising at least one isoxazoline active agent in combination with a macrocyclic lactone active agent are highly efficacious against endoparasites in mammals.

The invention is further described in the following numbered paragraphs:

1. A soft chewable veterinary composition for treating and/or preventing a parasitic infection or infestation in an animal comprising:
a)
(i) at least one isoxazoline active agent of Formula (I):

wherein:
$A^1, A^2, A^3, A^4, A^5$ and $A^6$ are independently selected from the group consisting of $CR^3$ and N, provided that at most 3 of $A^1, A^2, A^3, A^4, A^5$ and $A^6$ are N;
$B^1, B^2$ and $B^3$ are independently selected from the group consisting of $CR^2$ and N;
W is O or S;
$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;
each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;
each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —NO$_2$;
$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
$R^5$ is H, OR$^{10}$, NR$^{11}$R$^{12}$ or Q$^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or
$R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;
each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$;
each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —NH$_2$, —CN or —NO$_2$; or Q$^2$;
each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or NO$_2$;
each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, phenyl or pyridinyl;
$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;
$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
$R^{12}$ is H; Q$^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or
$R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;
Q$^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2; or (ii) at least one systemically-acting active agent that is active against internal parasites, wherein the systemically-acting active agent is one or more macrocyclic lactones, one or more benzimidazoles, levamisole, pyrantel, morantel, praziquantel, closantel, clorsulon, one or more amino acetonitrile active agents, one or more insect growth regulators or one or more aryloazol-2-yl cyanoethylamino active agents, or a combination of thereof; or (iii) a combination of at least one isoxazoline active agent of formula (I) and at least one systemically-acting active agent, wherein the systemically active agent is one or more macrocyclic lactones, one or more spinosyn compounds, one or more spinosoid compounds, one or more benzimidazoles, levamisole, pyrantel, morantel, praziquantel, closantel, clorsulon, one or more amino acetonitrile active agents, one or more insect growth regulators, one or more neonicotinoids or one or more aryloazol-2-yl cyanoethylamino active agents, or a combination of thereof; and b) a pharmaceutically acceptable carrier.

2. The soft chewable veterinary composition of paragraph 1, wherein:

W is O;
$R^4$ is H or $C_1$-$C_6$ alkyl;
$R^5$ is —$CH_2C(O)NHCH_2CF_3$;
each of $A^1$, $A^2$, $A^3$, $A^4$, $A^5$ and $A^6$ is CH;
$R^1$ is $C_1$-$C_6$ alkyl each optionally substituted with one or more substituents independently selected from $R^6$;
$R^6$ is halogen or $C_1$-$C_6$ alkyl; and
$B^1$, $B^2$, and $B^3$ are independently CH, C-halogen, C—$C_1$-$C_6$ alkyl, C—$C_1$-$C_6$haloalkyl, or C—$C_1$-$C_6$ alkoxy.

3. The soft chewable veterinary composition of paragraph 1, wherein:

W is O;
$R^1$ is $CF_3$;
$B^2$ is CH;
$B^1$ is C—Cl;
$B^3$ is C—$CF_3$;
each of $A^1$, $A^2$, $A^3$, $A^4$, $A^5$ and $A^6$ is CH;
$R^4$ is H; and
$R^5$ is —$CH_2C(O)NHCH_2CF_3$.

4. The soft chewable veterinary composition of paragraph 1, wherein the carrier comprises one or more fillers, at least one flavoring agent, at least one binder, one or more solvents, one or more surfactants, at least one humectant, optionally an antioxidant, and optionally a preservative.

5. The soft chewable veterinary composition of paragraph 4, wherein the one or more fillers is soy protein fines, corn starch, or a mixture thereof 6. The soft chewable veterinary composition of paragraph 4, wherein the binder is polyvinylpyrrolidone or a polyethylene glycol, or a combination thereof 7. The soft chewable veterinary composition of paragraph 4, wherein the solvent is a liquid polyethylene glycol or a caprylic/capric triglyceride, or a combination thereof.

8. The soft chewable veterinary composition of paragraph 4, wherein the surfactant is polyethylene glycol hydroxystearate.

9. The soft chewable veterinary composition of paragraph 4, wherein the humectant is glycerin.

10. The soft chewable veterinary composition of paragraph 4, wherein the flavoring agent is an artificial meat or beef flavor.

11. The soft chewable veterinary composition of paragraph 4, wherein the composition comprises:

a) a filler selected from corn starch, pre-gelatinized corn starch, corn gluten meal and soy protein fines, or a combination thereof;

b) a solvent selected from liquid polyethylene glycols, propylene glycol, propylene carbonate, caprylic/capric triglycerides, caprylic/capric/linoleic triglycerides, caprylic/capric/succinic triglycerides, propylene glycol dicaprylate/dicaprate, glycerol caprylate/caprate and polyglycolized glycerides, or a combination thereof;

c) a binder selected from polyvinylpyrrolidone, polyethylene glycols, co-polymers of vinyl acetate and vinylpyrrolidone, potato starch and corn starch, or a combination thereof;

d) a humectant selected from glycerol, propylene glycol, cetyl alcohol, glycerin monostearate and polyethylene glycols, or a combination thereof;

e) a surfactant selected from glyceryl monooleate, polyoxyethylene sorbitan fatty acid esters, sorbitan esters, polyvinyl alcohol, polysorbates, sodium lauryl sulfate, co-polymers of ethylene oxide and propylene oxide, propylene glycol monolaurate, glycerol caprylate/caprate, polyglycolized glycerides and polyethylene glycol hydroxystearate, or a combination thereof; and f) a natural or artificial beef or meat flavor.

12. The soft chewable veterinary composition of paragraph 11, wherein the composition comprises a compound of formula (I) at a concentration of about 1% to about 20% by weight.

13. The soft chewable veterinary composition of paragraph 12, wherein:

a) the filler is a combination of corn starch and soy protein fines and is present at a concentration of about 30% to about 50% (w/w);

b) the solvent is a mixture of liquid polyethylene glycol and caprylic/capric triglycerides and is present at a concentration of about 5% to about 20% (w/w);

c) the binder is polyethylene glycol or polyvinylpyrrolidone, or a combination thereof, and is present at a concentration of about 5% to about 15% (w/w);

d) the humectant is glycerin and is present at a concentration of about 5% to about 20%;

e) the surfactant is polyethylene glycol 12-hydroxystearate or polyoxyl hydrogenated castor oil and is present at a concentration of about 1% to about 5% (w/w).

14. The soft chewable veterinary composition of paragraph 12, wherein the compound of Formula (I) is present at a concentration of about 1% to about 5% by weight.

15. The soft chewable veterinary composition of paragraph 12, wherein the compound of Formula (I) is present at a concentration of about 10% to about 20% by weight.

16. The soft chewable veterinary composition of paragraph 1, wherein the composition comprises a systemically-acting active agent that is active against selected from the group consisting of one or more macrocyclic lactones, one or more spinosyn compounds, one or more spinosoid compounds, one or more benzimidazoles, levamisole, pyrantel, morantel, praziquantel, closantel, clorsulon, one or more amino acetonitrile active agents, one or more insect growth regulators, one or more neonicotinoids and one or more aryloazol-2-yl cyanoethylamino active agents, or a combination of thereof.

17. The soft chewable veterinary composition of paragraph 1, wherein the composition comprises a combination of at least one isoxazoline active agent of formula (I) and at least one systemically-acting active agent selected from the group consisting of one or more macrocyclic lactones, one or more spinosyn compounds, one or more spinosoid compounds, one or more benzimidazoles, levamisole, pyrantel, morantel, praziquantel, closantel, clorsulon, one or more amino acetonitrile active agents, one or more insect growth regulators, one or more neonicotinoids and one or more aryloazol-2-yl cyanoethylamino active agents, or a combination of thereof 18. The soft chewable veterinary composition of paragraph 17, wherein the macrocyclic lactone is eprinomectin, ivermectin, selamectin, milbemectin, milbemycin D, milbemycin oxime, or moxidectin, or a combination thereof.

19. The soft chewable veterinary composition of paragraph 17, wherein the isoxazoline active agent is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide and the systemically-acting active agent is an avermectin, milbemycin oxime or moxidectin, or a combination thereof.

20. A method for the treatment and/or prevention of a parasitic infestation and/or infection in an animal comprising administering to the animal an effective amount of the soft chewable veterinary composition of claim 1 to the animal.

21. The method of paragraph 20, wherein the composition comprises an isoxazoline active agent, and wherein the isoxazoline active agent is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

22. The method of paragraph 20, wherein the soft chewable composition comprises a systemically-acting active agent selected from the group consisting of one or more avermectin or milbemycin compounds, one or more benzimidazole active agents, one or more a spinosyn compounds, one or more a spinosoid compounds, levamisole, pyrantel, morantel, praziquantel, closantel, clorsulon, one or more amino acetonitrile active agents, one or more insect growth regulators, one or more neonicotinoids and one or more aryloazol-2-yl cyanoethylamino active agents, or a combination of thereof.

23. The method of paragraph 20, wherein the parasite are fleas or ticks.

24. The method of paragraph 21, wherein the parasite is a nematode, a cestode, a trematode or a filarial parasite.

25. Use of a compound of Formula (I) in paragraph 1 in the manufacture of a soft chewable veterinary composition for the treatment and/or prevention of a parasitic infestation and/or infection in an animal.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A soft chewable veterinary composition for treating and/or preventing a parasitic infection or infestation in an animal comprising:

a)
at least one isoxazoline active agent of Formula (I):

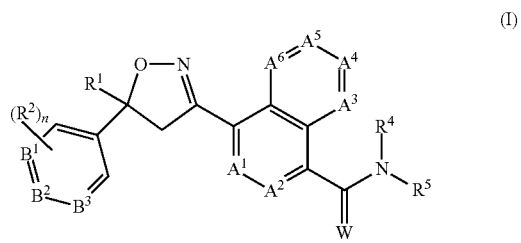

wherein:
$A^1, A^2, A^3, A^4, A^5$ and $A^6$ are independently selected from the group consisting of $CR^3$ and N, provided that at most 3 of $A^1, A^2, A^3, A^4, A^5$ and $A^6$ are N;

$B^1, B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or $NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from the group consisting of up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2;

and b) a pharmaceutically acceptable carrier;
wherein the pharmaceutically acceptable carrier comprises:
i) a surfactant selected from the group consisting of polyethylene glycol stearates and polyethylene glycol hydroxystearates;
ii) one or more fillers,
iii) one or more binders; and
iv) at least one humectant, solvent or lubricant, or combination thereof.

2. The soft chewable veterinary composition of claim 1, wherein:
W is O;
$R^4$ is H or $C_1$-$C_6$ alkyl;
$R^5$ is —$CH_2C(O)NHCH_2CF_3$;
each of $A^1$, $A^2$, $A^3$, $A^4$, $A^5$ and $A^6$ is CH;
$R^1$ is $C_1$-$C_6$ alkyl each optionally substituted with one or more substituents independently selected from $R^6$;
$R^6$ is halogen or $C_1$-$C_6$ alkyl; and
$B^1$, $B^2$, and $B^3$ are independently CH, C-halogen, C—$C_1$-$C_6$ alkyl, C—$C_1$-$C_6$ haloalkyl, or C—$C_1$-$C_6$ alkoxy.

3. The soft chewable veterinary composition of claim 1, wherein:
W is O;
$R^1$ is $CF_3$;
$B^2$ is CH;
$B^1$ is C—Cl;
$B^3$ is C—$CF_3$;
each of $A^1$, $A^2$, $A^3$, $A^4$, $A^5$ and $A^6$ is CH;
$R^4$ is H; and
$R^5$ is —$CH_2C(O)NHCH_2CF_3$.

4. The soft chewable veterinary composition of claim 1, wherein the carrier further comprises at least one flavoring agent, optionally an antioxidant, and optionally a preservative.

5. The soft chewable veterinary composition of claim 1, wherein the one or more fillers are soy protein fines, corn starch, or a mixture thereof.

6. The soft chewable veterinary composition of claim 1, wherein the binder is polyvinylpyrrolidone, a co-polymer of vinyl acetate and vinyl pyrrolidone or a polyethylene glycol, or a combination thereof.

7. The soft chewable veterinary composition of claim 1, wherein the composition comprises a solvent and the solvent is a liquid polyethylene glycol or a caprylic/capric triglyceride, or a combination thereof.

8. The soft chewable veterinary composition of claim 1, wherein the surfactant is a polyethylene glycol hydroxystearate.

9. The soft chewable veterinary composition of claim 1, wherein composition comprises a humectant and the humectant is glycerin or propylene glycol.

10. The soft chewable veterinary composition of claim 4, wherein the flavoring agent is an artificial meat or beef flavor.

11. The soft chewable veterinary composition of claim 4, wherein the composition comprises:
a) a filler selected from the group consisting of corn starch, pre-gelatinized corn starch, corn gluten meal, soy protein fines, and a combination thereof;
b) a solvent selected from the group consisting of liquid polyethylene glycols, propylene glycol, propylene carbonate, caprylic/capric triglycerides, caprylic/capric/linoleic triglycerides, caprylic/capric/succinic triglycerides, propylene glycol dicaprylate/dicaprate, glycerol caprylate/caprate, polyglycolized glycerides, and a combination thereof;
c) a binder selected from the group consisting of polyvinylpyrrolidone, polyethylene glycols, co-polymers of vinyl acetate and vinylpyrrolidone, potato starch, corn starch, and a combination thereof;
d) a humectant selected from the group consisting of glycerol, propylene glycol, cetyl alcohol, glycerin monostearate, polyethylene glycols, and a combination thereof;
and
e) a natural or artificial beef or meat flavor.

12. The soft chewable veterinary composition of claim 11, wherein the composition comprises a compound of formula (I) at a concentration of about 1% to about 20% by weight.

13. The soft chewable veterinary composition of claim 12, wherein:
a) the filler is a combination of corn starch and soy protein fines and is present at a concentration of about 30% to about 60% (w/w);
b) the solvent is a mixture of liquid polyethylene glycol and caprylic/capric triglycerides and is present at a concentration of about 5% to about 20% (w/w);

c) the binder is polyethylene glycol or polyvinylpyrrolidone, or a combination thereof, and is present at a concentration of about 5% to about 15% (w/w);
d) the humectant is glycerin and is present at a concentration of about 5% to about 20%;
e) the surfactant is a polyethylene glycol 12-hydroxystearate and is present at a concentration of about 1% to about 5% (w/w).

14. The soft chewable veterinary composition of claim 12, wherein the compound of Formula (I) is present at a concentration of about 1% to about 5% by weight.

15. The soft chewable veterinary composition of claim 12, wherein the compound of Formula (I) is present at a concentration of about 10% to about 20% by weight.

16. The composition of claim 1, wherein the isoxazoline active agent of formula (I) is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

17. The composition of claim 1, wherein the surfactant is a polyethylene glycol 12-hydroxystearate.

18. The composition of claim 1, wherein the surfactant is polyethylene glycol 15 12-hydroxystearate.

19. The composition of claim 13, wherein the surfactant is polyethylene glycol 15 12-hydroxystearate.

20. The composition of claim 13, wherein the isoxazoline active agent of formula (I) is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

21. The composition of claim 11, wherein the filler is corn starch or soy protein fines, or a combination thereof.

22. The composition of claim 11, wherein the solvent is liquid polyethylene glycols or caprylic/capric triglycerides, or a combination thereof.

23. The composition of claim 11, wherein the binder is polyvinylpyrrolidone, a co-polymer of vinyl acetate and vinylpyrrolidone or a polyethylene glycol, or a combination thereof.

24. The composition of claim 11, wherein the humectant is glycerol, propylene glycol, or a combination thereof.

25. The composition of claim 11, wherein:
a) the filler is corn starch or soy protein fines, or a combination thereof;
b) the binder is polyvinylpyrrolidone, a co-polymer of vinyl acetate and vinylpyrrolidone or polyethylene glycol, or a combination thereof; and
c) humectant is glycerol, propylene glycol, or a combination thereof.

26. The composition of claim 25, wherein:
a) the filler is a combination of corn starch and soy protein fines;
b) the solvent is liquid polyethylene glycols or caprylic/capric triglycerides, or a combination thereof;
c) the binder is polyvinylpyrrolidone or polyethylene glycol; and
d) the humectant is glycerol.

27. The composition of claim 25 or 26, wherein the isoxazoline active agent of formula (I) is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

28. The composition of claim 13, wherein:
a) the filler is present at a concentration of about 35% to about 55% (w/w);
b) the solvent is present at a concentration of about 5% to about 15% (w/w);
c) the binder is present at a concentration of about 5% to about 10% (w/w); and
d) the humectant is present at a concentration of about 5% to about 15% (w/w).

29. The composition of claim 28, wherein the isoxazoline active agent of formula (I) is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

30. The composition of claim 4, wherein the composition is selected from the group consisting of:

| Ingredients | Function | % (w/w) |
|---|---|---|
| Cmpd. A | Active | 2.2 |
| Soy Protein Fines | Filler | 26.5 (QS) |
| Corn Starch | Filler | 31.0 |
| artificial meat flavor | Flavoring | 5.1 |
| artificial beef flavor | Flavoring | 7.1 |
| Povidone K-30 | Binder | 2.8 |
| PEG 400 | Solvent | 7.1 |
| PEG 4000 | Binder | 6.4 |
| polyethylene glycol 12-hydroxystearate | Surfactant | 3.0 |
| Glycerin | Humectant | 5.1 |
| Potassium Sorbate | Preservative | 0.3 |
| Caprylic/capric triglyceride | Solvent/Lubricant | 3.2; |

| Ingredients | Function | % (w/w) |
|---|---|---|
| Cmpd. A | Active | 1.5 |
| Soy Protein Fines | Filler | 46.5 (QS) |
| beef flavor | Flavoring | 20.0 |
| Povidone K-30 | Binder | 7.0 |
| PEG 400 | Solvent | 15 |
| polyethylene glycol 12-hydroxystearate | Surfactant | 3.0 |
| Caprylic/capric triglyceride | Solvent/lubricant | 7.0; |

| Ingredients | Function | % (w/w) |
|---|---|---|
| Cmpd. A | Active | 1.875 |
| Soy Protein Fines | Filler | 46.1 (QS) |
| beef flavor | Flavoring | 20.0 |
| Povidone K-30 | Binder | 8.5 |
| PEG 400 | Solvent | 15.5 |
| polyethylene glycol 12-hydroxystearate | Surfactant | 3.0 |
| Caprylic/capric triglyceride | Solvent/lubricant | 5.0; |

| Ingredients | Function | % (w/w) |
|---|---|---|
| Cmpd. A | Active | 1.875 |
| Soy Protein Fines | Filler | 36.1 (QS) |
| beef flavor | Flavoring | 20.0 |
| Povidone K-30 | Binder | 8.5 |
| PEG 400 | Solvent | 15.5 |
| polyethylene glycol 12-hydroxystearate | Surfactant | 3.0 |
| Caprylic/capric triglyceride | Solvent/lubricant | 5.0 |
| Croscarmellose sodium | disintegrant | 10.0; |

| Ingredients | Function | % (w/w) |
|---|---|---|
| Cmpd. A | Active | 2.3 |
| Soy Protein Fines | Filler | 20.6 (QS) |
| Corn Starch | Filler | 25.0 |

| Ingredients | Function | % (w/w) |
| --- | --- | --- |
| beef flavor | Flavoring | 20.5 |
| Povidone K-30 | Binder | 2.8 |
| PEG 400 | Solvent | 7.2 |
| PEG 4000 | Binder | 6.4 |
| polyethylene glycol 12-hydroxystearate | Surfactant | 3.1 |
| Glycerin | Humectant | 8.6 |
| Potassium Sorbate | Preservative | 0.3 |
| Caprylic/capric triglyceride | Solvent/Lubricant | 3.1; |

| Ingredients | Function | % (w/w) |
| --- | --- | --- |
| Cmpd. A | Active | 2.3 |
| Soy Protein Fines | Filler | 20.0 (QS) |
| Corn Starch | Filler | 25.0 |
| beef flavor | Flavoring | 20.0 |
| Povidone K-30 | Binder | 2.8 |
| PEG 400 | Solvent | 7.1 |
| PEG 4000 | Binder | 6.4 |
| polyethylene glycol 12-hydroxystearate | Surfactant | 3.1 |
| Glycerin | Humectant | 10.0 |
| Potassium Sorbate | Preservative | 0.3 |
| Caprylic/capric triglyceride | Solvent/Lubricant | 3.2; |

| Ingredients | Function | % (w/w) |
| --- | --- | --- |
| Cmpd. A | Active | 0.5 |
| Soy Protein Fines | Filler | 16.6 |
| Corn Starch | Filler | 32.5 (QS) |
| beef flavor | Flavoring | 19.4 |
| Povidone K-30 | Binder | 2.6 |
| PEG 400 | Solvent | 7.8 |
| PEG 4000 | Binder | 6.1 |
| polyethylene glycol 12-hydroxystearate | Surfactant | 4.7 |
| Lauroyl polyoxyl-32 glycerides | Surfactant | 4.7 |
| Potassium Sorbate | Preservative | 0.3 |
| Caprylic/capric triglyceride | Solvent/Lubricant | 4.9; |

| Ingredients | Function | % (w/w) |
| --- | --- | --- |
| Cmpd. A | Active | 0.5 |
| Soy Protein Fines | Filler | 26.9 (QS) |
| Corn Starch | Filler | 23.4 |
| beef flavor | Flavoring | 20.0 |
| PEG 400 | Solvent | 6.8 |
| PEG 4000 | Binder | 5.8 |
| polyethylene glycol 12-hydroxystearate | Surfactant | 4.8 |
| Lauroyl polyoxyl-32 glycerides | Surfactant | 6.3 |
| Potassium Sorbate | Preservative | 0.3 |
| Caprylic/capric triglyceride | Solvent/Lubricant | 5.2; |

| Ingredients | Function | % (w/w) |
| --- | --- | --- |
| Cmpd. A | Active | 0.5 |
| Soy Protein Fines | Filler | 41.6 (QS) |
| beef flavor | Flavoring | 19.9 |
| Povidone K-30 | Binder | 4.6 |
| PEG 400 | Solvent | 15.1 |
| PEG 4000 | Binder | 8.1 |
| polyethylene glycol 12-hydroxystearate | Surfactant | 4.6 |

| Ingredients | Function | % (w/w) |
| --- | --- | --- |
| Potassium Sorbate | Preservative | 0.3 |
| Caprylic/capric triglyceride | Solvent/Lubricant | 4.6; |

| Ingredients | Function | % (w/w) |
| --- | --- | --- |
| Cmpd. A | Active | 0.5 |
| Corn Starch | Filler | 40.8 (QS) |
| beef flavor | Flavoring | 19.9 |
| Povidone K-30 | Binder | 5.7 |
| PEG 400 | Solvent | 11.4 |
| PEG 4000 | Binder | 5.7 |
| polyethylene glycol 12-hydroxystearate | Surfactant | 2.7 |
| Lauroyl polyoxyl-32 glycerides | Surfactant | 2.7 |
| Potassium Sorbate | Preservative | 0.3 |
| Caprylic/capric triglyceride | Solvent/Lubricant | 5.4 |
| Sodium Starch glycolate | Disintegrate | 5.0; |

| Ingredients | Function | % (w/w) |
| --- | --- | --- |
| Cmpd. A | Active | 0.5 |
| Soy Protein Fines | Filler | 19.4 |
| Corn Starch | Filler | 24.0 (QS) |
| beef flavor | Flavoring | 19.2 |
| Povidone K-30 | Binder | 2.6 |
| PEG 400 | Solvent | 8.6 |
| PEG 4000 | Binder | 6.0 |
| polyethylene glycol 12-hydroxystearate | Surfactant | 4.6 |
| Lauroyl polyoxyl-32 glycerides | Surfactant | 4.6 |
| Potassium Sorbate | Preservative | 0.3 |
| Caprylic/capric triglyceride | Solvent/Lubricant | 5.3 |
| Glycerin | Humectant | 4.8; |

| Ingredients | Function | % (w/w) |
| --- | --- | --- |
| Cmpd. A | Active | 2.3 |
| Soy Protein Fines | Filler | 22.0 (QS) |
| Corn Starch | Filler | 26.4 |
| beef flavor | Flavoring | 10.0 |
| Artificial Powdered Meat Flavor | Flavoring | 10.0 |
| Povidone K-30 | Binder | 2.7 |
| PEG 400 | Solvent | 7.0 |
| PEG 4000 | Binder | 6.25 |
| polyethylene glycol 12-hydroxystearate | Surfactant | 3.0 |
| Glycerin | Humectant | 7.0 |
| Potassium Sorbate | Preservative | 0.3 |
| Caprylic/capric triglyceride | Solvent/Lubricant | 3.0; |

| Ingredients | Function | % (w/w) |
| --- | --- | --- |
| Cmpd. A | Active | 13.6 |
| Soy Protein Fines | Filler | 15-25 (QS) |
| Corn Starch | Filler | 15-25 |
| beef flavor | Flavoring | 20 |
| PEG 400 | Solvent | 11.9 |
| PEG 4000 | Binder | 5 |
| polyethylene glycol 12-hydroxystearate | Surfactant | 3-5 |
| Glycerin | Humectant | 2-5 |
| Potassium Sorbate | Preservative | 0.3; |

| Ingredients | Function | % (w/w) |
| --- | --- | --- |
| Cmpd. A | Active | 13.6 |
| Soy Protein Fines | Filler | 12.6 |
| Corn Starch | Filler | 25 (QS) |
| beef flavor | Flavoring | 20 |
| Povidone K-30 | Binder | 2.75 |
| PEG 400 | Solvent | 5.5 |
| PEG 4000 | Binder | 6.2 |
| polyethylene glycol 12-hydroxystearate | Surfactant | 5.0 |
| Glycerin | Humectant | 7-8 |
| Potassium Sorbate | Preservative | 0.3 |
| Caprylic/capric triglyceride | Solvent/Lubricant | 2.0; |

| Ingredients | Function | % (w/w) |
| --- | --- | --- |
| Cmpd. A | Active | 13.6 |
| Soy protein fines | Filler | 15.2 (QS) |
| Corn Starch | Filler | 25 |
| beef flavor | Flavoring | 20 |
| PEG 400 | Solvent | 11.9 |
| PEG 4000 | Binder | 5.0 |
| polyethylene glycol 12-hydroxystearate | Surfactant | 5.0 |
| Caprylic/capric triglyceride | Solvent/lubricant | 1.0 |
| Glycerin | Humectant | 3.0 |
| Potassium Sorbate | Preservative | 0.3; |

| Ingredients | Function | % (w/w) |
| --- | --- | --- |
| Cmpd. A | Active | 13.6 |
| Soy protein fines | Filler | 19.2 (QS) |
| Corn Starch | Filler | 20 |
| beef flavor | Flavoring | 20 |
| PEG 400 | Solvent | 11.9 |
| PEG 4000 | Binder | 5.0 |
| polyethylene glycol 12-hydroxystearate | Surfactant | 5.0 |
| Caprylic/capric triglyceride | Solvent/lubricant | 1.0 |
| Glycerin | Humectant | 4.0 |
| Potassium Sorbate | Preservative | 0.3; | and

| Ingredients | Function | % (w/w) |
| --- | --- | --- |
| Cmpd. A | Active | 13.6 |
| Soy protein fines | Filler | 24.2 (QS) |
| Corn Starch | Filler | 15 |
| beef flavor | Flavoring | 20 |
| PEG 400 | Solvent | 11.9 |
| PEG 4000 | Binder | 5.0 |
| polyethylene glycol 12-hydroxystearate | Surfactant | 5.0 |
| Caprylic/capric triglyceride | Solvent/lubricant | 1.0 |
| Glycerin | Humectant | 4.0 |
| Potassium Sorbate | Preservative | 0.3. |

31. A soft chewable veterinary composition for treating and/or preventing a parasitic infection or infestation in an animal comprising:

a) at least one isoxazoline active agent of Formula (I):

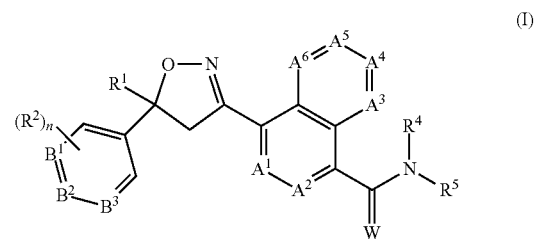

wherein:
$A^1, A^2, A^3, A^4, A^5$ and $A^6$ are independently selected from the group consisting of $CR^3$ and N, provided that at most 3 of $A^1, A^2, A^3, A^4, A^5$ and $A^6$ are N;

$B^1, B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or $NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from the group consisting of up to 1 O, up to 1 S and up to 3 N, each ring or ring system optionally substituted with one or more substituents independently selected from $R^8$;

each $Q_2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2; and b) a pharmaceutically acceptable carrier;
wherein the pharmaceutically acceptable carrier comprises:
i) a surfactant selected from the group consisting of polyoxyl 8 stearate, polyoxyl 40 stearate and polyethyleneglycol 12-hydroxystearate;
ii) one or more fillers;
iii) one or more binders; and
iv) at least one humectant, solvent or lubricant, or a combination thereof.

32. The soft chewable veterinary composition of claim 31, wherein:
W is O;
$R^1$ is $CF_3$;
$B^2$ is CH;
$B^1$ is C—Cl;
$B^3$ is C—$CF_3$;
each of $A^1$, $A^2$, $A^3$, $A^4$, $A^5$ and $A^6$ is CH;
$R^4$ is H; and
$R^5$ is —$CH_2C(O)NHCH_2CF_3$.

33. The soft chewable veterinary composition of claim 31, wherein the one or more fillers are soy protein fines, corn starch, or a mixture thereof.

34. The soft chewable veterinary composition of claim 31, wherein the binder is polyvinylpyrrolidone or a polyethylene glycol.

35. The soft chewable veterinary composition of claim 31, wherein the composition comprises a solvent and the solvent is a liquid polyethylene glycol or a caprilic/capric triglyceride.

36. The soft chewable veterinary composition of claim 31, wherein the composition comprises a humectant and the humectant is glycerol.

37. The soft chewable veterinary composition of claim 31, wherein the composition further comprises a flavoring agent, and wherein the flavoring agent is an artificial meat or beef flavor.

38. The soft chewable veterinary composition of claim 31, wherein:
a) the surfactant is a polyethyleneglycol 12-hydroxystearate and is present at a concentration of about 1% to about 5% (w/w);
b) the filler is a combination of corn starch and soy protein fines and is present at a concentration of about 30% to about 50% (w/w);
c) the composition comprises a solvent and the solvent is a mixture of liquid polyethylene glycol and caprilic/capric triglycerides and is present at a concentration of about 5% to about 20% (w/w);
d) the binder is a combination of polyethylene glycol and a polyvinylpyrrolidone and is present at a concentration of about 5% to about 15% (w/w); and
e) the composition comprises a humectant and the humectant is glycerol and is present at a concentration of about 5% to about 20% (w/w).

39. The soft chewable veterinary composition of claim 38, wherein:
W is O;
$R^1$ is $CF_3$;
$B^2$ is CH;
$B^1$ is C—Cl;
$B^3$ is C—$CF_3$;
each of $A^1$, $A^2$, $A^3$, $A^4$, $A^5$ and $A^6$ is CH;
$R^4$ is H; and
$R^5$ is —$CH_2C(O)NHCH_2CF_3$.

* * * * *